(12) United States Patent
Boeke et al.

(10) Patent No.: US 9,267,932 B2
(45) Date of Patent: Feb. 23, 2016

(54) SYNTHETIC MAMMALIAN RETROTRANSPOSON GENE

(75) Inventors: Jef D. Boeke, Baltimore, MD (US); Jeffrey S. Han, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1388 days.

(21) Appl. No.: 10/558,804

(22) PCT Filed: May 18, 2004

(86) PCT No.: PCT/US2004/015810
§ 371 (c)(1),
(2), (4) Date: Oct. 25, 2006

(87) PCT Pub. No.: WO2005/049789
PCT Pub. Date: Jun. 2, 2005

(65) Prior Publication Data
US 2007/0098700 A1    May 3, 2007

Related U.S. Application Data

(60) Provisional application No. 60/473,658, filed on May 28, 2003.

(51) Int. Cl.
| | | |
|---|---|---|
| *A61K 48/00* | (2006.01) | |
| *C12Q 1/68* | (2006.01) | |
| *G01N 33/50* | (2006.01) | |
| *C07K 14/005* | (2006.01) | |
| *C12N 15/90* | (2006.01) | |

(52) U.S. Cl.
CPC .......... *G01N 33/5008* (2013.01); *C07K 14/005* (2013.01); *C12N 15/907* (2013.01); *A61K 48/00* (2013.01); *C12N 2740/10022* (2013.01); *C12N 2800/90* (2013.01)

(58) Field of Classification Search
CPC .... C12N 2800/90; C12N 15/90; C12N 15/52; C12N 15/85; C12N 2740/10022; A61K 48/00
See application file for complete search history.

(56) References Cited

U.S. PATENT DOCUMENTS

| | | | |
|---|---|---|---|
| 6,027,722 A * | 2/2000 | Hodgson | 424/93.21 |
| 6,150,160 A | 11/2000 | Kazazian, Jr. et al. | |
| 2007/0037759 A1* | 2/2007 | Deininger et al. | 514/44 |

FOREIGN PATENT DOCUMENTS

WO    WO-2004/072290 A    8/2004

OTHER PUBLICATIONS

Chakraborty et al., Synthetic retrotransposon vectors for gene therapy, FASEB, vol. 7, No. 10, (1993), pp. 971-977.
S. Boissinot et al., "L1 (Line-1) Retrotransposon Evolution and Amplification in Recent Human History", Molecular Biology and Evolution, vol. 17, No. 6, pp. 915-928, 2000.
Ostertag, E. et al., "Biology of mammalian L1 retrotransposons" Annu Rev Genet. 2001;35:501-38.
Wei, W. et al., "Human L1 retrotransposition: cis preference versus trans complementation" Mol Cell Biol.Feb. 2001;21(4):1429-39.
Wallace N, et al. "L1 mobile element expression causes multiple types of toxicity" Gene. Aug. 1, 2008;419(1-2):75-81.
An et al., "Conditional activation of a single-copy L1 transgene in mice by Cre." Genesis, 46(7):373-383 (2008).
An et al., "Active retrotransposition by a synthetic L1 element in mice." PNAS 103(49):18662-18667 (2006).
Martin et al., "Functional reverse transcriptases encoded by A-type mouse LINE-1: defining the minimal domain by deletion analysis." Gene. 215(1):69-75 (1998).
Moran, "Human L1 retrotransposition: insights and peculiarities learned from a cultured cell retrotransposition assay." Genetica. 107(1): 39-51 (1999).
Sinibaldi et al., "A role for endogenous reverse transcriptase in tumorigenesis and as a target in differentiating cancer therapy." Genes Chrom. Cancer 45(1): 1-10 (2006).
Brouha et al. Hot L1s account for the bulk of retrotransposition in the human population. Proc Natl Acad Sci USA. Apr. 29, 2003;100(9):5280-5.
Supporting information for Brouha et al. supporting Figure 6, "http://www.pnas.org/content/suppl/2003/03/31/0831042100.DC1/1042Fig6legend.html".
Hensel et al.. Simultaneous identification of bacterial virulence genes by negative selection. Science. Jul. 21, 1995;269(5222):400-3.
Loeb et al. The sequence of a large L1Md element reveals a tandemly repeated 5' end and several features found in retrotransposons. Mol Cell Biol. Jan. 1986;6(1):168-82.

* cited by examiner

*Primary Examiner* — Maria Marvich
(74) *Attorney, Agent, or Firm* — Mintz Levin Cohn Ferris Glovsky and Popeo, P.C.; Peter F. Corless, Esq.; Daniel W. Clarke

(57) ABSTRACT

The invention relates to synthetic transposon and retrotransposon genes that exhibit higher levels of expression relative to natural transposon and retrotransposon genes. The invention further relates to transposons and retrotransposons comprising such synthetic genes.

2 Claims, 44 Drawing Sheets

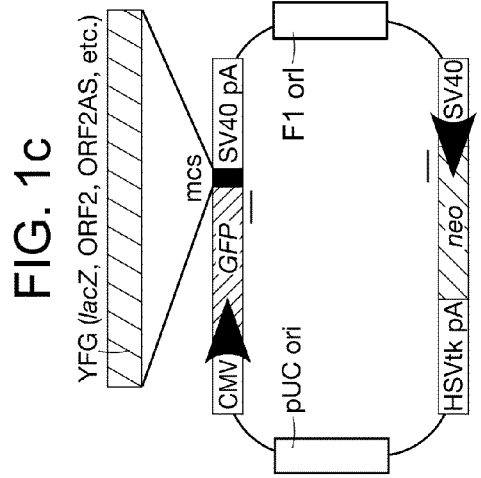
FIG. 1a
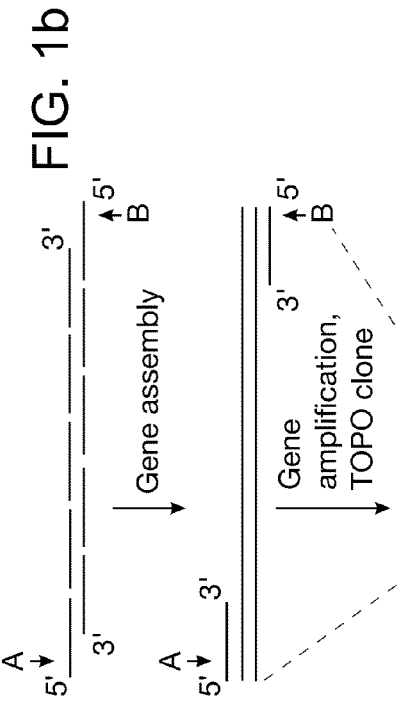
FIG. 1b
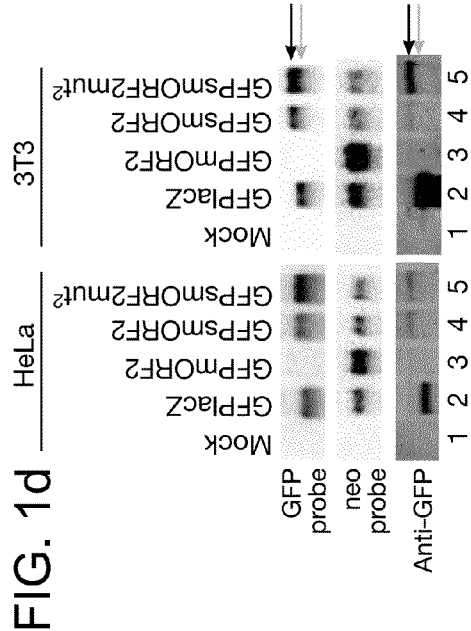
FIG. 1c
FIG. 1d

| Insertion no. | Poly(A)? | TSD? | 5' inversion? | Deletion? | Untemplated nucleotides? |
|---|---|---|---|---|---|
| 8 | Y | Y, 5 bp | N | N | Y, 7 bp |
| 10 | Y | N | N | Y, 10 bp | Y, 1 bp |
| 13 | Y | Y, 101 bp | N | N | N |
| 14 | Y | Y, 108 bp | N | N | N |
| 18 | Y | Y, 15 bp | Y | N | N |
| 23 | Y | Y, 23 bp | N | N | N |

Phenotype:
lacZ+
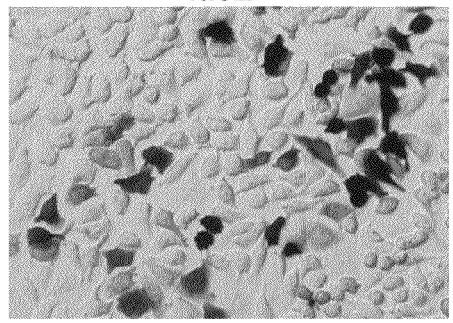
GFP−
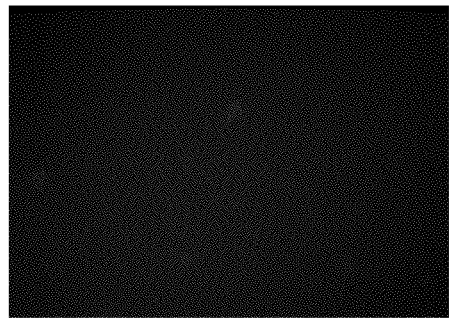
lacZ−
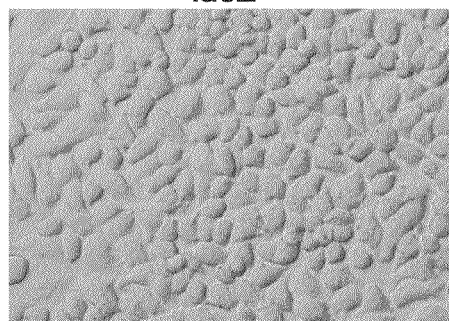
GFP+
FIG. 5b

FIG. 6

SEQ ID NO: 1

ATGCCCCCCCTGACCACCAAGATCACCGGCAGCAACAACTACTTCAGCCTGA
TCAGCCTGAACATCAACGGCCTGAACAGCCCCATCAAGCGGCACCGCCTGAC
CAACTGGCTGCACAAGCAGGACCCCACCTTCTGTTGCCTCCAGGAGACCCAC
CTGCGCGAGAAGGACCGGCACTACCTGCGGATGAAGGGCTGGAAGACCATC
TTTCAGGCCAACGGCATGAAGAAGCAGGCTGGCGTGGCCATCCTGATCAGCG
ACAAGATCGACTTCCAGCCCAAGGTGATCAAGAAGGACAAGGAGGGCCACT
TCATCCTGATCAAGGGCAAGATCCTGCAGGAGGAGCTGAGCATTCTGAACAT
CTACGCCCCCAACACCCGCGCCGCCACCTTCACCAAGGAGACCCTCGTGAAG
CTGAAGGCCCACATCGCTCCCCACACCATCATCGTCGGCGACTTCAACACCC
CCCTGAGCCCCATGGACAGATCTTGGAAGCAGAAGCTGAACCGCGACACCCT
GAAGCTGACCGAGGTGATGAAGCAGATGGACCTGACCGACATCTACCGCACC
TTCTACCCCAAGACCAAGGGCTACACCTTCTTCAGCGCTCCCCACGGCACCTT
CAGCAAGATCGACCACATCATCGGCCACAAGAGCGGGCTGAACCGGCTGAA
GAACATCGAGATCGTGCCCTGCATCCTGAGCGACCACCATGCCCTGCGCCTG
ATCTTCAACAACAAGATTAACAACCGCAAGCCCACCTTCACCTGGAAGCTGA
ACAACACCCTGCTGAACGACACCCTGGTGAAGGAAGGCATCAAGAAGGAGA
TCAAGGACTTCCTGGAGTTCAACGAGAACGAGGCCACCACCTACCCTAACCT
GTGGGACACCATGAAGGCCTTCCTGCGGGGCAAGCTGATCGCCATGAGCGCC
TTCAAGAAGAAGCGGGAGCGCGCCCACACTAGTAGCCTGACCACCCACCTGA
AGGCCCTGGAGAAGAAGGAGGCTAACTCCCCCAAGCGCTCCCGGCGGCAGG
AGATCATCAAGCTGCGCGGCGAGATCAACCAGGTGGAGACCCGGCGCACCA
TCCAACGGATCAACCAGACCCGGTCTTGGTTCTTCGAGAAGATCAACAAGAT
CGACAAGCCCCTGGCTCGCCTGACCAAGGGCCACCGCGACAAGATCCTGATC
AACAAGATCCGCAACGAGAAGGGCGACATCACCACCGACCCCGAGGAGATC
CAGAACACCATCCGCAGCTTCTACAAGCGCCTGTACAGCACCAAGCTGGAGA
ACCTGGACGAGATGGACAAGTTCCTGGACCGCTATCAGGTGCCCAAGCTGAA
CCAGGACCAGGTGGACCTGCTGAACAGCCCCATCTCCCCCAAGGAAATCGAG
GCCGTGATCAACAGCCTGCCCGCCAAGAAGAGCCCCGGCCCCGACGGCTTCA
GCGCTGAGTTCTACCAGACCTTCAAGGAGGACCTGACCCCCGTGCTGCACAA
GCTTTTCCACAAGATCGAGGTCGAGGGCATCCTCCCCAACAGCTTCTACGAG
GCCACCATCACCCTGATCCCCAAGCCCCAGAAGGACCCCACCAAGATCGAGA
ACTTCCGCCCCATCAGCCTGATGAACATCGACGCCAAGATCCTGAACAAGAT
CCTCGCCAACCGCATCCAGGAGCACATCAAGGCCATCATCCACCCTGACCAG
GTCGGCTTCATCCCCGGCATGCAGGGCTGGTTCAACATCCGCAAGAGCATCA
ACGTGATCCACTACATCAACAAGCTGAAGGACAAGAACCACATGATCATCAG
CCTGGACGCCGAGAAGGCCTTCGACAAGATCCAGCACCCCTTCATGATCAAG
GTCCTGGAGCGCAGCGGCATTCAGGGCCAGTACCTCAACATGATCAAGGCCA
TCTACAGCAAGCCCGTCGCCAACATCAAGGTGAACGGGGAGAAGCTGGAGG

FIG. 6 (continued)

```
CCATCCCTCTGAAGAGCGGCACGCGTCAGGGCTGTCCTCTGTCCCCCTACCTG
TTCAACATCGTGCTGGAGGTGCTGGCCCGCGCTATCCGGCAGCAGAAGGAGA
TCAAGGGCATCCAGATCGGCAAGGAGGAAGTGAAGATCAGCCTGTTCGCCGA
CGACATGATCGTGTACATCAGCGACCCCAAGAACAGCAACCGCGAGCTCCTG
AACCTGATCAACAGCTTCGGCGAGGTGGCTGGCTACAAGATCAACAGCAACA
AGAGCATGGCCTTCCTGTACACCAAGAACAAGCAGGCCGAGAAGGAGATCC
GCGAGACCACCCCCTTCAGCATCGCCACCAACAACATCAAGTACCTGGGCGT
GACCCTGACCAAGGAGGTGAAGGACCTGTACGACAAGAACTTCAAGAGCCT
GAAGAAGGAGATCAAGGAGGACCTGCGCCGCTGGAAGGACCTGCCCTGCAG
CTGGATCGGCCGCACCAACATCGTGAAGATGGCCATCCTGCCCAAGGCTATC
TACCGCTTCAACGCCATCCCCATCAAGATCCCCACCCAGTTCTTCAACGAGCT
CGAGGGCGCCATCTGCAAGTTCATCTGGAACAACAAGAAGCCCCGCATCGCC
AAGACCCTGCTGAAGGACAAGCGCACCAGTGGGGGGATCACCATGCCCGAC
CTGAAGCTGTACTACCGCGCCATCGTGATCAAGACCGCCTGGTACTGGTACC
GCGACCGCCAGGTGGACCAGTGGAACCGCATCGAGGACCCCGAGATGAACC
CCCACACCTACGGCCACCTGATCTTCGACAAGGGCGCCAAGACCATCCAGTG
GAAGAAGGACAGCATCTTCAACAACTGGTGCTGGCACAACTGGCTGCTGAGC
TGCCGCCGCATGCGCATCGACCCCTACCTAAGCCCCTGCACCAAGGTGAAGA
GCAAGTGGATCAAGGAGCTGCACATCAAGCCCGAGACTCTGAAGCTGATCGA
GGAGAAGGTGGGCAAGAGCCTGGAGGACATGGGCACCGGCGAAAAGTTCCT
GAACCGCACCGCCATGGCCTGTGCCGTGCGCAGCCGGATCGATAAGTGGGAC
CTGATGAAGCTGCAGTCCTTCTGTAAGGCCAAGGATACCGTGTACAAGACCA
AGCGCCCCCCGACCGACTGGGAGCGCATCTTCACCTACCCCAAGAGCGACCG
CGGCCTGATCAGCAACATCTACAAGGAGCTGAAGAAGGTGGACCTGCGCAA
GAGCAACAACCCGCTGAAGAAGTGGGGCTCCGAGCTGAACAAGGAGTTCTC
CCCCGAGGAGTACCGCATGGCCGAGAAGCACCTGAAGAAGTGCAGCACCAG
CCTGATCATCCGCGAGATGCAGATCAAGACCACCCTGCGCTTCCACCTGACC
CCCGTGCGGATGGCCAAGATCAAGAACAGCGGCGACTCGCGATGCTGGCGG
GGCTGCGGCGAGCGCGGCACCCTGCTGCACTGCTGGTGGGACTGTCGCCTGG
TCCAGCCCCTGTGGAAGAGCGTGTGGCGGTTCCTGCGGAAGCTGGACATCGT
GCTGCCCGAGGACCCCGCTATCCCCCTGCTGGGCATCTACCCTGAGGAGGCC
CCCACCGGCAAGAAGGACACCTGCAGTACCATGTTCATCGCCGCTCTGTTCA
TCATCGCCCGCAACTGGAAGGAGCCCCGCTGCCCCAGCACCGAGGAGTGGAT
TCAGAAGATGTGGTACATCTACACCATGGAGTACTACAGCGCCATCAAGAAG
AACGAGTTCATGAAGTTCCTGGCCAAGTGGATGGACCTGGAGAGCATCATCC
TGAGCGAGGTGACCCAGAGCCAGCGCAACAGCCACAACATGTACAGCCTGA
TCAGCGGCTACTAG
```

FIG. 7
SEQ ID NO: 2

ATGGCCAAGGGCAAGCGCCGCAACCTGACCAACCGCAACCAGGACCACAGC
CCCAGCCCCGAGCCCAGCACCCCCACCAGCCCCAGCCCCGGCAACCCCAACA
CCCCCGAGAACCTGGACCTGGACCTGAAGGCCTACCTGATGATGATGGTGGA
GGACATCAAGAAGGACTTCAACAAGAGCCTGAAGGAGATCCAGGAGAACAC
CGCCAAGGAGCTGCAGGTGCTGAAGGAGAAGCAGGAGAACACCATCAAGCA
GGTGGAGGTGCTGACCGAGAAGGAGGAGAAGACCTACAAGCAGGTGATGGA
GATGAACAAGACCATCCTGGACCTGAAGCGCGAGGTCGACACCATCAAGAA
GACCCAGAGCGAGGCCACCCTGGAGATCGAGACCCTGGGCAAGAAGAGCGG
CACCATCGACCTGAGCATCAGCAACCGCATCCAGGAGATGGAGGAGCGCATC
AGCGGCGCCGAGGACAGCATCGAGAACATCGGCACCACCATCAAGGAGAAC
GGCAAGTGCAAGAAGATCCTGACCCAGAACATCCAGGAGATCCAGGACACC
ATCCGCCGCCCCAACGTGCGCATCATCGGCGTGGACGAGAACGAGGACTTCC
AGCTGAAGGGCCCCGCCAACATCTTCAACAAGATCATCGAGGAGAACTTCCC
CAACCTGAAGAACGAGATGCACATGAACATCCAGGAGGCCTACCGCACCCCC
AACCGCCTGGACCAGAAGCGCAACAGCTCTAGACACATCATCATCCGCACCA
GCAACGCCCTGAACAAGGACCGCATCCTGAAGGCCGTGCGCGAGAAGGGCC
AGGTGACCTACAAGGGCAAGCCCATCCGCATCACCCCCGACTTCAGCCCCGA
GACCATGAAGGCCCGCCGCGCCTGGACCGACGTGATCCAGACCCTGCGCGAG
CACAAGCTGCAGCCCCGCCTGCTGTACCCCGCCAAGCTGAGCATCATCATCG
AGGGCGAGACCAAGGTGTTCCACGACAAGACCAAGTTCACCCACTACCTGAG
CACCAACCCCGCCCTGCAGCGCATCATCACCGAGAAGAACCAGTACAAGAAC
GGCAACAACGCCCTGGAGAAGACCCGCCGCTAA

FIG. 8

SEQ ID NO: 3

ATGACCGGCAGCAACAGCCACATCACCATCCTGACCCTGAACATCAACGGCC
TGAACAGCGCCATCAAGCGCCACCGCCTGGCCAGCTGGATCAAGAGCCAGG
ACCCCAGCGTGTGCTGCATCCAGGAGACCCACCTGACCTGCCGCGACACCCA
CCGCCTGAAGATCAAGGGCTGGCGCAAGATCTACCAGGCCAACGGCAAGCA
GAAGAAGGCCGGCGTGGCCATCCTGGTGAGCGACAAGACCGACTTCAAGCC
CACCAAGATCAAGCGCGACAAGGAGGGCCACTACATCATGGTGAAGGGCAG
CATCCAGCAGGAGGAGCTGACCATCCTGAACATCTACGCCCCCAACACCGGT
GCCCCCCGCTTCATCAAGCAGGTGCTGAGCGACCTGCAGCGCGACCTGGACA
GCCACACCCTGATCATGGGCGACTTCAACACCCCCTGAGCACCCTGGACCG
CAGCACCCGCCAGAAGGTGAACAAGGACACCCAGGAGCTGAACAGCGCCCT
GCACCAGGCCGACCTGATCGACATCTACCGCACCCTGCACCCCAAGAGCACC
GAGTACACCTTCTTCAGCGCCCCCCACCACACCTACAGCAAGATCGACCACA
TCGTGGGCAGCAAGGCCCTGCTGAGCAAGTGCAAGCGCACCGAGATCATCAC
CAACTACCTGAGCGACCACAGCGCCATCAAGCTGGAGCTGCGCATCAAGAAC
CTGACCCAGAGCCGCAGCACCACCTGGAAGCTGAACAACCTGCTGCTGAACG
ACTACTGGGTGCACAACGAGATGAAGGCCGAGATCAAGATGTTCTTCGAAAC
CAACGAGAACAAGGACACCACCTACCAGAACCTGTGGGACGCCTTCAAGGC
CGTGTGCCGCGGCAAGTTCATCGCCCTGAACGCCTACAAGCGCAAGCAGGAG
CGCAGCAAGATCGACACCCTGACCAGCCAGCTGAAGGAGCTGGAGAAGCAG
GAGCAGACCCACAGCAAGGCCAGCCGCCGCCAGGAGATCACCAAGATCCGC
GCCGAGCTGAAGGAGATCGAGACCCAGAAGACCCTGCAGAAGATCAACGAG
TCGCGAAGCTGGTTCTTCGAGCGCATCAACAAGATCGACCGCCCCCTGGCCC
GCCTGATCAAGAAGAAGCGCGAGAAGAACCAGATCGACACCATCAAGAACG
ACAAGGGCGACATCACCACCGACCCCACCGAGATCCAGACCACCATCCGCGA
GTACTACAAGCACCTGTACGCCAACAAGCTGGAGAACCTGGAGGAGATGGA
CACCTTCCTGGACACCTACACCCTGCCCCGCCTGAACCAGGAGGAGGTGGAG
AGCCTGAACCGCCCCATCACCGGCAGCGAGATCGTGGCCATCATCAACAGCC
TGCCCACCAAGAAGAGCCCCGGCCCCGACGGCTTCACCGCCGAGTTCTACCA
GCGCTACAAGGAGGAGCTGGTGCCCTTCCTGCTGAAGCTGTTCCAGAGCATC
GAGAAGGAGGGCATCCTGCCCAACAGCTTCTACGAGGCCAGCATCATCCTGA
TCCCCAAGCCCGGCCGCGACACCACCAAGAAGGAGAACTTCCGCCCCATCAG
CCTGATGAACATCGACGCCAAGATCCTGAACAAGATCCTGGCCAACCGCATC
CAGCAGCACATCAAGAAGCTGATCCACCACGACCAGGTGGGCTTCATCCCCG
GGATGCAGGGCTGGTTCAACATCCGCAAGAGCATCAACGTGATCCAGCACAT
CAACCGCGCCAAGGACAAGAACCACATGATCATCAGCATCGACGCCGAGAA
GGCCTTCGACAAGATCCAGCAGCCCTTCATGCTGAAGACCCTGAACAAGCTG
GGCATCGACGGCACCTACTTCAAGATCATCCGCGCCATCTACGACAAGCCCA
CCGCCAACATCATCCTGAACGGCCAGAAGCTGGAGGCCTTCCCCCTGAAGAC

FIG. 8 (continued)

CGGCACGCGTCAGGGCTGCCCCCTGAGCCCCCTGCTGTTCAACATCGTGCTG
GAGGTGCTGGCCCGCGCCATCCGCCAGGAGAAGGAGATCAAGGGCATCCAG
CTGGGCAAGGAGGAGGTGAAGCTGAGCCTGTTCGCCGACGACATGATCGTGT
ACCTGGAGAACCCCATCGTGAGCGCCCAGAACCTGCTGAAGCTGATCAGCAA
CTTCAGCAAGGTGAGCGGCTACAAGATCAACGTGCAGAAGAGCCAGGCCTTC
CTGTACACCAACAACCGCCAGACCGAGAGCCAGATCATGGGCGAGCTGCCCT
TCACCATCGCTAGCAAGCGCATCAAGTACCTGGGCATCCAGCTGACCCGCGA
CGTGAAGGACCTGTTCAAGGAGAACTACAAGCCCCTGCTGAAGGAGATCAAG
GAGGAGACCAACAAGTGGAAGAACATCCCCTGCAGCTGGGTGGGCCGCATC
AACATCGTGAAGATGGCCATCCTGCCCAAGGTGATCTACCGCTTCAACGCCA
TCCCCATCAAGCTGCCCATGACCTTCTTCACCGAGCTGGAGAAGACCACCCT
GAAGTTCATCTGGAACCAGAAGCGCGCCCGCATCGCCAAGAGCATCCTGAGC
CAGAAGAACAAGGCCGGCGGCATCACCCTGCCCGACTTCAAGCTGTACTACA
AGGCCACCGTGACCAAGACCGCCTGGTACTGGTACCAGAACCGCGATATCGA
CCAGTGGAACCGCACCGAGCCCAGCGAGATCATGCCCCACATCTACAACTAC
CTGATCTTCGACAAGCCCGAGAAGAACAAGCAGTGGGGCAAGGACAGCCTG
TTCAACAAGTGGTGCTGGGAGAACTGGCTGGCCATCTGCCGCAAGCTGAAGC
TGGACCCCTTCCTGACCCCCTACACCAAGATCAACAGCCGCTGGATCAAGGA
CCTGAACGTGAAGCCCAAGACCATCAAGACCCTGGAGGAGAACCTGGGCAT
CACCATCCAGGACATCGGCGTGGGCAAGGACTTCATGAGCAAGACCCCCAAG
GCCATGGCCACCAAGGACAAGATCGACAAGTGGGACCTGATCAAGCTGAAG
AGCTTCTGCACCGCCAAGGAGACCACCATCCGCGTGAACCGCCAGCCCACCA
CCTGGGAGAAGATCTTCGCCACCTACAGCAGCGACAAGGGCCTGATCAGCCG
CATCTACAACGAGCTGAAGCAGATCTACAAGAAGAAGACCAACAACCCCAT
CAAGAAGTGGGCCAAGGACATGAACCGCCACTTCAGCAAGGAGGACATCTA
CGCCGCCAAGAAGCATATGAAGAAGTGCAGCAGCAGCCTGGCCATCCGCGA
GATGCAGATCAAGACCACCATGCGCTACCACCTGACCCCCGTGCGCATGGCC
ATCATCAAGAAGAGCGGCAACAACCGCTGCTGGCGCGGCTGCGGCGAGATC
GGCACCCTGCTGCACTGCTGGTGGGACTGCAAGCTGGTGCAGCCCCTGTGGA
AGAGCGTGTGGCGCTTCCTGCGCGACCTGGAGCTGGAGATCCCCTTCGACCC
CGCCATCCCCCTGCTGGGCATCTACCCCAACGAGTACAAGAGCTGCTGCTAC
AAGGACACCTGCACCCGCATGTTCATCGCCGCCCTGTTCACCATCGCCAAGA
CCTGGAACCAGCCCAAGTGCCCCACCATGATCGATTGGATCAAGAAGATGTG
GCACATCTACACCATGGAGTACTACGCCGCCATCAAGAACGACGAGTTCATC
AGCTTCGTGGGCACCTGGATGAAGCTGGAGACCATCATCCTGAGCAAGCTGA
GCCAGGAGCAGAAGACCAAGCACCGCATCTTCAGCCTGATCGGCGGCAACTG
A

FIG. 9

SEQ ID NO: 4

ATGGGCAAGAAGCAGAACCGCAAGACCGGCAACAGCAAGACCCAGAGCGCC
AGCCCCCCCCCCAAGGAGCGCAGCAGCAGCCCCGCCACCGAGCAGAGCTGG
ATGGAGAACGACTTCGACGAGCTGCGCGAGGAGGGCTTCCGCCGCAGCAACT
ACAGCGAGCTGCGCGAGGACATCCAGACCAAGGGCAAGGAGGTGGAGAACT
TCGAGAAGAACCTGGAGGAGTGCATCACCCGCATCACCAACACCGAGAAGT
GCCTGAAGGAGCTGATGGAGCTGAAGACCAAGGCCCGCGAGCTGCGCGAGG
AGTGCCGCAGCCTGCGCAGCCGCTGCGACCAATTGGAGGAGCGCGTGAGCGC
CATGGAGGACGAGATGAACGAGATGAAGCGCGAGGGCAAGTTCCGCGAGAA
GCGCATCAAGCGCAACGAGCAGAGCCTGCAGGAGATCTGGGACTACGTGAA
GCGCCCCAACCTGCGCCTGATCGGCGTGCCCGAGAGCGACGTGGAGAACGGC
ACCAAGCTGGAGAACACCCTGCAGGACATCATCCAGGAGAACTTCCCCAACC
TGGCCCGCCAGGCCAACGTGCAGATCCAGGAGATCCAGCGCACCCCCCAGCG
CTACAGCAGCCGCCGCGCCACCCCCGCCACATCATCGTGCGCTTCACCAAG
GTGGAGATGAAGGAGAAGATGCTGCGCGCCGCCCGCGAGAAGGGCCGCGTG
ACCCTGAAGGGCAAGCCCATCCGTCTCACCGCCGACCTGAGCGCCGAGACCC
TGCAGGCCCGCCGCGAGTGGGGCCCCATCTTCAACATCCTGAAGGAGAAGAA
CTTCCAGCCCCGCATCAGCTACCCCGCCAAGCTGAGCTTCATCAGCGAGGGC
GAGATCAAGTACTTCATCGACAAGCAGATGCTGCGCGACTTCGTGACCACCC
GCCCCGCCCTGAAGGAGCTGCTGAAGGAGGCCCTGAACATGGAGCGCAACA
ACCGCTACCAGCCCCTGCAGAACCACGCCAAGATGTAA

FIG. 10

| oligo name | sequence | use | SEQ ID NO |
|---|---|---|---|
| JB4057 | GCCGGTGGTGCAGATGAACTTCAGGGTCAGCTTGCCGTAGGTGG | GFP probe | 5 |
| JB4059 | CAAGCGGCCGGAGAACCTGCGTGCAATCCATCTTGTTCAATCAT | GFP plasmid neo probe | 6 |
| JB4541 | CCGCTTGGGTGGAGAGAGGCTATTCGGCTATGACTGGGCACAACAGACAATCGGGTGCTCTG | transposition plasmid neo probe | 7 |
| JB6341 | CGCAGCTATTTACCCGCAGGACATATCCACGCCCTCCTACATCGAAGCTGAAAGCACGAG | hygro probe | 8 |
| JB6466 | GGAGTTAGGGGCGGGACTATGGTTGCT | inverted PCR round 1 | 9 |
| JB6467 | ATCAGGACATAGCGTTGGCTACCCGTGA | inverted PCR round 1 | 10 |
| JB6468 | GCCTGGGGACTTTCCACACCCTAACTGA | inverted PCR round 2 | 11 |
| JB6469 | CGAGTTCTTCTGAGGGGATCGGCAATAA | inverted PCR round 2 | 12 |
| JB3529 | AAAAAAAAAAAAAAAAAAAAAAAT | L1 insertion sequencing primer | 13 |
| JB3530 | AAAAAAAAAAAAAAAAAAAAAAAC | L1 insertion sequencing primer | 14 |
| JB3531 | AAAAAAAAAAAAAAAAAAAAAAAG | L1 insertion sequencing primer | 15 |
| JB6627 | GCGAATTCTTCTACTAGTTACAACTTGTTTTCAGTCAATGA | 5' PCR primer smL 1 insertion #8 | 16 |
| JB6628 | GCGAATTCATGAGAGAATCCAGGACAGGCCATAATACCC | 3' PCR primer smL 1 insertion #8 | 17 |
| JB6629 | CCGCTCGAGTGGCAGAGAGTTAAAGTCCTGTAATGGTTG | 5' PCR primer smL 1 insertion #10 | 18 |
| JB6630 | CCGCTCGAGGCGTGTTTCCCAGGGTAATGAGTCATCTTG | 3' PCR primer smL 1 insertion #10 | 19 |
| JB6631 | GCGAATTCTTTAGATTTATGGAAAATCAGGCTGCTTAC | 5' PCR primer smL 1 insertion #13 | 20 |
| JB6632 | GCGAATTCTGGGCCCCCAAAATCCCTTTT | 3' PCR primer smL 1 insertion #13 | 21 |
| JB6633 | GCGAATTCAGCAAAATCCATCTCAAAAACAAACA | 5' PCR primer smL 1 insertion #14 | 22 |
| JB6634 | GCGAATTCAAATGGACAGCTTTCCTGTCTCTGGCTCTC | 3' PCR primer smL 1 insertion #14 | 23 |
| JB6635 | GCGAATTCTGGAATTTAAACCTTCAAAGAATTCCTCCCACT | 5' PCR primer smL 1 insertion #18 | 24 |
| JB6636 | GCGAATTCGACGGAAGGGTATGCCTTTTCCTTCATCAC | 3' PCR primer smL 1 insertion #18 | 25 |
| JB6637 | GCGAATTCTACAGGTGTGAGGCACAGTGCCTGTTTCT | 5' PCR primer smL 1 insertion #23 | 26 |
| JB6638 | GCGAATTCCCTAAGTTCATTCTGGAATGGCTGAAAC | 3' PCR primer smL 1 insertion #23 | 27 |
| smORF2-1 | AGAATGCCCCCCCTGACCACCAAGATCACCGGCAGCAACACTACTTCAGCCTGATCAGCCTG | smORF2 gene synthesis | 28 |
| smORF2-2 | CTTGATGGGGCTGTTCAGGCCGTTGATGTTCAGGCTGATCAGGCTGAAGTAGTTGTTGCT | smORF2 gene synthesis | 29 |

FIG. 10 (continued)

| | | | |
|---|---|---|---|
| smORF2-3 | AACATCAACGGCTGAACAGCCCATCAAGCGGCACGGCCTGACCAACTGGCTGCACAAG | smORF2 gene synthesis | 30 |
| smORF2-4 | CTCCTGGAGGCAACAGAAGGTGGGGTCCTGCTTGTGCAGCCAGTTGGTCAGGCGGTGCCG | smORF2 gene synthesis | 31 |
| smORF2-5 | CAGGACCCACCTTCTGTTGCCTCCAGGAGACCCACCTGCGGGAGAAGGACCGGCACTAC | smORF2 gene synthesis | 32 |
| smORF2-6 | AAAGATGGTCTTCCAGCCCTTCATCCGCAGGTAGTGCCGGTCCTTCTCGGCAGGTGGGT | smORF2 gene synthesis | 33 |
| smORF2-7 | CTGCGGATGAAGGGCTGGAAGAACCATCTTTCAGGCCAACGGCATGAAGAAGCAGGCTGGC | smORF2 gene synthesis | 34 |
| smORF2-8 | GTCGATCTTGTCGCTGATCAGGATGGCCACGCAGCCTGCTTCTTCATGCCGTTGGCCTG | smORF2 gene synthesis | 35 |
| smORF2-9 | GTGGCCATCCTGATCAGCGACAAGATCGACTTCCAGCCCAAGGTGATCAAGAAGGACAAG | smORF2 gene synthesis | 36 |
| smORF2-10 | CTTGCCCTTGATCAGGATGAAGTGGCCCTCCTTGTCCTTCTTGATCACCTTGGGCTGGAA | smORF2 gene synthesis | 37 |
| smORF2-11 | GAGGGCCACTTCATCCTGATCAAGGGCAAGATCCTGCAGGAGGAGCTGAGCATTCTGAAAC | smORF2 gene synthesis | 38 |
| smORF2-12 | GGTGGCGGCGGCTGTTGGGGGCGTAGATGTTCAGAATGCTCAGCTCCTCCTGCAGGAT | smORF2 gene synthesis | 39 |
| smORF2-13 | ATCTACGGCCCCCAACACCCGGCGCCCACCTTCACCAAGGAGACCCTCGTGAAGCTGAAG | smORF2 gene synthesis | 40 |
| smORF2-14 | GACGATGGTGTGGGGAGCGATGTGGGGCTTCAGCTTCGCGAGTTCACGAGGGTCTCCTTGGTGAA | smORF2 gene synthesis | 41 |
| smORF2-15 | GCCCACATCGCTCCCCACACATCGTCGGCGACTTCAACACCCCCTGAGC | smORF2 gene synthesis | 42 |
| smORF2-16 | AAGATCTGTCCATGGGGCTCAGGGGGTGTTGAAGTCGCC | smORF2 gene synthesis | 43 |
| smORF2-17 | CAGATCTTGGAAGCAGAAGCTGAACCGCGACACCCTGAAGCTGACCGAGGTGATGAAG | smORF2 gene synthesis | 44 |
| smORF2-18 | GGTGCGGTAGATGTCGGTCAGGTCCATCTGCTTCATCACCTCGGTCAGCTTCAGGGTGTC | smORF2 gene synthesis | 45 |
| smORF2-19 | CAGATGGACCTGACCGACATCTACCGCACCTTCTACCCCAAGACCAAGGGCTACACCTTC | smORF2 gene synthesis | 46 |
| smORF2-20 | CTTGCTGAAGGTGCCGTGGGGAGCGCACCTTCAGCAAGATCGAGAAGGTGTAGCCCTTGGGTCTTGGGGTAGAA | smORF2 gene synthesis | 47 |
| smORF2-21 | TTCAGCGCTCCCCACGGCACCTTCAGCAAGATCCAGCCACATCGTGGCCACAAGAGCGGG | smORF2 gene synthesis | 48 |
| smORF2-22 | CACGATCTCGATGTTCTTCAGCGGTTCAGCCGCTTCAGCCGGGATGATGTGGTCGAT | smORF2 gene synthesis | 49 |
| smORF2-23 | CTGAACCGGCTGAAGAACATCGAGATCGTGCCCTGCGATCCTGAGCGACCACCATGCCCTG | smORF2 gene synthesis | 50 |
| smORF2-24 | GTTGTTAATCTTGTTGTTGAAGATCAGGCGGCAGGGCATGGTGGTCGCTCAGGATGCAGGG | smORF2 gene synthesis | 51 |
| smORF2-25 | CGCCTGATCTTCAACAACAAGATTAACAACCGAAGCCAAGCCACCTTCACCTGGAAGCTGAAC | smORF2 gene synthesis | 52 |
| smORF2-26 | CTTCACCAGGGTGTCGTTCAGCAGGGTGTTGTTCAGCTTCCAGGTGAAGGTGGGCTTGCG | smORF2 gene synthesis | 53 |
| smORF2-27 | AACACCCTGCTGAACGACACCCTGGTGAAGGAAGGCATCAAGAAGGAGATCAAGGACTTC | smORF2 gene synthesis | 54 |
| smORF2-28 | GGTGGTGGCCTCGTTCTCGTTGAACTCCAGGAAGTCCTTGATCTCCTTCTTGATGCCTTC | smORF2 gene synthesis | 55 |

FIG. 10 (continued)

| | | | |
|---|---|---|---|
| smORF2-29 | CTGGAGTTCAACGAGAACGAGGCCCACCACCTACCCTAACCTGTGGGACACCATGAAGGCC | smORF2 gene synthesis | 56 |
| smORF2-30 | GCTCATGGCGATCAGCTTGCCCCGCAGGAAGGCCTTCATGGTGTCCCACAGGTTAGGGTA | smORF2 gene synthesis | 57 |
| smORF2-31 | TTCCTGCGGGGCAAGCTGATCGCCATGAGCGCCTTCAAGAAGAAGCGGAGCGCGCCCAC | smORF2 gene synthesis | 58 |
| smORF2-32 | CTACTAGTGTGGGGCCGGCTCCCGCTTCTTCTTGAAGGC | smORF2 gene synthesis | 59 |
| smORF2-33 | CACTAGTAGCCTGACCACCCACCTGAAGGCCCTGGAGAAGAAGGAGGCTAACTCCCCAA | smORF2 gene synthesis | 60 |
| smORF2-34 | CAGCTTGATGATCTCCTGCCGCCGGGAGCGCTTGGGGGGAGTTAGCCTCCTTCTTCTCAG | smORF2 gene synthesis | 61 |
| smORF2-35 | CGCTCCCGGCGGCAGGAGATCATCAAGCTGCGCGGCGAGATCAACCAGGTGGAGACCCGG | smORF2 gene synthesis | 62 |
| smORF2-36 | CCGGGTCTGGTTGATCCGTTGGATGGTGCGCGCCGGGTCTCCACCTGGTTGATCTCGCCGCG | smORF2 gene synthesis | 63 |
| smORF2-37 | CGCACCATCCAACGATCAACCAGACCCGTCTTGGTTCTTCGAGAAGATCAACAAGATC | smORF2 gene synthesis | 64 |
| smORF2-38 | GCCCTTGGTCAGGCGAGCCAGGGGCTTGTCGATCTTGTTGATCTTCTCGAAGAACCAAGA | smORF2 gene synthesis | 65 |
| smORF2-39 | GACAAGCCCCTGGCTCGCCTGACCAAGGGCCACCGGCGACAAGATCCTGATCAACAAGATC | smORF2 gene synthesis | 66 |
| smORF2-40 | GTCGGTGGTGATGTGCGCCTTCTCGTTGCGGATCTTGTTGATCAGGATCTTGTCGCGGTG | smORF2 gene synthesis | 67 |
| smORF2-41 | CGCAACGAGAAGGGGCGACATCACCACCCGAGGAGATCCAGAACACCATCCGGCAGC | smORF2 gene synthesis | 68 |
| smORF2-42 | CAGCTTGGTGCTGTACAGGGCGCTTGTAGAAGCTGCGGATGGTGTTCTGGATCTCCTCGGG | smORF2 gene synthesis | 69 |
| smORF2-43 | TTCTACAAGCGCCTGTACAGCACCAAGCTGGAGAACCTGGACAGAGATGGACAAGTTCCTG | smORF2 gene synthesis | 70 |
| smORF2-44 | CTGGTTCAGCTTGGGCACCTGAGGGTCCAGGAACTTGTCCATCTCGTCCAGGTTCTC | smORF2 gene synthesis | 71 |
| smORF2-45 | GACCGCTATCAGGTTGCCCAAGCTGAACCAGGAGGACCAGGTGGACCTGCTGAACAGCCCCATC | smORF2 gene synthesis | 72 |
| smORF2-46 | GTTGATCACGGCCTCGATTTCCTTGGGGGAGATGGGGCTGTTCAGCAGGTCCACCTGGTC | smORF2 gene synthesis | 73 |
| smORF2-47 | TCCCCAAGGAAATCGAGGCCGTGATCAACAGCCTGCCCGCCAAGAAGAGCCCGGCCCC | smORF2 gene synthesis | 74 |
| smORF2-48 | GGTCTGGTAGAACTCAGCGCTGAAGCGCGTCGGGGCTCTTCTTGGCGGGCAGGCT | smORF2 gene synthesis | 75 |
| smORF2-49 | GACGGCTTCAGCGCTGAGTTCTACCAGACCTTCAAGGAGACCTGACCCCGTGCTGCAC | smORF2 gene synthesis | 76 |
| smORF2-50 | AAAAGCTTGTGCAGCACGGGGGTCAGGTCCTCCTTGAA | smORF2 gene synthesis | 77 |
| smORF2-51 | CAAGCTTTTCCACAAGATCGAGGTCGAGGCCATCCTCCCCAACAGCTTCTACGAGGCCAC | smORF2 gene synthesis | 78 |
| smORF2-52 | GTCCTTCTGGGCGCTTGGGGATCAGGGTGATCAGGGTGTAGTTGGCCTCGTAGAACCTGTTGGGGAGGAT | smORF2 gene synthesis | 79 |
| smORF2-53 | ATCACCCTGATCCCCAAGCCCCAGAAGGAGACCCCACCAAGATCGAGAACTTCCGCCCATC | smORF2 gene synthesis | 80 |
| smORF2-54 | CAGGATCTTGGCGTCGATGTTCATCAGCGTGATGGGCGGAAGTTCTCGATCTTGGTGGG | smORF2 gene synthesis | 81 |

FIG. 10 (continued)

| | | | |
|---|---|---|---|
| smORF2-55 | AGCCTGATGAACATCGACGCCAAGATCCTGAACAAGATCCTCGCCAACCGCATCCAGGAG | smORF2 gene synthesis | 82 |
| smORF2-56 | CTGGTCAGGGTGGATGGCCTTGATGTGCTCCTGGATGCCGGTTGGCGAGGATCTTGTT | smORF2 gene synthesis | 83 |
| smORF2-57 | CACATCAAGGCCATCATCCACCCTGACCAGGTCGGCTTCATCCCCGGCATGCAGGGCTGG | smORF2 gene synthesis | 84 |
| smORF2-58 | GATCACGTTGATGCTCTTGCGGATGTTGAACCAGCCCTGCATGCCGGGGATGAAGCCGAC | smORF2 gene synthesis | 85 |
| smORF2-59 | TTCAACATCCGCAAGAGCATCAACGTGATCCACTACATCAACAAGCTGAAGGACAAGAAAC | smORF2 gene synthesis | 86 |
| smORF2-60 | CTTCTCGGCGTCCAGGCTGATGATCATGTGGTTCTTGTCCTTCAGCTTGTTGATGTAGTG | smORF2 gene synthesis | 87 |
| smORF2-61 | CACATGATCATCAGCCTGGACGCCGAGAAGGCCTTCGACAAGATCCAGCACCCCTTCATG | smORF2 gene synthesis | 88 |
| smORF2-62 | CTGAATGCCCGCTGCGCTCCAGGACCTTGATCATGAAGGGGTGCTGGATCTTGTCGAAGGC | smORF2 gene synthesis | 89 |
| smORF2-63 | ATCAAGGTCCTGGAGCGCAGCGGCATTCAGGGCCAGTACCTCAACATGATCAAGGCCATC | smORF2 gene synthesis | 90 |
| smORF2-64 | CACCTTGATGTTGGCGACGGGCTTGCTGTAGATGGCCTTGATCATGTTGAGGTACTGGCC | smORF2 gene synthesis | 91 |
| smORF2-65 | TACAGCAACCCGTCGGCCAACATCAAGGTGAACGGGAGAAGGTGGAGGCCATCCCTCTG | smORF2 gene synthesis | 92 |
| smORF2-66 | TGACGCGTGCCGCTCTTCAGAGGGATGGCCTCCAGCTTCTCCCGTT | smORF2 gene synthesis | 93 |
| smORF2-67 | GCACGCGTCAGGGCGTGTCCTCTGTCCCCGTCAGCTGTTCAACATCGTGCTGGAG | smORF2 gene synthesis | 94 |
| smORF2-68 | CTTCTGCTGCCGGCGATAGCGGCGGCCAGCACCTCCAGCACGATGTTGAACAGGTAGGGGGA | smORF2 gene synthesis | 95 |
| smORF2-69 | GTGCTGGCCCGGCTATCCGGCAGCAGAAGGAGATCAAGGGCATCCAGATCGGCAAGGAG | smORF2 gene synthesis | 96 |
| smORF2-70 | GTCGTCGGCGAACAGGCTGATCTTCACCTCCGCCGGATCTCCTGCCAGTCGGATGCCTTGATCTC | smORF2 gene synthesis | 97 |
| smORF2-71 | GAGGTGAAGATCAGCCTGCTTCGCCGACGACATGATCGTTACATCAGCGACCCCAAGAAC | smORF2 gene synthesis | 98 |
| smORF2-72 | GTTGATCAGGTTCAGGAGCTCGGGTTGCTGTTCTTGGGGTGCTGATGTACACGATCAT | smORF2 gene synthesis | 99 |
| smORF2-73 | AGCAACCGCGAGCTCCTGAACCTGATCAACAGCTTCGGCGAGGTGGCTGGCTACAAGATC | smORF2 gene synthesis | 100 |
| smORF2-74 | GTACAGGAAGGCCATGCCTTCTTGTTGCTTGTTGATCTTGTACACCAAGCAGCCACCTCGCCGAAGCT | smORF2 gene synthesis | 101 |
| smORF2-75 | AACAGCAACAAGAGACATGGCCTTCGTGCCTTCCTGTACAACAAGAACAAGCCAGGCCGAGAAGGAGATC | smORF2 gene synthesis | 102 |
| smORF2-76 | GGTGGCGATGCTGAAGGGGGTGGTCTCGCGGATCTCCTTCGGCCTGTTCTTGGT | smORF2 gene synthesis | 103 |
| smORF2-77 | CGGGAGACCACCCCCTTCAGCATCGCCAACATCAAGTACCTGGGCGTGACCCTG | smORF2 gene synthesis | 104 |
| smORF2-78 | CTTGTCGTACAGGTCCTTCACCTCCTTGGTCAGGAAGAACTTCAGGGTCACGCCCAGGTACTTGATGTTGTT | smORF2 gene synthesis | 105 |
| smORF2-79 | ACCAAGGAGGTGAAGGACCTGTACGACAAGAACTTCAAGAGCCTGAAGAAGGAGATCAAG | smORF2 gene synthesis | 106 |
| smORF2-80 | GGGCAGGTCCTTCCAGCGGCGGCCAGGTCCTTGATCTCCTTCTTCAGGCTCTTCTTGAAGTT | smORF2 gene synthesis | 107 |

FIG. 10 (continued)

| | | | |
|---|---|---|---|
| smORF2-81 | GAGGACCTGCGCGCTGGAAGGACCTGCCCTGCAGCTGATCGGCCGCACCAACATCGTG | smORF2 gene synthesis | 108 |
| smORF2-82 | GTAGATAGCCTTGGGCAGGATGGCCATCTTCACGATGTTGGTGCGGCCGATCAGCTGCA | smORF2 gene synthesis | 109 |
| smORF2-83 | AAGATGGCCATCCTGCCCAAGGCTATCTCAAGGCTTCAAACGCCATCCCATCAAGATCCCC | smORF2 gene synthesis | 110 |
| smORF2-84 | CCCTCGAGCTCGTTGAAGAACTGGGTGGGATCTTGATGGGGATGGCGTTGAAGCG | smORF2 gene synthesis | 111 |
| smORF2-85 | AGCTCGAGGGCGGCCATCTGCAAGTTCATCTGGAACAACAAGAAG | smORF2 gene synthesis | 112 |
| smORF2-86 | GTCCTTCAGCAGGGTCTTGGCGATGCGGGGCTTCTTGTTGTTCCAGATGAACTTGCAGAT | smORF2 gene synthesis | 113 |
| smORF2-87 | CCCCGCATCGCCAAGACCCTGCTGAAGGACAAGCGCACAGTGGGGGGGATCACCATGCCC | smORF2 gene synthesis | 114 |
| smORF2-88 | CACGATGGCGCGGTAGTACAGCTTCAGGTCGGGCATGGTGATCCCCCACTGGTGCGCTT | smORF2 gene synthesis | 115 |
| smORF2-89 | GACCTGAAGCTGTACTACCGGCGACCATCGTGATCAAGACCGCTGGTACTGGTACCGGCGAC | smORF2 gene synthesis | 116 |
| smORF2-90 | CTCGATGCGGTTCCACTGGTCCACCTGGGCGTCGCGGTACCAGTACCAGGCGGTCTTGAT | smORF2 gene synthesis | 117 |
| smORF2-91 | CGCCAGGTGGACCAGTGGAACCGCATCGAGGACCCGAGATGAACCCCACACCTACGGC | smORF2 gene synthesis | 118 |
| smORF2-92 | GGTCTTGGCGCCCTTGTCGAAGATCAGGTGGCCGTAGGTGTGGGGGTTCATCTCGGGGTC | smORF2 gene synthesis | 119 |
| smORF2-93 | CACCTGATCTTCGACAAGGGGCGCCAAGACCATCCAGTGGAAGAAGGACAGCATCTTCAAC | smORF2 gene synthesis | 120 |
| smORF2-94 | GCTCAGCAGCCAGTTGTGCCAGAACTGGCTGCTGAGCTGCCGGCCCATGCGGTCCTTCTTCCACTGGAT | smORF2 gene synthesis | 121 |
| smORF2-95 | AACTGGTGCTGGCACAACTGGCTCTTGCAGGGGCTCAGGTCTGAGCTGCCCATGCGCATGCGCATGCCCTACCTG | smORF2 gene synthesis | 122 |
| smORF2-96 | CCACTTGCTCTTCACCTTGGTGCAGGGGCTCAGGTAGGGGTCGATGCGGCATGCGGCGGCA | smORF2 gene synthesis | 123 |
| smORF2-97 | AGCCCCTGCACCAAGGTGAAAGACCAAGGTGGATCAAGGAGCTGCACATCAAGCCCGAGACC | smORF2 gene synthesis | 124 |
| smORF2-98 | CTTGCCCACCTTCTCCTCGATCAGCTTCAGGGTCTCGGGCTTGATGTGCAGCTCCTTGAT | smORF2 gene synthesis | 125 |
| smORF2-99 | CTGAAGCTGATCGAGGAGAAGGTGGGCAAGAGCCTGGAGGACATGGGCACGGCGAGAAG | smORF2 gene synthesis | 126 |
| smORF2-100 | GGGCACAGGCCATGGCGGTGCGGTTCAGGAACTTCTCGCGGTGCCCATGTCCTCCAGGCT | smORF2 gene synthesis | 127 |
| smORF2-101 | TTCCTGAACCGCACGGCACTGCCCTGTGCCGTGCGGCAGCCGGATCGATAAGTGGGACCTG | smORF2 gene synthesis | 128 |
| smORF2-102 | CTTGGCCTTACAGAAGGACTGCAGCTTCATCAGGTCCCACTTATCGATCCGGCTGCGAC | smORF2 gene synthesis | 129 |
| smORF2-103 | ATGAAGCTGCAGTCCTTCTGTAAGGCCAAGATACCGTGTACAAGACCAAGCGCCCCCG | smORF2 gene synthesis | 130 |
| smORF2-104 | GGGGTAGGTGAAGATGCGCTCCCAGTGGTCGGTCGGGGGCGCTTGGTCTTGTACACGGTATC | smORF2 gene synthesis | 131 |
| smORF2-105 | ACCGACTGGGAGGCGCATCTTCACCTACCCCAAGAGCGACCGGCGCCTGATCAGCAACATC | smORF2 gene synthesis | 132 |
| smORF2-106 | GCGCAGGTCCACCTTCTTCAGCTCCTTGTAGATGTTGCTGATCAGGCCGGGGTCGCTCTT | smORF2 gene synthesis | 133 |

FIG. 10 (continued)

| | | | |
|---|---|---|---|
| smORF2-107 | TACAAGGAGCTGAAGAAGGTGGACCTGCGCAAGAGCAAGAACCCGCTGAAGAAGTGGGGC | smORF2 gene synthesis | 134 |
| smORF2-108 | CTCGGGGGAGAACTCCTTGTTCAGCTGGGAGCCCCACTTCTTCAGCGGGTTGTTGCTCTT | smORF2 gene synthesis | 135 |
| smORF2-109 | TCCGAGCTGAACAAGGAGTTCTCCCCCGGAGTACCGGAGAAGAAGCACCTGAAAG | smORF2 gene synthesis | 136 |
| smORF2-110 | CTCGCGGATGATCAGGCTGGTGCTGCACTTCTTCAGGTGCTTCTCGGCCATGCGGTACTC | smORF2 gene synthesis | 137 |
| smORF2-111 | AAGTGCAGCACCAGCTGATCATCCGGGAGATGCAGATCAAGACACCCTGCGCTTCCAC | smORF2 gene synthesis | 138 |
| smORF2-112 | CTTGATCTTGGCCATCCGCACGGGGTCAGGTGGAAGCGGCAGGGTGGTCTTGATCTGCAT | smORF2 gene synthesis | 139 |
| smORF2-113 | CTGACCCCGTGCGATGGCCAAGATCAAGAACAGCGGCGACTCGCGATGCTGCGGGGC | smORF2 gene synthesis | 140 |
| smORF2-114 | GCAGTGCAGCAGGGTGCCGGCCTCGCCGCACCCCAGCCATCGCGAGTCGCCGCTGTT | smORF2 gene synthesis | 141 |
| smORF2-115 | TGCGGGCGAGGCGCGGCACCCTGCTGCACTGCTGCGCCTGGTCCAGCCCCTG | smORF2 gene synthesis | 142 |
| smORF2-116 | CTTCCGCAGGAACCGGCCACACGCTCTTCCACAGGGGCTGGACCAGGCGACAGTCCCACCA | smORF2 gene synthesis | 143 |
| smORF2-117 | TGGAAGAGCGTGTGGCGGTTCCTGGGAAGCTGGACATCGTGCTGCCCGAGGACCCGCC | smORF2 gene synthesis | 144 |
| smORF2-118 | CTCCTCGGGGTAGATGCCAGCAGGGGATGGCGGGGTCCTCGGGCAGCAGCACGATGTCCAG | smORF2 gene synthesis | 145 |
| smORF2-119 | ATCCCCTGCTGGGCATCTACCCCGAGGAGGCCCCACCGGCAAGAAGGACACCTGCAGC | smORF2 gene synthesis | 146 |
| smORF2-120 | GATGATGAACAGGGCGGCGATGAACATGGTGCTGCAGGTGTCCTTCTTGCCGGTGGGGC | smORF2 gene synthesis | 147 |
| smORF2-121 | ACCATGTTCATCGCCGCCCTGCTTCATCATCGCCCGCAACTGGAAGGAGCCCGCTGCCCC | smORF2 gene synthesis | 148 |
| smORF2-122 | CCACATCTTCTGAATCCACTCCTCGGTGCTGGGGCAGCGGGGCTCCTTCCAGTTGCGGGC | smORF2 gene synthesis | 149 |
| smORF2-123 | AGCACCGAGGAGTGGATTCAGAAGATGTGGTACATCTACACCATGGAGTACTACAGCGCC | smORF2 gene synthesis | 150 |
| smORF2-124 | CAGGAACTTCATGAACTCGTTCTTCTTGATGGCGCTGTAGTACTCCATGGTGTAGATGTA | smORF2 gene synthesis | 151 |
| smORF2-125 | ATCAAGAAGAACCAGAGTTCATGAAGTTCCTGGCCAAGTGGATGGACCTGGAGAGCATCATC | smORF2 gene synthesis | 152 |
| smORF2-126 | GTTGCGCTGGCTCTGGGTCACCTCGCTCAGGATGATGCTCTCCAGGTCCATCCACTTGGC | smORF2 gene synthesis | 153 |
| smORF2-127 | CTGAGCGAGGTGACCCAGAGCCAGCCAACAGCCACAACATGTACAGCCTGATCAGCGGG | smORF2 gene synthesis | 154 |
| smORF2-128 | ATCGTGGGTATCACCGGTTTTGGGCTAGTACCCGGTGATCAGGCTGTACATGTTGTGGCT | smORF2 gene synthesis | 155 |
| smORF2-129 | TACTAGCCCAAAACCGGTGATACCCACGATATAAGATACAATTGCCTAAACACATGAAAC | smORF2 gene synthesis | 156 |
| smORF2-130 | TGTCCACACTTCAGTCTTCATTTTTCTTGAGTTTCATGTGTTTAGGCAATTGTATCTTAT | smORF2 gene synthesis | 157 |
| smORF2-131 | TCAAGAAAAATGAAGACTGAAGTGTGGACACTATGCCCCTCCTTAGAAGTGGGAACAAAA | smORF2 gene synthesis | 158 |
| smORF2-132 | ACTTTGTTTCTGTAACTCCTTCCATGGCTGTTTTGTTCCCAGTTCTAAGGAGGGGCATAG | smORF2 gene synthesis | 159 |

FIG. 10 (continued)

| | | | |
|---|---|---|---|
| smORF2-133 | CAGGCCATGGAAGGAGTTACAGAAACAAAGTTTGGAGCTGAGATGAAAGGAGGACCATGT | smORF2 gene synthesis | 160 |
| smORF2-134 | TGGGGTGGAACCCTGGATATGGCAGTCTCTACATGGTCCCTCCTTTCATCTCAGCTCCAA | smORF2 gene synthesis | 161 |
| smORF2-135 | AGAGACTGCCATATCCAGGGTTCCACCCCATAATCAGGATCCAAGCTCTGACACCATTGC | smORF2 gene synthesis | 162 |
| smORF2-136 | GGTCCTTTCGATAAAATCTTCCTAGTATATGCAATGGTGTCAGAGCTTGGATGCTGATTA | smORF2 gene synthesis | 163 |
| smORF2-137 | ATATACTAGGAAGATTTTATCGAAAGGACCCAGATGTAGCTGTCTCTTGTGAGACTATGC | smORF2 gene synthesis | 164 |
| smORF2-138 | AGCATCCACTTCTGTGTTTGCTAGGCCCCGGCATAGTCTCACAAGAGACAGGTACATCTG | smORF2 gene synthesis | 165 |
| smORF2-139 | CGGGGCCTAGCAAACACAGAAGTGGATGCTCACAGTCAGTCAATGGATCACAGGGGC | smORF2 gene synthesis | 166 |
| smORF2-140 | TGGGTACTTTCTCTAGCTCCTCCATTGAAAGCCCTGTGATCCATCCATTAGCTGACTGTG | smORF2 gene synthesis | 167 |
| smORF2-141 | TTTCAAATGGAGGAGCTAGAGAAAGTACCCAAGGAGCTAAAGGGATCTGCAACTCTATAGG | smORF2 gene synthesis | 168 |
| smORF2-142 | GGGTACTGGTTAACTCATCATAATGTGTTCCACCTATAGAGTTGCAGATCCCTTTAGCTCCT | smORF2 gene synthesis | 169 |
| smORF2-143 | TGGAACAACATTATGAGTTAACCAGTACCCCTGAGCTCTTGACGCTAGCTGCATATGTAT | smORF2 gene synthesis | 170 |
| smORF2-144 | TCCAGTGATGACCGACTAGGCCATCTTTTTGATACATATGCAGCTAGCGTCAAGAGCTCAG | smORF2 gene synthesis | 171 |
| smORF2-145 | CAAAAGATGGCCTAGTCGGTCATCACTGGAAAGAGAGGCCCATTGGACACGCAGACTTTG | smORF2 gene synthesis | 172 |
| smORF2-146 | GGCCCTGGCGTTCCACTGTACCGGGGCACAAAGTCTGCGTGTCCAATGGGCCTCTCTT | smORF2 gene synthesis | 173 |
| smORF2-147 | TGTGCCCCGGTACAGTGGAAACGCCAGGGCCAAAGGGGAGTGGGTGGGTAGGGGAGT | smORF2 gene synthesis | 174 |
| smORF2-148 | ACCAAAAGTCCCCCTTACCCACCACCCCAGCCCCACTGCCCTCCCCACTCCCCCCCTTT | smORF2 gene synthesis | 175 |
| smORF2-149 | GGGGGTGGGTGGGTAAGGGGGACTTTTGGGTAATTGGTATAGCATTGGAAATGAGCTAAATA | smORF2 gene synthesis | 176 |
| smORF2-150 | GGGTCGACGGATCCTTTATTAGGTATTTAGCTCATTTACATTTCCAATGCTAT | smORF2 gene synthesis | 177 |
| smORF1-1 | GCGAATTCGGCGCCGCCACCATGGCCACCATGGCCAAGGGCCAAGCGCCGCCAACCTGACCAACCGCAA | smORF1 gene synthesis | 178 |
| smORF1-2 | GGTGGGGGTGCTGGGCTCGGGGCTGTGGGCGCTGTGGTCCTGGTTGCGGTTCAGGTTGCG | smORF1 gene synthesis | 179 |
| smORF1-3 | CCGAGCCCAGCACCCCACCAGCCCAGCCCCAGCGCCCAAACCCCAACACCCCGAGAACCTGG | smORF1 gene synthesis | 180 |
| smORF1-4 | TCCTCCACCATCATCATCAGGTAGGCCTTCAGGTCCAGGTTCTCGGGGGGTGTTG | smORF1 gene synthesis | 181 |
| smORF1-5 | CTGATGATGGTGGAGGACATCAAGAAGGACTTCAACAAGAGCCTGAAGGAGATCCAG | smORF1 gene synthesis | 182 |
| smORF1-6 | GCTTCTCCTTCAGCACCTGCAGCTCCTTGGCGGTGTTCTCCTGGATCTCCTTCAGGCTCT | smORF1 gene synthesis | 183 |
| smORF1-7 | GCAGGTGCTGAAGGAGAAGCAGGAGGAGAACACCATCAAGCAGGTGGAGGTGCTGACCGAGAA | smORF1 gene synthesis | 184 |
| smORF1-8 | CTTGTTCATCTCCATCACCTGCTTGTAGGTCTTCCTCCTTCCTGAGGTCTTCGGTCAGCACCTCCAC | smORF1 gene synthesis | 185 |

FIG. 10 (continued)

| | | | |
|---|---|---|---|
| smORF1-9 | AGGTGATGGAGATGAACAAGACCATCCTGGACCTGAAGCG | smORF1 gene synthesis | 186 |
| smORF1-10 | CGGAATTCGTCGACCTCGCGCTTCAGGTCCAGGATGGT | smORF1 gene synthesis | 187 |
| smORF1-11 | GCGAATTCGTCGACACCATCAAGAAGACCCAGAGCGAGGCCACC | smORF1 gene synthesis | 188 |
| smORF1-12 | CGATGGTGCCGCTCTTCTTGCCCAGGGTCTCGATCTCCAGGGTGGCCTCGCTCTGGGTCT | smORF1 gene synthesis | 189 |
| smORF1-13 | CAAGAAGAGCGGCACCATGACCTGAGCATCAGCAACCGCATCCAGGAGGATGGAGGAGCG | smORF1 gene synthesis | 190 |
| smORF1-14 | GGTGCCGATGTTCTCGATGCTGTCCTCGGCGCCGCTGATGCGCTCCATCTCCTGGAT | smORF1 gene synthesis | 191 |
| smORF1-15 | GCATCGAGAACATCGGCACCACCATCAAGGAGAACGGCAAGTGCAAGAAGATCCTGACCC | smORF1 gene synthesis | 192 |
| smORF1-16 | TTGGGGCGGCGGATGGTGTCCTGGATCTCCTGGATGTTCTGGGTCAGGATCTTCTTGCAC | smORF1 gene synthesis | 193 |
| smORF1-17 | GACACCATCCGCCGCCCAACGTGCGCATCATCGGCGTGGACGAGAACGAGGACTTCCAG | smORF1 gene synthesis | 194 |
| smORF1-18 | CCTCGATGATCTTGTTGAAGATGTTGGCGGGCCCTTCAGCTGGAAGTCCTCGTTCTCGT | smORF1 gene synthesis | 195 |
| smORF1-19 | CTTCAACAAGATCATCGAGGAGAACTTCCCCAACCTGAAGAACGAGATGCACATGAACAT | smORF1 gene synthesis | 196 |
| smORF1-20 | GGGTGCCGGTAGGCCTCCTGGATGTTCATGTGCATCTCGTT | smORF1 gene synthesis | 197 |
| smORF1-21 | CCAGGAGGCCTACCGCACCCCAACCGCCTGGACCAGAAG | smORF1 gene synthesis | 198 |
| smORF1-22 | CGGAATTCTCTAGAGCTGTTGCGCTTCTGGTCCAGGCGGTTGG | smORF1 gene synthesis | 199 |
| smORF1-23 | GCGAATTCTCTAGACACATCATCATCCGCACACAGCACAAGCCCTGAACAAGGACCGCATC | smORF1 gene synthesis | 200 |
| smORF1-24 | CCTTGTAGGTCACCTGGCCCTTCTCGCGCACGGCCTTCAGGATGCGGTCCTTGTTCAGGG | smORF1 gene synthesis | 201 |
| smORF1-25 | GGGCCAGGTGACCTACAAGGGCAAGCCCATCCGACTCACCCCGACTTCAGCCCGAGAC | smORF1 gene synthesis | 202 |
| smORF1-26 | GGTCTGGATCACGTCGGTCCAGGACCTGCAGGCCCTTCATGGTCTCGGGGCTGAAGTCGGG | smORF1 gene synthesis | 203 |
| smORF1-27 | GGACCGACGTGATCCAGACCCTGCGGAGCACAAGCTGCAGCCCCGCCTGCTGTACCCCG | smORF1 gene synthesis | 204 |
| smORF1-28 | AACACCTTGGTCTCGCCCTGCGATGATGATGTCAGCTTGGCGGGTACAGCAGGCGGGGC | smORF1 gene synthesis | 205 |
| smORF1-29 | GAGGGCGAGACCAAGGTGTTCCACGACAAGGTTCACCCACTACCTGAGCACCAAC | smORF1 gene synthesis | 206 |
| smORF1-30 | TGTACTGGTTCTTCTCGGTGATGATGCGCTGCAGGGCGCTGGTGCTCAGGTAGTGGG | smORF1 gene synthesis | 207 |
| smORF1-31 | CACCGAGAAGAACCAGTACAAGAACGGCAACACGCCCTGGAGAAGACCCGCCGCTAATC | smORF1 gene synthesis | 208 |
| smORF1-32 | CGGAATTCTTAATTAAGGTTTGTTGAGGGATTAGCGGGGCGGGTCTTCTC | smORF1 gene synthesis | 209 |

FIG. 11

| SEQ ID NO. | SEQUENCE |
|---|---|
| 210 | GCGAATTCGCGGCCGCGTTTAAACTTAATTAAGCCACCATGGGCA |
| 211 | TGTTGCCGGTCTTGCGGTTCTGCTTCTTGCCCATGGTGGCTTAAT |
| 212 | ACCGCAAGACCGGCAACAGCAAGACCCAGAGCGCCAGCCCCCCCC |
| 213 | TGGCGGGGCTGCTGCTGCGCTCCTTGGGGGGGGGGCTGGCGCTCT |
| 214 | GCAGCAGCAGCCCCGCCACCGAGCAGAGCTGGATGGAGAACGACT |
| 215 | GGAAGCCCTCCTCGCGCAGCTCGTCGAAGTCGTTCTCCATCCAGC |
| 216 | TGCGCGAGGAGGGCTTCCGCCGCAGCAACTACAGCGAGCTGCGCG |
| 217 | CCTCCTTGCCCTTGGTCTGGATGTCCTCGCGCAGCTCGCTGTAGT |
| 218 | AGACCAAGGGCAAGGAGGTGGAGAACTTCGAGAAGAACCTGGAGG |
| 219 | CGGTGTTGGTGATGCGGGTGATGCACTCCTCCAGGTTCTTCTCGA |
| 220 | CCCGCATCACCAACACCGAGAAGTGCCTGAAGGAGCTGATGGAGC |
| 221 | CGCGCAGCTCGCGGGCCTTGGTCTTCAGCTCCATCAGCTCCTTCA |
| 222 | AGGCCCGCGAGCTGCGCGAGGAGTGCCGCAGCCTGCGCAGCCGCT |
| 223 | GCGAATTCAATTGGTCGCAGCGGCTGCGCAGGCTGC |
| 224 | GCGAATTCAATTGGAGGAGCGCGTGAGCGCCATGGAGGACGAGAT |
| 225 | AACTTGCCCTCGCGCTTCATCTCGTTCATCTCGTCCTCCATGGCG |
| 226 | GAAGCGCGAGGGCAAGTTCCGCGAGAAGCGCATCAAGCGCAACGA |
| 227 | TAGTCCCAGATCTCCTGCAGGCTCTGCTCGTTGCGCTTGATGCGC |
| 228 | GCAGGAGATCTGGGACTACGTGAAGCGCCCCAACCTGCGCCTGAT |
| 229 | TTCTCCACGTCGCTCTCGGGCACGCCGATCAGGCGCAGGTTGGGG |
| 230 | CGAGAGCGACGTGGAGAACGGCACCAAGCTGGAGAACACCCTGCA |
| 231 | TTGGGGAAGTTCTCCTGGATGATGTCCTGCAGGGTGTTCTCCAGC |
| 232 | CCAGGAGAACTTCCCCAACCTGGCCCGCCAGGCCAACGTGCAGAT |
| 233 | CGCTGGGGGGTGCGCTGGATCTCCTGGATCTGCACGTTGGCCTGG |
| 234 | CCAGCGCACCCCCAGCGCTACAGCAGCCGCCGCGCCACCCCCCG |
| 235 | ACCTTGGTGAAGCGCACGATGATGTGGCGGGGGGTGGCGCGGCGG |
| 236 | CGTGCGCTTCACCAAGGTGGAGATGAAGGAGAAGATGCTGCGCGC |
| 237 | AGGGTCACGCGGCCCTTCTCGCGGGCGGCGCGCAGCATCTTCTCC |
| 238 | GAAGGGCCGCGTGACCCTGAAGGGCAAGCCCATCCGTCTCACCGC |
| 239 | GCGAATTCGGCGGTGAGACGGATGGGC |
| 240 | GCGAATTCGTCTCACCGCCGACCTGAGCGCCGAGACCCTGCAGGC |
| 241 | TTGAAGATGGGGCCCCACTCGCGGCGGGCCTGCAGGGTCTCGGCG |
| 242 | GTGGGGCCCCATCTTCAACATCCTGAAGGAGAAGAACTTCCAGCC |
| 243 | CTCAGCTTGGCGGGGTAGCTGATGCGGGGCTGGAAGTTCTTCTCC |
| 244 | CTACCCCGCCAAGCTGAGCTTCATCAGCGAGGGCGAGATCAAGTA |
| 245 | TCGCGCAGCATCTGCTTGTCGATGAAGTACTTGATCTCGCCCTCG |
| 246 | CAAGCAGATGCTGCGCGACTTCGTGACCACCCGCCCCGCCCTGAA |
| 247 | ATGTTCAGGGCCTCCTTCAGCAGCTCCTTCAGGGCGGGGCGGGTG |
| 248 | GAAGGAGGCCCTGAACATGGAGCGCAACAACCGCTACCAGCCCCT |

FIG. 11 (continued)

| | |
|---|---|
| 249 | GGTCTTTACATCTTGGCGTGGTTCTGCAGGGGCTGGTAGCGGTTG |
| 250 | CGCCAAGATGTAAAGACCATCGAGACTAGGAAGAAACTGCATCAA |
| 251 | ATGGGCGCGCCTGATTTTGCTCATTAGTTGATGCAGTTTCTTCCT |
| 252 | AAAATCAGGCGCGCCCATCATAATGACCGGCAGCAACAGCCACAT |
| 253 | GCGAATTCATGTGGCTGTTGCTGCCGG |
| 254 | GCGAATTCGGCGCGCCCATCATAATGACCGGCAGCAACAGCCACA |
| 255 | CGTTGATGTTCAGGGTCAGGATGGTGATGTGGCTGTTGCTGCCGG |
| 256 | TGACCCTGAACATCAACGGCCTGAACAGCGCCATCAAGCGCCACC |
| 257 | CCTGGCTCTTGATCCAGCTGGCCAGGCGGTGGCGCTTGATGGCGC |
| 258 | GCTGGATCAAGAGCCAGGACCCCAGCGTGTGCTGCATCCAGGAGA |
| 259 | GGTGGGTGTCGCGGCAGGTCAGGTGGGTCTCCTGGATGCAGCACA |
| 260 | CCTGCCGCGACACCCACCGCCTGAAGATCAAGGGCTGGCGCAAGA |
| 261 | TCTTCTGCTTGCCGTTGGCCTGGTAGATCTTGCGCCAGCCCTTGA |
| 262 | CCAACGGCAAGCAGAAGAAGGCCGGCGTGGCCATCCTGGTGAGCG |
| 263 | TCTTGGTGGGCTTGAAGTCGGTCTTGTCGCTCACCAGGATGGCCA |
| 264 | ACTTCAAGCCCACCAAGATCAAGCGCGACAAGGAGGGCCACTACA |
| 265 | CCTGCTGGATGCTGCCCTTCACCATGATGTAGTGGCCCTCCTTGT |
| 266 | AGGGCAGCATCCAGCAGGAGGAGCTGACCATCCTGAACATCTACG |
| 267 | GCGAATTCACCGGTGTTGGGGGCGTAGATGTTCAGGATGG |
| 268 | GCGAATTCACCGGTGCCCCCGCTTCATCAAGCAGGTGCTGAGCG |
| 269 | TGTGGCTGTCCAGGTCGCGCTGCAGGTCGCTCAGCACCTGCTTGA |
| 270 | GCGACCTGGACAGCCACACCCTGATCATGGGCGACTTCAACACCC |
| 271 | GGGTGCTGCGGTCCAGGGTGCTCAGGGGGGTGTTGAAGTCGCCCA |
| 272 | CCCTGGACCGCAGCACCCGCCAGAAGGTGAACAAGGACACCCAGG |
| 273 | CGGCCTGGTGCAGGGCGCTGTTCAGCTCCTGGGTGTCCTTGTTCA |
| 274 | GCGCCCTGCACCAGGCCGACCTGATCGACATCTACCGCACCCTGC |
| 275 | AGAAGGTGTACTCGGTGCTCTTGGGGTGCAGGGTGCGGTAGATGT |
| 276 | GCACCGAGTACACCTTCTTCAGCGCCCCCCACCACACCTACAGCA |
| 277 | CCTTGCTGCCCACGATGTGGTCGATCTTGCTGTAGGTGTGGTGGG |
| 278 | ACATCGTGGGCAGCAAGGCCCTGCTGAGCAAGTGCAAGCGCACCG |
| 279 | GGTCGCTCAGGTAGTTGGTGATGATCTCGGTGCGCTTGCACTTGC |
| 280 | CCAACTACCTGAGCGACCACAGCGCCATCAAGCTGGAGCTGCGCA |
| 281 | TGCTGCGGCTCTGGGTCAGGTTCTTGATGCGCAGCTCCAGCTTGA |
| 282 | TGACCCAGAGCCGCAGCACCACCTGGAAGCTGAACAACCTGCTGC |
| 283 | TCTCGTTGTGCACCCAGTAGTCGTTCAGCAGCAGGTTGTTCAGCT |
| 284 | ACTGGGTGCACAACGAGATGAAGGCCGAGATCAAGATGTTCTTCG |
| 285 | GCGAATTCGAAGAACATCTTGATCT |
| 286 | GCGAATTCTTCGAAACCAACGAGAACAAGGACACCACCTACCAGA |
| 287 | ACACGGCCTTGAAGGCGTCCCACAGGTTCTGGTAGGTGGTGTCCT |
| 288 | ACGCCTTCAAGGCCGTGTGCCGCGGCAAGTTCATCGCCCTGAACG |
| 289 | TGCTGCGCTCCTGCTTGCGCTTGTAGGCGTTCAGGGCGATGAACT |
| 290 | GCAAGCAGGAGCGCAGCAAGATCGACACCCTGACCAGCCAGCTGA |
| 291 | GGGTCTGCTCCTGCTTCTCCAGCTCCTTCAGCTGGCTGGTCAGGG |
| 292 | AGAAGCAGGAGCAGACCCACAGCAAGGCCAGCCGCCGCCAGGAGA |
| 293 | CCTTCAGCTCGGCGCGGATCTTGGTGATCTCCTGGCGGCGGCTGG |

FIG. 11 (continued)

| | |
|---|---|
| 294 | TCCGCGCCGAGCTGAAGGAGATCGAGACCCAGAAGACCCTGCAGA |
| 295 | GCGAATTCGCGACTCGTTGATCTTCTGCAGGGTCTTCTGGG |
| 296 | GCGAATTCTCGCGAAGCTGGTTCTTCGAGCGCATCAACAAGATCG |
| 297 | TCTTGATCAGGCGGGCCAGGGGGCGGTCGATCTTGTTGATGCGCT |
| 298 | TGGCCCGCCTGATCAAGAAGAAGCGCGAGAAGAACCAGATCGACA |
| 299 | TGATGTCGCCCTTGTCGTTCTTGATGGTGTCGATCTGGTTCTTCT |
| 300 | ACGACAAGGGCGACATCACCACCGACCCCACCGAGATCCAGACCA |
| 301 | ACAGGTGCTTGTAGTACTCGCGGATGGTGGTCTGGATCTCGGTGG |
| 302 | AGTACTACAAGCACCTGTACGCCAACAAGCTGGAGAACCTGGAGG |
| 303 | TGTAGGTGTCCAGGAAGGTGTCCATCTCCTCCAGGTTCTCCAGCT |
| 304 | CCTTCCTGGACACCTACACCCTGCCCCGCCTGAACCAGGAGGAGG |
| 305 | CGGTGATGGGCGGTTCAGGCTCTCCACCTCCTCCTGGTTCAGGC |
| 306 | TGAACCGCCCCATCACCGGCAGCGAGATCGTGGCCATCATCAACA |
| 307 | GGCCGGGGCTCTTCTTGGTGGGCAGGCTGTTGATGATGGCCACGA |
| 308 | CCAAGAAGAGCCCCGGCCCCGACGGCTTCACCGCCGAGTTCTACC |
| 309 | AGGGCACCAGCTCCTCCTTGTAGCGCTGGTAGAACTCGGCGGTGA |
| 310 | AGGAGGAGCTGGTGCCCTTCCTGCTGAAGCTGTTCCAGAGCATCG |
| 311 | AGCTGTTGGGCAGGATGCCCTCCTTCTCGATGCTCTGGAACAGCT |
| 312 | GCATCCTGCCCAACAGCTTCTACGAGGCCAGCATCATCCTGATCC |
| 313 | TCTTGGTGGTGTCGCGGCCGGGCTTGGGGATCAGGATGATGCTGG |
| 314 | GCCGCGACACCACCAAGAAGGAGAACTTCCGCCCCATCAGCCTGA |
| 315 | TGTTCAGGATCTTGGCGTCGATGTTCATCAGGCTGATGGGGCGGA |
| 316 | ACGCCAAGATCCTGAACAAGATCCTGGCCAACCGCATCCAGCAGC |
| 317 | GGTCGTGGTGGATCAGCTTCTTGATGTGCTGCTGGATGCGGTTGG |
| 318 | AGCTGATCCACCACGACCAGGTGGGCTTCATCCCCGGGATGCAGG |
| 319 | GCGAATTCCCTGCATCCCGGGGATGA |
| 320 | GCGAATTCCCCGGGATGCAGGGCTGGTTCAACATCCGCAAGAGCA |
| 321 | CGCGGTTGATGTGCTGGATCACGTTGATGCTCTTGCGGATGTTGA |
| 322 | TCCAGCACATCAACCGCGCCAAGGACAAGAACCACATGATCATCA |
| 323 | TGTCGAAGGCCTTCTCGGCGTCGATGCTGATGATCATGTGGTTCT |
| 324 | CCGAGAAGGCCTTCGACAAGATCCAGCAGCCCTTCATGCTGAAGA |
| 325 | TGCCGTCGATGCCCAGCTTGTTCAGGGTCTTCAGCATGAAGGGCT |
| 326 | AGCTGGGCATCGACGGCACCTACTTCAAGATCATCCGCGCCATCT |
| 327 | GGATGATGTTGGCGGTGGGCTTGTCGTAGATGGCGCGGATGATCT |
| 328 | CCACCGCCAACATCATCCTGAACGGCCAGAAGCTGGAGGCCTTCC |
| 329 | CGAATTCACGCGTGCCGGTCTTCAGGGGGAAGGCCTCCAGCTTCT |
| 330 | GCGAATTCACGCGTCAGGGCTGCCCCTGAGCCCCTGCTGTTCA |
| 331 | CGCGGGCCAGCACCTCCAGCACGATGTTGAACAGCAGGGGGCTCA |
| 332 | TGGAGGTGCTGGCCCGCGCCATCGCCAGGAGAAGGAGATCAAGG |
| 333 | TCACCTCCTCCTTGCCCAGCTGGATGCCCTTGATCTCCTTCTCCT |
| 334 | TGGGCAAGGAGGAGGTGAAGCTGAGCCTGTTCGCCGACGACATGA |
| 335 | TCACGATGGGGTTCTCCAGGTACACGATCATGTCGTCGGCGAACA |
| 336 | TGGAGAACCCCATCGTGAGCGCCCAGAACCTGCTGAAGCTGATCA |
| 337 | TGTAGCCGCTCACCTTGCTGAAGTTGCTGATCAGCTTCAGCAGGT |
| 338 | GCAAGGTGAGCGGCTACAAGATCAACGTGCAGAAGAGCCAGGCCT |

FIG. 11 (continued)

| | |
|---|---|
| 339 | CGGTCTGGCGGTTGTTGGTGTACAGGAAGGCCTGGCTCTTCTGCA |
| 340 | CCAACAACCGCCAGACCGAGAGCCAGATCATGGGCGAGCTGCCCT |
| 341 | GCGAATTCGCTAGCGATGGTGAAGGGCAGCTCGCCCATGA |
| 342 | GCGAATTCGCTAGCAAGCGCATCAAGTACCTGGGCATCCAGCTGA |
| 343 | CCTTGAACAGGTCCTTCACGTCGCGGGTCAGCTGGATGCCCAGGT |
| 344 | TGAAGGACCTGTTCAAGGAGAACTACAAGCCCTGCTGAAGGAGA |
| 345 | TCTTCCACTTGTTGGTCTCCTCCTTGATCTCCTTCAGCAGGGGCT |
| 346 | AGACCAACAAGTGGAAGAACATCCCTGCAGCTGGGTGGGCCGCA |
| 347 | GCAGGATGGCCATCTTCACGATGTTGATGCGGCCCACCCAGCTGC |
| 348 | TGAAGATGGCCATCCTGCCCAAGGTGATCTACCGCTTCAACGCCA |
| 349 | AGAAGGTCATGGGCAGCTTGATGGGGATGGCGTTGAAGCGGTAGA |
| 350 | AGCTGCCCATGACCTTCTTCACCGAGCTGGAGAAGACCACCCTGA |
| 351 | GGGCGCGCTTCTGGTTCCAGATGAACTTCAGGGTGGTCTTCTCCA |
| 352 | GGAACCAGAAGCGCGCCCGCATCGCCAAGAGCATCCTGAGCCAGA |
| 353 | GCAGGGTGATGCCGCCGGCCTTGTTCTTCTGGCTCAGGATGCTCT |
| 354 | CCGGCGGCATCACCCTGCCCGACTTCAAGCTGTACTACAAGGCCA |
| 355 | ACCAGTACCAGGCGGTCTTGGTCACGGTGGCCTTGTAGTACAGCT |
| 356 | AGACCGCCTGGTACTGGTACCAGAACCGCGATATCGACCAGTGGA |
| 357 | GCGAATTCCACTGGTCGATATCGCGG |
| 358 | GCGAATTCGATATCGACCAGTGGAACCGCACCGAGCCCAGCGAGA |
| 359 | TCAGGTAGTTGTAGATGTGGGGCATGATCTCGCTGGGCTCGGTGC |
| 360 | ACATCTACAACTACCTGATCTTCGACAAGCCCGAGAAGAACAAGC |
| 361 | TGTTGAACAGGCTGTCCTTGCCCCACTGCTTGTTCTTCTCGGGCT |
| 362 | AGGACAGCCTGTTCAACAAGTGGTGCTGGGAGAACTGGCTGGCCA |
| 363 | AGGGGTCCAGCTTCAGCTTGCGGCAGATGGCCAGCCAGTTCTCCC |
| 364 | AGCTGAAGCTGGACCCCTTCCTGACCCCCTACACCAAGATCAACA |
| 365 | TCACGTTCAGGTCCTTGATCCAGCGGCTGTTGATCTTGGTGTAGG |
| 366 | TCAAGGACCTGAACGTGAAGCCCAAGACCATCAAGACCCTGGAGG |
| 367 | TGTCCTGGATGGTGATGCCCAGGTTCTCCTCCAGGGTCTTGATGG |
| 368 | GCATCACCATCCAGGACATCGGCGTGGGCAAGGACTTCATGAGCA |
| 369 | CCTTGGTGGCCATGGCCTTGGGGGTCTTGCTCATGAAGTCCTTGC |
| 370 | AGGCCATGGCCACCAAGGACAAGATCGACAAGTGGGACCTGATCA |
| 371 | CCTTGGCGGTGCAGAAGCTCTTCAGCTTGATCAGGTCCCACTTGT |
| 372 | GCTTCTGCACCGCCAAGGAGACCACCATCCGCGTGAACCGCCAGC |
| 373 | TGGCGAAGATCTTCTCCCAGGTGGTGGGCTGGCGGTTCACGCGGA |
| 374 | GGGAGAAGATCTTCGCCACCTACAGCAGCGACAAGGGCCTGATCA |
| 375 | TCTGCTTCAGCTCGTTGTAGATGCGGCTGATCAGGCCCTTGTCGC |
| 376 | ACAACGAGCTGAAGCAGATCTACAAGAAGAAGACCAACAACCCCA |
| 377 | GGTTCATGTCCTTGGCCCACTTCTTGATGGGGTTGTTGGTCTTCT |
| 378 | GGGCCAAGGACATGAACCGCCACTTCAGCAAGGAGGACATCTACG |
| 379 | GCGAATTCATATGCTTCTTGGCGGCGTAGATGTCCTCCTTGC |
| 380 | GCGAATTCATATGAAGAAGTGCAGCAGCAGCCTGGCCATCCGCGA |
| 381 | TAGCGCATGGTGGTCTTGATCTGCATCTCGCGGATGGCCAGGCTG |
| 382 | CAAGACCACCATGCGCTACCACCTGACCCCCGTGCGCATGGCCAT |
| 383 | CAGCGGTTGTTGCCGCTCTTCTTGATGATGGCCATGCGCACGGGG |

FIG. 11 (continued)

| | | |
|---|---|---|
| 384 | GAGCGGCAACAACCGCTGCTGGCCGGCTGCGGCCGGAGATCGGCAC | |
| 385 | TTGCAGTCCCACCAGCAGTGCAGCAGGGTGCCGATCTCGCCGCAG | |
| 386 | CTGCTGGTGGGACTGCAAGCTGGTGCAGCCCCTGTGGAAGAGCGT | |
| 387 | AGCTCCAGGTCGCGCAGGAAGGCCACACGCTCTTCCACAGGGGC | |
| 388 | CCTGCGCGACCTGGAGCTGGAGATGCCCAGCAGGGGATGCCCATCCC | |
| 389 | TACTCGTTGGGGTAGATGCCCAGCAGGATGGCGGGGTCGAAG | |
| 390 | CATCTACCCAACGAGTACAAGAGCTGCTGCTACAAGGACACCTG | |
| 391 | AACAGGGGCGATGAACATGCGGGTGCAGGTGTCCTTGTAGCAG | |
| 392 | GTTCATCGCGCCCTGTTCACCATCGCCAAGACCTGAACCAGCC | |
| 393 | ATCCAATCGATCATGGTGGGGCACTTGGGCTGGTTCCAGGTCTTG | |
| 394 | CACCATGATCGATTGGATCAAGAAGATGTGGCACATCTACACCAT | |
| 395 | GCGAATTCATGGTGTAGATGTGCCAC | |
| 396 | GCGCTCGAGATCGATTGGATCAAGAAGATGTGGCACATCTACACC | |
| 397 | GTTCTTTGATGGCGGCGTAGTACTCCATGGTGTAGATGTGCCACAT | |
| 398 | TACGCGCCATCAAGAACGACGAGTTCATCAGCTTCGTGGGCACC | |
| 399 | CAGGATGATGTCTCCAGTTCATCCAGGTGCCCACGAAGCTGAT | |
| 400 | CTGGAGACCATCATCCTGAAGCTGAGCAGGAGCAGGAGAAGACC | |
| 401 | GCCGATCAGGCTGAAGATGCGGGTCAACTGAGTATACGGATCCGAATTC | |
| 402 | ATCTTCAGCTCGAGAATTCGGATCCGTATAC | |
| 403 | AGCGCTCGAGAATTCGGATCCGTATAC | |
| 404 | CCATTTTACATCTTGGCGTGGTTCTGCAGGGGCTGGTAGCGGTTG | |
| 405 | CGCCAAGATGTAAAATGGTTTTATACTCTAATCACTGCTAATTAT | |
| 406 | GAAGGCGCGCCTAGTCAAATAAAAGAAATAATTAGCAGTGATTAG | |
| 407 | TTGACTAGGCGCGCCTTCAATTATGACCGGCAGCAACAGCCACAT | |
| 408 | GCGAATTCGATGTGCTGTTGCTGCCG | |
| 409 | GCGAATTCGGCGCGCCTTCAATTATGACGGCAGCAACAGCCACA | |
| 410 | GTGGCCGGCGGGCGGCCTCGAGCTCGGCGCATATGCTCGAGCGC | sL1 linkersense |
| 411 | GGCGCTCGAGCATATGCGCCGAGCTCGCGCCGCGAGGCCGCCA | sL1linkerantisense |

FIG. 12 (continued)

| | | | | | | | | | | | | | | | | | | | | | | | | | |
|---|---|---|---|---|---|---|---|---|---|---|---|---|---|---|---|---|---|---|---|---|---|---|---|---|---|
L1spa coding | A G G A | A A A A | A A C A | A T A C A A | A C A G G T G A T G G A | A A T G A A C A A A A C |
smL1 coding | A G G A | A G A G | A G A C | C T A C A A G | C A G G T G A T G G A | G A T G A A C A A G A C |

(300, 350)

L1spa coding | C A T A C T | A G A C C T | A A A A A G G A | A G T A G A C A C A A T | A A A G A A A |
smL1 coding | C A T C C T | G G A C C T | G A A A A G G C G | A G G T C G A C A C C | A A G A A G |

```
                   2250
L1spa coding  C T A T T C A A A G A A T T A A C C A A A C G A G G A G T T G G T T C T T T G A
smL1 coding   C C A T C C A A C G G A T C A A C C A G A C C C G G T C T T G G T T C T T C G A L1spa coding  G A A A T C A A C A A G A T A G A T A A A C C C T A G C T A G A C T C A C T
smL1 coding   G A A G A T C A A C A A G A T C G A C A A G C C C T C G C C T G A C C
                                   2300                                   2350

L1spa coding  A G G G C A C A G G G A G A C A T A A A A T C C T A A T T A A C A A G A A
smL1 coding   A G G G C C A C C C G C G A C A T C A C C A C C C T G A T C A A C A C G C A
                                                                          2400

L1spa coding  A T G A A A G G G A G A C A T C C T T C T A C A A A A G G C T A C T C A A C A
smL1 coding   A C G A G A A G G G C C A C A T C C T C G A G G A C T G G A C A A C A L1spa coding  A A A C C A T C C A G A T C C C G C T T C T A C A A G C G C C T G T A C A C C A
smL1 coding   G A A C C A T C C C A G C T T C T A C A A G C G C C T G T A C A G C A C C
                                           2450

L1spa coding  A A A C T G G A A A A C C T G G A C G A A A A T G G A C A A T T T C T G G A C A
smL1 coding   A A G C T G G A G A A C C T G G A C G A G A T G G A C A A G T T C C T G G A C C
                                                   2500

L1spa coding  G A T A C C A G G T A C C A A A A G T T G A A T C A G G A T C A A G T T G A C C T
smL1 coding   G C T A T C A G G T G C C C A G G A C T G A A C C A G G A C C A G G T G A C C T
```

FIG. 12 (continued)

```
L1spa coding  TCT AAACAGT CCCAT ATCCCCT AAA AGAAAT AGAAGCAGT T
smL1 coding   GCT GAACAGC CCCAT CTCCCCC AAG GAAAT CGAGCCGT G L1spa coding  ATT AATAGT CTC CCC AGCCAGA AAA AGCCC AGA CCAGACG
smL1 coding   ATC AACAGC CCT GCC GCCAAGA AAA AGAGC CGG CCCGACG L1spa coding  GGT TAGTGCA GAGTTCTA TGCACAA ACC TTCAA AGAAGATCT
smL1 coding   GCT CAGCGCT GAGTTCTA CGCACAA ACC TTCAA AGGAGACCT L1spa coding  AAC CAGT ATT CTC CCC TAA ACC AAA CTTTT TCA TTTTATGAAGATCGA
smL1 coding   GAC CAGC CCC GTG CCC CAA GCC CAA GCTTTT CCA CTTTATGAAGATCA L1spa coding  GAA GGT ATT ACC TAC CCC AAC CCA AGA AAG ATC AGC CAC TAT TA
smL1 coding   GAG GGC ATC TCG CCC CCG CAG CCC AGG AAG GAC CAC CAC TCG CA L1spa coding  CTC TGA TAC CAG ACC AAT TTC TCT TAT GAA CAT CGA TGC AAA A
smL1 coding   CCC TGA TCC GCC CAG CCC CAT CAG CCT GAA CAT CGA CGC AAG A L1spa coding  GAA CTT CAG CCT CCG CCA TTT CTC TTA TGA ACA TCG ATG CAA AA
smL1 coding   GAA CTT CCC GAG CCC CAT CAG CCT GAA CAT CGA CGC AAG
```

```
L1spa coding  G C A A A C C A G T A G C C A A C A T C A A A G T A A A T G G A G A G A A G C T
smL1 coding   G C A A G C C C G T C G C C A A C A T C A A G G T A A C G G G G A G A A G C T
                                              3100                    3150

L1spa coding  G G A A G C A A T C C C C A C T A A A A T C A G G G A C T A G A C A A G G C T G C
smL1 coding   G G A G C C A T C C C C C T C T G A A G A G C G G C A C G C G T C A G G C T G T
                                                                                    3200

L1spa coding  C C A C T T T C T C C C C T A C C T T T T C A A C A T A G T A C T T G A A G T A T
smL1 coding   C C T C T G T C C C C C T A C C T G T T C A A C A T C G T G C T G G A G G T G C L1spa coding  T A G C C A G C A A T T C G A C A A A A G G A G A T C A A G G G A T
smL1 coding   T G G C C G C T A T C C G G C A G C A G A G A A T C A G G G C A T
                                  3250

L1spa coding  A C A A T T G G A A A A G A G G A A G T C A A A A T A T C A C T T T T T G C A
smL1 coding   C C A G A T C G G C A A G C A G G A G A A G T G A A G A T C A G C C T G T T C G C
                                                    3300

L1spa coding  G A T G A T A G T A T A T A A G A C C C T A A A A G A A T T C C A
smL1 coding   G A C G A C A T C G T A C A G C A G C C C C A A G A A C A G C A L1spa coding  A C A G A A C T C C T G A T A A A A C C T G A T A A A G C T T C G G T G A A G T
smL1 coding   A C G G A G C T C C T G A T C A A C C T G A T C A A C A G C T T C G G C G A G G T
                                                          3350
```

FIG. 12 (continued)

```
                                                                                    3400
L1spa coding: AGCTGG ATA AAA ATT AAC TCA AAC AAG TCA ATG GCC TTT
sml1 coding:  GGCTGG CTA CAA GAT CAA CAG CAA GAG CAT GGC CTT C L1spa coding: CT CTAC ACA AAG AAC ACA GGC TGA GAA AGA AAT TAG GG
sml1 coding:  CT CTAC ACC AAG AAC ACA GGC CGA GAA AGG AGA TCC GCG 3450
L1spa coding: AA CACA CCC TTC TCA ATA GCC ACA AGC CCA AAT CAA GTA
sml1 coding:  AG CACA CCC CTT CAG CAT CGC CAC AAC AAA CAT CAA GTA L1spa coding: TC TCGG CGT GAC TCT ACG AAG GAC AGT GAA GAT CTG TAT
sml1 coding:  CC TTGG CGT GAC CCT GAC CAA GGA AGG TGA AGG ACC TGT AC
                                        3500
L1spa coding: GA TAAA AAA CTT CAA GTC CCT GAA AGA AAT TAA AGA AG
sml1 coding:  GA CAAG AAC TTC AAG CCC TGA AGA AGG ATC AAG GAG G
                                                              3550                  3600
L1spa coding: AT CTCA GAA GAT GGA AGA TCT CCA TGC TTG TCA TGG TGG
sml1 coding:  AC CTGC GCG GCT GAC CGA AGC CTG AGC CTG GAT CGG AGG L1spa coding: CA GGAC CAA CAT TGT AAA ACA TCT TGC CAA AGC A
sml1 coding:  CC GCAA CAC ATC GTG AAG ATG CCC ATC CCC AAG GCT
```

```
L1spa coding  AGGAATGCAAATCAAAACAAACCCTGAGATTCCACCTCA
smL1 coding   CGCAGATGCAGAGATCAAAGACCCCTGCGCTTCCACCTGA
                                        4500              4550

L1spa coding  CACCAGTGAGAATGGCTAAGATCAAAATTCAGGTGACAG
smL1 coding   CCCCGTGCGGATGGCCAAGATCAAGAACAGCGGCGACTC
                                                              4600

L1spa coding  CAGATGCTGGCGAGGATGTGGAGAAAGAGGAACACCCTC
smL1 coding   CGGATGCTGGCTGGGGATGTGGGGCGCGGCCACCCTGCTG L1spa coding  CATTGTTGGTGGGATTGCAGGCTTGTACAACCACTCTGGA
smL1 coding   CACTGTTGGTGGGACTGCAGGCTCGTCCAGCCCAGCTGGA
                                 4650

L1spa coding  AATCAGTCTGGCGGGTTCCTCAGAAAATGGACATAGTACT
smL1 coding   AGAGCGTGTGGGGTTCCTGCGGAAGCATCGTACT
                                            4700

L1spa coding  ACCGGAGGATCCCAGCCCCAATGGTACCTCCTGGGCATATCCA
smL1 coding   GCCGAGGACGCCCCGGGCCACCCTGGCTGGGCATCTACCCT L1spa coding  GAAGAAGGGTAAGAAGGACACATGCTCCACTACA
smL1 coding   GAGGAGGAGGCAAGAAGGACACCTGCAGTACCA
                                        4750
```

FIG. 12 (continued)

SEQUENCE LISTING

```
<160> NUMBER OF SEQ ID NOS: 433

<210> SEQ ID NO 1
<211> LENGTH: 3846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgccccccc tgaccaccaa gatcaccggc agcaacaact acttcagcct gatcagcctg      60
aacatcaacg gcctgaacag ccccatcaag cggcaccgcc tgaccaactg gctgcacaag     120
caggacccca ccttctgttg cctccaggag acccacctgc gcgagaagga ccggcactac     180
ctgcggatga agggctggaa gaccatcttt caggccaacg gcatgaagaa gcaggctggc     240
gtggccatcc tgatcagcga caagatcgac ttccagccca aggtgatcaa gaaggacaag     300
gagggccact tcatcctgat caagggcaag atcctgcagg aggagctgag cattctgaac     360
atctacgccc ccaacacccg cgccgccacc ttcaccaagg agaccctcgt gaagctgaag     420
gcccacatcg ctccccacac catcatcgtc ggcgacttca acaccccct  gagcccatg     480 gacagatctt ggaagcagaa gctgaaccgc gacaccctga agctgaccga ggtgatgaag     540
cagatggacc tgaccgacat ctaccgcacc ttctacccca agaccaaggg ctacaccttc     600
ttcagcgctc cccacggcac cttcagcaag atcgaccaca tcatcggcca cagagcggg     660 ctgaaccggc tgaagaacat cgagatcgtg ccctgcatcc tgagcgacca ccatgccctg     720
cgcctgatct tcaacaacaa gattaacaac cgcaagccca ccttcacctg gaagctgaac     780
aacaccctgc tgaacgacac cctggtgaag gaaggcatca agaaggagat caaggacttc     840
ctggagttca cgagaacga ggccaccacc taccctaacc tgtgggacac catgaaggcc     900
ttcctgcggg gcaagctgat cgccatgagc gccttcaaga agaagcggga gcgcgcccac     960
actagtagcc tgaccaccca cctgaaggcc ctggagaaga aggaggctaa ctcccccaag    1020
cgctcccggc ggcaggagat catcaagctg cgcggcgaga tcaaccaggt ggagacccgg    1080
cgcaccatcc aacggatcaa ccagacccgg tcttggttct tcgagaagat caacaagatc    1140
gacaagcccc tggctcgcct gaccaaggac caccgcgaca agatcctgat caacaagatc    1200
cgcaacgaga agggcgacat caccaccgac cccgaggaga tccagaacac catccgcagc    1260
```

```
ttctacaagc gcctgtacag caccaagctg gagaacctgg acgagatgga caagttcctg    1320
gaccgctatc aggtgcccaa gctgaaccag gaccaggtgg acctgctgaa cagccccatc    1380
tcccccaagg aaatcgaggc cgtgatcaac agcctgcccg ccaagaagag ccccggcccc    1440
gacggcttca gcgctgagtt ctaccagacc ttcaaggagg acctgacccc cgtgctgcac    1500
aagcttttcc acaagatcga ggtcgagggc atcctcccca acagcttcta cgaggccacc    1560
atcaccctga tccccaagcc ccagaaggac cccaccaaga tcgagaactt ccgccccatc    1620
agcctgatga acatcgacgc caagatcctg aacaagatcc tcgccaaccg catccaggag    1680
cacatcaagg ccatcatcca ccctgaccag gtcggcttca tccccggcat gcagggctgg    1740
ttcaacatcc gcaagagcat caacgtgatc cactacatca acaagctgaa ggacaagaac    1800
cacatgatca tcagcctgga cgccgagaag gccttcgaca agatccagca ccccttcatg    1860
atcaaggtcc tggagcgcag cggcattcag ggccagtacc tcaacatgat caaggccatc    1920
tacagcaagc ccgtcgccaa catcaaggtg aacggggaga gctggaggc catccctctg    1980 aagagcggca cgcgtcaggg ctgtcctctg tcccctacc tgttcaacat cgtgctggag    2040
gtgctggccc cgctatccg gcagcagaag gagatcaagg catccagat cggcaaggag    2100 gaagtgaaga tcagcctgtt cgccgacgac atgatcgtgt acatcagcga ccccaagaac    2160
agcaaccgcg agctcctgaa cctgatcaac agcttcggcg aggtggctgg ctacaagatc    2220
aacagcaaca agagcatggc cttcctgtac accaagaaca gcaggccga aaggagatc    2280 cgcgagacca ccccttcag catcgccacc aacaacatca agtacctggg cgtgaccctg    2340
accaaggagg tgaaggacct gtacgacaag aacttcaaga gcctgaagaa ggagatcaag    2400
gaggacctgc gccgctggaa ggacctgccc tgcagctgga tcggccgcac caacatcgtg    2460
aagatggcca tcctgcccaa ggctatctac cgcttcaacg ccatccccat caagatcccc    2520
acccagttct tcaacgagct cgagggcgcc atctgcaagt tcatctggaa caacaagaag    2580
ccccgcatcg ccaagaccct gctgaaggac aagcgcacca gtgggggat caccatgccc    2640 gacctgaagc tgtactaccg cgccatcgtg atcaagaccg cctggtactg gtaccgcgac    2700
cgccaggtgg accagtggaa ccgcatcgag accccgaga tgaaccccca cacctacggc    2760
cacctgatct tcgacaaggg cgccaagacc atccagtgga gaaggacag catcttcaac    2820 aactggtgct ggcacaactg gctgctgagc tgccgccga tgcgcatcga cccctaccta    2880
agcccctgca ccaaggtgaa gagcaagtgg atcaaggagc tgcacatcaa gcccgagact    2940
ctgaagctga tcgaggagaa ggtgggcaag agcctggagg acatgggcac cggcgaaaag    3000
ttcctgaacc gcaccgccat ggcctgtgcc gtgcgcagcc ggatcgataa gtgggacctg    3060
atgaagctgc agtccttctg taaggccaag gataccgtgt acaagaccaa cgcccccg    3120 accgactggg agcgcatctt cacctacccc aagagcgacc gcggcctgat cagcaacatc    3180
tacaaggagc tgaagaaggt ggacctgcgc aagagcaaca cccgctgaa gaagtggggc    3240 tccgagctga caaggagtt ctcccccgag gagtaccgca tggccgagaa gcacctgaag    3300
aagtgcagca ccagcctgat catccgcgag atgcagatca gaccaccct gcgcttccac    3360 ctgacccccg tgcggatggc caagatcaag aacagcggcg actcgcgatg ctggcggggc    3420
tgcggcgagc gcggcaccct gctgcactgc tggtgggact gtcgcctggt ccagcccctg    3480
tggaagagcg tgtggcggtt cctgcggaag ctggacatcg tgctgcccga ggaccccgct    3540
atccccctgc tgggcatcta ccctgaggag gcccccaccg gcaagaagga cacctgcagt    3600
```

-continued

| | |
|---|---|
| accatgttca tcgccgctct gttcatcatc gcccgcaact ggaaggagcc ccgctgcccc | 3660 |
| agcaccgagg agtggattca gaagatgtgg tacatctaca ccatggagta ctacagcgcc | 3720 |
| atcaagaaga acgagttcat gaagttcctg gccaagtgga tggacctgga gagcatcatc | 3780 |
| ctgagcgagg tgacccagag ccagcgcaac agccacaaca tgtacagcct gatcagcggc | 3840 |
| tactag | 3846 |

<210> SEQ ID NO 2
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynulceotide

<400> SEQUENCE: 2

| | |
|---|---|
| atggccaagg gcaagcgccg caacctgacc aaccgcaacc aggaccacag ccccagcccc | 60 |
| gagcccagca cccccaccag ccccagcccc ggcaaccccca acaccccga gaacctggac | 120 |
| ctggacctga aggcctacct gatgatgatg gtggaggaca tcaagaagga cttcaacaag | 180 |
| agcctgaagg agatccagga gaacaccgcc aaggagctgc aggtgctgaa ggagaagcag | 240 |
| gagaacacca tcaagcaggt ggaggtgctg accgagaagg aggagaagac ctacaagcag | 300 |
| gtgatggaga tgaacaagac catcctggac ctgaagcgcg aggtcgacac catcaagaag | 360 |
| acccagagcg aggccaccct ggagatcgag accctgggca gaagagcgg caccatcgac | 420 |
| ctgagcatca gcaaccgcat ccaggagatg gaggagcgca tcagcggcgc cgaggacagc | 480 |
| atcgagaaca tcggcaccac catcaaggag aacggcaagt gcaagaagat cctgacccag | 540 |
| aacatccagg agatccagga caccatccgc cgccccaacg tgcgcatcat cggcgtggac | 600 |
| gagaacgagg acttccagct gaagggcccc gccaacatct tcaacaagat catcgaggag | 660 |
| aacttcccca acctgaagaa cgagatgcac atgaacatcc aggaggccta ccgcacccc | 720 |
| aaccgcctgg accagaagcg caacagctct agacacatca tcatccgcac cagcaacgcc | 780 |
| ctgaacaagg accgcatcct gaaggccgtg cgcgagaagg ccaggtgac ctacaagggc | 840 |
| aagcccatcc gcatcacccc cgacttcagc cccgagacca tgaaggcccg ccgcgcctgg | 900 |
| accgacgtga tccagaccct cgcgcgagcac aagctgcagc cccgcctgct gtaccccgcc | 960 |
| aagctgagca tcatcatcga gggcgagacc aaggtgttcc acgacaagac caagttcacc | 1020 |
| cactacctga gcaccaaccc cgccctgcag cgcatcatca ccgagaagaa ccagtacaag | 1080 |
| aacggcaaca acgccctgga gaagacccgc cgctaa | 1116 |

<210> SEQ ID NO 3
<211> LENGTH: 3828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| atgaccggca gcaacagcca catcaccatc ctgaccctga acatcaacgg cctgaacagc | 60 |
| gccatcaagc gccaccgcct ggccagctgg atcaagagcc aggaccccag cgtgtgctgc | 120 |
| atccaggaga cccacctgac ctgccgcgac acccaccgcc tgaagatcaa gggctggcgc | 180 |
| aagatctacc aggccaacgg caagcagaag aaggccggcg tggccatcct ggtgagcgac | 240 |
| aagaccgact tcaagcccac caagatcaag cgcgacaagg agggccacta catcatggtg | 300 |

```
aagggcagca tccagcagga ggagctgacc atcctgaaca tctacgcccc caacaccggt    360
gccccccgct tcatcaagca ggtgctgagc gacctgcagc gcgacctgga cagccacacc    420
ctgatcatgg gcgacttcaa caccccctg agcaccctgg accgcagcac ccgccagaag     480
gtgaacaagg acacccagga gctgaacagc gccctgcacc aggccgacct gatcgacatc    540
taccgcaccc tgcaccccaa gagcaccgag tacaccttct tcagcgcccc ccaccacacc    600
tacagcaaga tcgaccacat cgtgggcagc aaggccctgc tgagcaagtg caagcgcacc    660
gagatcatca ccaactacct gagcgaccac agcgccatca agctggagct gcgcatcaag    720
aacctgaccc agagccgcag caccacctgg aagctgaaca acctgctgct gaacgactac    780
tgggtgcaca acgagatgaa ggccgagatc aagatgttct tcgaaaccaa cgagaacaag    840
gacaccacct accagaacct gtgggacgcc ttcaaggccg tgtgccgcgg caagttcatc    900
gccctgaacg cctacaagcg caagcaggag cgcagcaaga tcgacaccct gaccagccag    960
ctgaaggagc tggagaagca ggagcagacc cacagcaagg ccagccgccg ccaggagatc   1020
accaagatcc gcgccgagct gaaggagatc gagacccaga gaccctgca gaagatcaac    1080 gagtcgcgaa gctggttctt cgagcgcatc aacaagatcg accgcccct ggcccgcctg     1140 atcaagaaga agcgcgagaa gaaccagatc gacaccatca gaacgacaa gggcgacatc     1200 accaccgacc ccaccgagat ccagaccacc atccgcgagt actacaagca cctgtacgcc   1260
aacaagctgg agaacctgga ggagatggac accttcctgg acacctacac cctgccccgc   1320
ctgaaccagg aggaggtgga gagcctgaac cgcccatca ccggcagcga gatcgtggcc     1380
atcatcaaca gcctgcccac caagaagagc cccggccccg acggcttcac cgccgagttc   1440
taccagcgct acaaggagga gctggtgccc ttcctgctga gctgttcca gagcatcgag     1500 aaggagggca tcctgcccaa cagcttctac gaggccagca tcatcctgat ccccaagccc    1560
ggccgcgaca ccaccaagaa ggagaacttc cgccccatca gcctgatgaa catcgacgcc   1620
aagatcctga caagatcct ggccaaccgc atccagcagc acatcaagaa gctgatccac    1680
cacgaccagg tgggcttcat ccccgggatg cagggctggt tcaacatccg caagagcatc   1740
aacgtgatcc agcacatcaa ccgcgccaag gacaagaacc acatgatcat cagcatcgac   1800
gccgagaagg ccttcgacaa gatccagcag cccttcatgc tgaagaccct gaacaagctg    1860
ggcatcgacg gcacctactt caagatcatc cgcgccatct acgacaagcc caccgccaac    1920
atcatcctga cggccagaa gctggaggcc ttccccctga gaccggcac gcgtcagggc      1980 tgccccctga gccccctgct gttcaacatc gtgctggagg tgctggcccg cgccatccgc    2040
caggagaagg agatcaaggg catccagctg gcaaggagg aggtgaagct gagcctgttc     2100
gccgacgaca tgatcgtgta cctggagaac cccatcgtga gcgcccagaa cctgctgaag    2160
ctgatcagca cttcagcaa ggtgagcggc tacaagatca cgtgcagaa gagccaggcc      2220 ttcctgtaca ccaacaaccg ccagaccgag agccagatca tgggcgagct gcccttcacc    2280
atcgctagca agcgcatcaa gtacctgggc atccagctga cccgcgacgt gaaggacctg    2340
ttcaaggaga actacaagcc cctgctgaag gagatcaagg aggagaccaa caagtggaag    2400
aacatcccct gcagctgggt gggccgcatc aacatcgtga agatggccat cctgcccaag    2460
gtgatctacc gcttcaacgc catccccatc aagctgccca tgaccttctt caccgagctg    2520
gagaagacca ccctgaagtt catctggaac cagaagcgcg cccgcatcgc caagagcatc    2580
ctgagccaga agaacaaggc cggcggcatc accctgcccg acttcaagct gtactacaag    2640
```

| | |
|---|---:|
| gccaccgtga ccaagaccgc ctggtactgg taccagaacc gcgatatcga ccagtggaac | 2700 |
| cgcaccgagc ccagcgagat catgccccac atctacaact acctgatctt cgacaagccc | 2760 |
| gagaagaaca agcagtgggg caaggacagc ctgttcaaca agtggtgctg ggagaactgg | 2820 |
| ctggccatct gccgcaagct gaagctggac cccttcctga cccctacac caagatcaac | 2880 |
| agccgctgga tcaaggacct gaacgtgaag cccaagacca tcaagaccct ggaggagaac | 2940 |
| ctgggcatca ccatccagga catcggcgtg gcaaggact tcatgagcaa gacccccaag | 3000 |
| gccatggcca ccaaggacaa gatcgacaag tgggacctga tcaagctgaa gagcttctgc | 3060 |
| accgccaagg agaccaccat ccgcgtgaac cgccagccca ccacctggga gaagatcttc | 3120 |
| gccacctaca gcagcgacaa gggcctgatc agccgcatct acaacgagct gaagcagatc | 3180 |
| tacaagaaga gaccaacaa ccccatcaag aagtgggcca aggacatgaa ccgccacttc | 3240 |
| agcaaggagg acatctacgc cgccaagaag catatgaaga agtgcagcag cagcctggcc | 3300 |
| atccgcgaga tgcagatcaa gaccaccatg cgctaccacc tgaccccgt gcgcatggcc | 3360 |
| atcatcaaga gagcggcaa caaccgctgc tggcgcggct gcggcgagat cggcaccctg | 3420 |
| ctgcactgct ggtgggactg caagctggtg cagcccctgt ggaagagcgt gtggcgcttc | 3480 |
| ctgcgcgacc tggagctgga gatccccttc gaccccgcca tccccctgct gggcatctac | 3540 |
| cccaacgagt acaagagctg ctgctacaag gacacctgca cccgcatgtt catcgccgcc | 3600 |
| ctgttcacca tcgccaagac ctggaaccag cccaagtgcc ccaccatgat cgattggatc | 3660 |
| aagaagatgt ggcacatcta ccatggag tactacgccg ccatcaagaa cgacgagttc | 3720 |
| atcagcttcg tgggcacctg gatgaagctg gagaccatca tcctgagcaa gctgagccag | 3780 |
| gagcagaaga ccaagcaccg catcttcagc ctgatcggcg gcaactga | 3828 |

<210> SEQ ID NO 4
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---:|
| atgggcaaga agcagaaccg caagaccggc aacagcaaga cccagagcgc cagccccccc | 60 |
| cccaaggagc gcagcagcag ccccgccacc gagcagagct ggatggagaa cgacttcgac | 120 |
| gagctgcgcg aggagggctt ccgccgcagc aactacagcg agctgcgcga ggacatccag | 180 |
| accaagggca aggaggtgga gaacttcgag aagaacctgg aggagtgcat cacccgcatc | 240 |
| accaacaccg agaagtgcct gaaggagctg atggagctga gaccaaggc ccgcgagctg | 300 |
| cgcgaggagt gccgcagcct cgcagccgc tgcgaccaat ggaggagcg cgtgagcgcc | 360 |
| atggaggacg agatgaacga gatgaagcgc gagggcaagt ccgcgagaa gcgcatcaag | 420 |
| cgcaacgagc agagcctgca ggagatctgg gactacgtga agcgcccaa cctgcgcctg | 480 |
| atcggcgtgc ccgagagcga cgtggagaac ggcaccaagc tggagaacac cctgcaggac | 540 |
| atcatccagg agaacttccc caacctggcc cgccaggcca cgtgcagat ccaggagatc | 600 |
| cagcgcaccc ccagcgcta cagcagccgc cgcgccaccc ccgccacat catcgtgcgc | 660 |
| ttcaccaagg tggagatgaa ggagaagatg ctgcgcgccg cccgcgagaa gggccgcgtg | 720 |
| accctgaagg gcaagcccat ccgtctcacc gccgacctga gcgccgagac cctgcaggcc | 780 |
| cgccgcgagt ggggcccat cttcaacatc ctgaaggaga agaacttcca gccccgcatc | 840 |

```
agctaccccg ccaagctgag cttcatcagc gagggcgaga tcaagtactt catcgacaag    900
cagatgctgc gcgacttcgt gaccacccgc cccgccctga aggagctgct gaaggaggcc    960
ctgaacatgg agcgcaacaa ccgctaccag cccctgcaga accacgccaa gatgtaa      1017
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gccggtggtg cagatgaact tcagggtcag cttgccgtag gtgg                      44
```

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
caagcggccg gagaacctgc gtgcaatcca tcttgttcaa tcat                      44
```

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ccgcttgggt ggagaggcta ttcggctatg actgggcaca acagacaatc ggctgctctg    60
```

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
cgcagctatt tacccgcagg acatatccac gccctcctac atcgaagctg aaagcacgag    60
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ggagttaggg gcgggactat ggttgct                                         27
```

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 10
atcaggacat agcgttggct acccgtga                                          28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcctggggac tttccacacc ctaactga                                          28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgagttcttc tgaggggatc ggcaataa                                          28

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaaaaaaa aaaaaaaaaa aaaat                                             25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaaaaaaaa aaaaaaaaaa aaaac                                             25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaaaaaaaa aaaaaaaaaa aaaag                                             25

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 16
gcgaattctt ctactagtta caacttgttt tcagtcaatg a                41

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgaattcat ggagaatcca ggacaggcca taataccc                   38

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccgctcgagt ggcagagagt taaagtcctg taatggttg                  39

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgctcgagg cgtgtttccc agggtaatca gtcatcttg                  39

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcgaattctt tagatttatg gaaaatcagg ctgcttac                   38

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcgaattctg ggcccccaaa ataaagtccc tttt                       34

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcgaattcag caaaactcca tctcaaaaac aaaca                       35

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgaattcaa atggacagct ttcctgtctc tggctctc                    38

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgaattctg gaatttaaac cttcaaagaa ttactcccac t                41

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgaattcga cggaagggta tgccttttcc ttcatcac                    38

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcgaattcta caggtgtgag ccacagtgcc tgttttct                    38

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgaattccc taagttcatt ctggaatggc tgaaac                      36

<210> SEQ ID NO 28
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agaatgcccc ccctgaccac caagatcacc ggcagcaaca actacttcag cctgatcagc    60
ctg                                                                 63

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cttgatgggg ctgttcaggc cgttgatgtt caggctgatc aggctgaagt agttgttgct    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aacatcaacg gcctgaacag ccccatcaag cggcaccgcc tgaccaactg gctgcacaag    60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctcctggagg caacagaagg tggggtcctg cttgtgcagc cagttggtca ggcggtgccg    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caggacccca ccttctgttg cctccaggag acccacctgc gcgagaagga ccggcactac    60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaagatggtc ttccagccct tcatccgcag gtagtgccgg tccttctcgc gcaggtgggt    60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctgcggatga agggctggaa gaccatcttt caggccaacg gcatgaagaa gcaggctggc    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtcgatcttg tcgctgatca ggatggccac gccagcctgc ttcttcatgc cgttggcctg    60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtggccatcc tgatcagcga caagatcgac ttccagccca aggtgatcaa gaaggacaag    60

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cttgcccttg atcaggatga agtggccctc cttgtccttc ttgatcacct tgggctggaa    60

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gagggccact tcatcctgat caagggcaag atcctgcagg aggagctgag cattctgaac    60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggtggcggcg cgggtgttgg gggcgtagat gttcagaatg ctcagctcct cctgcaggat    60

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atctacgccc caacacccg cgccgccacc ttcaccaagg agaccctcgt gaagctgaag      60

```
<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```
gacgatgatg gtgtggggag cgatgtgggc cttcagcttc acgagggtct ccttggtgaa      60

```
<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
```
gcccacatcg ctccccacac catcatcgtc ggcgacttca acaccccct gagc      54

```
<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
```
aagatctgtc catggggctc aggggggtgt tgaagtcgcc      40

```
<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
```
cagatcttgg aagcagaagc tgaaccgcga caccctgaag ctgaccgagg tgatgaag      58

```
<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```
ggtgcggtag atgtcggtca ggtccatctg cttcatcacc tcggtcagct tcagggtgtc      60

```
<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
```
cagatggacc tgaccgacat ctaccgcacc ttctacccca agaccaaggg ctacaccttc      60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cttgctgaag gtgccgtggg gagcgctgaa gaaggtgtag cccttggtct tggggtagaa    60

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttcagcgctc cccacggcac cttcagcaag atcgaccaca tcatcggcca caagagcggg    60

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cacgatctcg atgttcttca gccggttcag cccgctcttg tggccgatga tgtggtcgat    60

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctgaaccggc tgaagaacat cgagatcgtg ccctgcatcc tgagcgacca ccatgccctg    60

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gttgttaatc ttgttgttga agatcaggcg cagggcatgg tggtcgctca ggatgcaggg    60

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgcctgatct tcaacaacaa gattaacaac cgcaagccca ccttcacctg gaagctgaac    60

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cttcaccagg gtgtcgttca gcagggtgtt gttcagcttc caggtgaagg tgggcttgcg    60

<210> SEQ ID NO 54
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aacaccctgc tgaacgacac cctggtgaag gaaggcatca agaaggagat caaggacttc    60

<210> SEQ ID NO 55
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtggtggcc tcgttctcgt tgaactccag gaagtccttg atctccttct tgatgccttc    60

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctggagttca acgagaacga ggccaccacc taccctaacc tgtgggacac catgaaggcc    60

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gctcatggcg atcagcttgc cccgcaggaa ggccttcatg gtgtcccaca ggttagggta    60

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttcctgcggg gcaagctgat cgccatgagc gccttcaaga agaagcggga gcgcgcccac    60

```
<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctactagtgt gggcgcgctc ccgcttcttc ttgaaggc                            38

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cactagtagc ctgaccaccc acctgaaggc cctggagaag aaggaggcta actcccccaa   60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cagcttgatg atctcctgcc gccgggagcg cttgggggag ttagcctcct tcttctccag   60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cgctcccggc ggcaggagat catcaagctg cgcggcgaga tcaaccaggt ggagacccgg   60

<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccgggtctgg ttgatccgtt ggatggtgcg ccgggtctcc acctggttga tctcgccgcg   60

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cgcaccatcc aacggatcaa ccagacccgg tcttggttct tcgagaagat caacaagatc   60

<210> SEQ ID NO 65
```

<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
gcccttggtc aggcgagcca ggggcttgtc gatcttgttg atcttctcga agaaccaaga    60

<210> SEQ ID NO 66
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
gacaagcccc tggctcgcct gaccaagggc caccgcgaca agatcctgat caacaagatc    60

<210> SEQ ID NO 67
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
gtcggtggtg atgtcgccct tctcgttgcg gatcttgttg atcaggatct tgtcgcggtg    60

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
cgcaacgaga agggcgacat caccaccgac cccgaggaga tccagaacac catccgcagc    60

<210> SEQ ID NO 69
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
cagcttggtg ctgtacaggc gcttgtagaa gctgcggatg gtgttctgga tctcctcggg    60

<210> SEQ ID NO 70
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
ttctacaagc gcctgtacag caccaagctg gagaacctgg acgagatgga caagttcctg    60

<210> SEQ ID NO 71
<211> LENGTH: 60

<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 71
ctggttcagc ttgggcacct gatagcggtc caggaacttg tccatctcgt ccaggttctc    60

<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 72
gaccgctatc aggtgcccaa gctgaaccag gaccaggtgg acctgctgaa cagccccatc    60

<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 73
gttgatcacg gcctcgattt ccttggggga gatgggctg ttcagcaggt ccacctggtc     60

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 74
tcccccaagg aaatcgaggc cgtgatcaac agcctgcccg ccaagaagag ccccggcccc    60

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 75
ggtctggtag aactcagcgc tgaagccgtc ggggccgggg ctcttcttgg cgggcaggct    60

<210> SEQ ID NO 76
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 76
gacggcttca gcgctgagtt ctaccagacc ttcaaggagg acctgacccc cgtgctgcac    60

<210> SEQ ID NO 77
<211> LENGTH: 38
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 77
aaaagcttgt gcagcacggg ggtcaggtcc tccttgaa                    38

<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caagcttttc cacaagatcg aggtcgaggg catcctcccc aacagcttct acgaggccac    60

<210> SEQ ID NO 79
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gtccttctgg ggcttgggga tcagggtgat ggtggcctcg tagaagctgt tggggaggat    60

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
atcaccctga tccccaagcc ccagaaggac cccaccaaga tcgagaactt ccgccccatc    60

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caggatcttg gcgtcgatgt tcatcaggct gatgggcgg aagttctcga tcttggtggg    60

<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agcctgatga acatcgacgc caagatcctg aacaagatcc tcgccaaccg catccaggag    60

<210> SEQ ID NO 83
<211> LENGTH: 60
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 83
ctggtcaggg tggatgatgg ccttgatgtg ctcctggatg cggttggcga ggatcttgtt     60

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cacatcaagg ccatcatcca ccctgaccag gtcggcttca tccccggcat gcagggctgg     60

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gatcacgttg atgctcttgc ggatgttgaa ccagccctgc atgccgggga tgaagccgac     60

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ttcaacatcc gcaagagcat caacgtgatc cactacatca acaagctgaa ggacaagaac     60

<210> SEQ ID NO 87
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cttctcggcg tccaggctga tgatcatgtg gttcttgtcc ttcagcttgt tgatgtagtg     60

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cacatgatca tcagcctgga cgccgagaag gccttcgaca agatccagca cccttcatg     60

<210> SEQ ID NO 89
<211> LENGTH: 60
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 89
ctgaatgccg ctgcgctcca ggaccttgat catgaagggg tgctggatct tgtcgaaggc    60

<210> SEQ ID NO 90
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atcaaggtcc tggagcgcag cggcattcag ggccagtacc tcaacatgat caaggccatc    60

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caccttgatg ttggcgacgg gcttgctgta gatggccttg atcatgttga ggtactggcc    60

<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tacagcaagc ccgtcgccaa catcaaggtg aacggggaga agctggaggc catccctctg    60

<210> SEQ ID NO 93
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgacgcgtgc cgctcttcag agggatggcc tccagcttct ccccgtt                  47

<210> SEQ ID NO 94
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gcacgcgtca gggctgtcct ctgtccccct acctgttcaa catcgtgctg gag           53

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 95
cttctgctgc cggatagcgc gggccagcac ctccagcacg atgttgaaca ggtaggggga        60

<210> SEQ ID NO 96
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gtgctggccc gcgctatccg gcagcagaag gagatcaagg gcatccagat cggcaaggag        60

<210> SEQ ID NO 97
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtcgtcggcg aacaggctga tcttcacctc ctccttgccg atctggatgc ccttgatctc        60

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gaggtgaaga tcagcctgtt cgccgacgac atgatcgtgt acatcagcga ccccaagaac        60

<210> SEQ ID NO 99
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gttgatcagg ttcaggagct cgcggttgct gttcttgggg tcgctgatgt acacgatcat        60

<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agcaaccgcg agctcctgaa cctgatcaac agcttcggcg aggtggctgg ctacaagatc        60

<210> SEQ ID NO 101
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gtacaggaag gccatgctct tgttgctgtt gatcttgtag ccagccacct cgccgaagct    60

<210> SEQ ID NO 102
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aacagcaaca agagcatggc cttcctgtac accaagaaca agcaggccga gaaggagatc    60

<210> SEQ ID NO 103
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggtggcgatg ctgaaggggg tggtctcgcg gatctccttc tcggcctgct tgttcttggt    60

<210> SEQ ID NO 104
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cgcgagacca cccccttcag catcgccacc aacaacatca agtacctggg cgtgaccctg    60

<210> SEQ ID NO 105
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cttgtcgtac aggtccttca cctccttggt cagggtcacg cccaggtact tgatgttgtt    60

<210> SEQ ID NO 106
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
accaaggagg tgaaggacct gtacgacaag aacttcaaga gcctgaagaa ggagatcaag    60

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gggcaggtcc ttccagcggc gcaggtcctc cttgatctcc ttcttcaggc tcttgaagtt    60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gaggacctgc gccgctggaa ggacctgccc tgcagctgga tcggccgcac caacatcgtg    60

<210> SEQ ID NO 109
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtagatagcc ttgggcagga tggccatctt cacgatgttg gtgcggccga tccagctgca    60

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aagatggcca tcctgcccaa ggctatctac cgcttcaacg ccatccccat caagatcccc    60

<210> SEQ ID NO 111
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccctcgagct cgttgaagaa ctgggtgggg atcttgatgg ggatggcgtt gaagcg    56

<210> SEQ ID NO 112
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
agctcgaggg cgccatctgc aagttcatct ggaacaacaa gaag    44

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
gtccttcagc agggtcttgg cgatgcgggg cttcttgttg ttccagatga acttgcagat    60
```

<210> SEQ ID NO 114
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114

```
ccccgcatcg ccaagaccct gctgaaggac aagcgcacca gtgggggat caccatgccc    60
```

<210> SEQ ID NO 115
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

```
cacgatggcg cggtagtaca gcttcaggtc gggcatggtg atccccccac tggtgcgctt    60
```

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
gacctgaagc tgtactaccg cgccatcgtg atcaagaccg cctggtactg gtaccgcgac    60
```

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
ctcgatgcgg ttccactggt ccacctggcg gtcgcggtac cagtaccagg cggtcttgat    60
```

<210> SEQ ID NO 118
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
cgccaggtgg accagtggaa ccgcatcgag gaccccgaga tgaaccccca cacctacggc    60
```

<210> SEQ ID NO 119
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggtcttggcg cccttgtcga agatcaggtg gccgtaggtg tgggggttca tctcggggtc    60

<210> SEQ ID NO 120
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cacctgatct tcgacaaggg cgccaagacc atccagtgga agaaggacag catcttcaac    60

<210> SEQ ID NO 121
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gctcagcagc cagttgtgcc agcaccagtt gttgaagatg ctgtccttct tccactggat    60

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
aactggtgct ggcacaactg gctgctgagc tgccgccgca tgcgcatcga cccctacctg    60

<210> SEQ ID NO 123
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ccacttgctc ttcaccttgg tgcaggggct caggtagggg tcgatgcgca tgcggcggca    60

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
agcccctgca ccaaggtgaa gagcaagtgg atcaaggagc tgcacatcaa gcccgagacc    60

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cttgcccacc ttctcctcga tcagcttcag ggtctcgggc ttgatgtgca gctccttgat    60

<210> SEQ ID NO 126
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctgaagctga tcgaggagaa ggtgggcaag agcctggagg acatgggcac cggcgagaag    60

<210> SEQ ID NO 127
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggcacaggcc atggcggtgc ggttcaggaa cttctcgccg gtgcccatgt cctccaggct    60

<210> SEQ ID NO 128
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttcctgaacc gcaccgccat ggcctgtgcc gtgcgcagcc ggatcgataa gtgggacctg    60

<210> SEQ ID NO 129
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cttggcctta cagaaggact gcagcttcat caggtcccac ttatcgatcc ggctgcgcac    60

<210> SEQ ID NO 130
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
atgaagctgc agtccttctg taaggccaag gataccgtgt acaagaccaa gcgccccccg    60

<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggggtaggtg aagatgcgct cccagtcggt cgggggcgc ttggtcttgt acacggtatc    60

<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
accgactggg agcgcatctt cacctacccc aagagcgacc gcggcctgat cagcaacatc    60

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
gcgcaggtcc accttcttca gctccttgta gatgttgctg atcaggccgc ggtcgctctt    60

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
tacaaggagc tgaagaaggt ggacctgcgc aagagcaaca cccgctgaa gaagtggggc    60

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135 ctcggggag aactccttgt tcagctcgga gccccacttc ttcagcgggt tgttgctctt    60

<210> SEQ ID NO 136
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
tccgagctga acaaggagtt ctcccccgag gagtaccgca tggccgagaa gcacctgaag    60

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
ctcgcggatg atcaggctgg tgctgcactt cttcaggtgc ttctcggcca tgcggtactc    60

```
<210> SEQ ID NO 138
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
aagtgcagca ccagcctgat catccgcgag atgcagatca agaccaccct gcgcttccac    60

<210> SEQ ID NO 139
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cttgatcttg gccatccgca cgggggtcag gtggaagcgc agggtggtct tgatctgcat    60

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140 ctgaccccg tgcggatggc caagatcaag aacagcggcg actcgcgatg ctggcggggc    60

<210> SEQ ID NO 141
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcagtgcagc agggtgccgc gctcgccgca gccccgccag catcgcgagt cgccgctgtt    60

<210> SEQ ID NO 142
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tgcggcgagc gcggcaccct gctgcactgc tggtgggact gtcgcctggt ccagcccctg    60

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cttccgcagg aaccgccaca cgctcttcca caggggctgg accaggcgac agtcccacca    60

<210> SEQ ID NO 144
```

<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tggaagagcg tgtggcggtt cctgcggaag ctggacatcg tgctgcccga ggaccccgcc    60

<210> SEQ ID NO 145
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctcctcgggg tagatgccca gcaggggat ggcggggtcc tcgggcagca cgatgtccag    60

<210> SEQ ID NO 146
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146 atcccctgc tgggcatcta ccccgaggag gcccccaccg gcaagaagga cacctgcagc    60

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gatgatgaac agggcggcga tgaacatggt gctgcaggtg tccttcttgc cggtggggc    60

<210> SEQ ID NO 148
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
accatgttca tcgccgccct gttcatcatc gcccgcaact ggaaggagcc ccgctgcccc    60

<210> SEQ ID NO 149
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccacatcttc tgaatccact cctcggtgct ggggcagcgg ggctccttcc agttgcgggc    60

<210> SEQ ID NO 150
<211> LENGTH: 60

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
agcaccgagg agtggattca gaagatgtgg tacatctaca ccatggagta ctacagcgcc    60

<210> SEQ ID NO 151
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
caggaacttc atgaactcgt tcttcttgat ggcgctgtag tactccatgg tgtagatgta    60

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
atcaagaaga acgagttcat gaagttcctg gccaagtgga tggacctgga gagcatcatc    60

<210> SEQ ID NO 153
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gttgcgctgg ctctgggtca cctcgctcag gatgatgctc tccaggtcca tccacttggc    60

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctgagcgagg tgacccagag ccagcgcaac agccacaaca tgtacagcct gatcagcggg    60

<210> SEQ ID NO 155
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atcgtgggta tcaccggttt tgggctagta cccgctgatc aggctgtaca tgttgtggct    60

<210> SEQ ID NO 156
<211> LENGTH: 60
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 156
tactagccca aaaccggtga tacccacgat ataagataca attgcctaaa cacatgaaac    60

<210> SEQ ID NO 157
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgtccacact tcagtcttca tttttcttga gtttcatgtg tttaggcaat tgtatcttat    60

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tcaagaaaaa tgaagactga agtgtggaca ctatgcccct ccttagaagt gggaacaaaa    60

<210> SEQ ID NO 159
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
actttgtttc tgtaactcct tccatggctg ttttgttccc acttctaagg aggggcatag    60

<210> SEQ ID NO 160
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cagccatgga aggagttaca gaaacaaagt ttggagctga gatgaaagga gggaccatgt    60

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tggggtggaa ccctggatat ggcagtctct acatggtccc tcctttcatc tcagctccaa    60

<210> SEQ ID NO 162
<211> LENGTH: 60
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 162
agagactgcc atatccaggg ttccacccca taatcagcat ccaagctctg acaccattgc    60

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggtcctttcg ataaaatctt cctagtatat gcaatggtgt cagagcttgg atgctgatta    60

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
atatactagg aagattttat cgaaaggacc cagatgtagc tgtctcttgt gagactatgc    60

<210> SEQ ID NO 165
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
agcatccact tctgtgtttg ctaggccccg gcatagtctc acaagagaca gctacatctg    60

<210> SEQ ID NO 166
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cggggcctag caaacacaga agtggatgct cacagtcagc taatggatgg atcacagggc    60

<210> SEQ ID NO 167
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgggtacttt ctctagctcc tccattgaaa gccctgtgat ccatccatta gctgactgtg    60

<210> SEQ ID NO 168
<211> LENGTH: 60
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 168
tttcaatgga ggagctagag aaagtaccca aggagctaaa gggatctgca actctatagg    60

<210> SEQ ID NO 169
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gggtactggt taactcataa tgttgttcca cctatagagt tgcagatccc tttagctcct    60

<210> SEQ ID NO 170
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tggaacaaca ttatgagtta accagtaccc ctgagctctt gacgctagct gcatatgtat    60

<210> SEQ ID NO 171
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tccagtgatg accgactagg ccatcttttg atacatatgc agctagcgtc aagagctcag    60

<210> SEQ ID NO 172
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
caaaagatgg cctagtcggt catcactgga aagagaggcc cattggacac gcagactttg    60

<210> SEQ ID NO 173
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggccctggcg ttccactgta ccggggcaca caaagtctgc gtgtccaatg ggcctctctt    60

<210> SEQ ID NO 174
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
tgtgccccgg tacagtggaa cgccagggcc aaggggggg gagtgggtgg gtaggggagt    60

<210> SEQ ID NO 175
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
accaaaagtc cccttaccc acccaccccc actccctac ccacccactc cccccttt    60

<210> SEQ ID NO 176
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gggggtgggt gggtaagggg gacttttggt atagcattgg aaatgtaaat gagctaaata    60

<210> SEQ ID NO 177
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gggtcgacgg atcctttatt aggtatttag ctcatttaca tttccaatgc tat    53

<210> SEQ ID NO 178
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gcgaattcgg cgcgccgcca ccatggccaa gggcaagcgc cgcaacctga ccaaccgcaa    60

<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggtgggggtg ctgggctcgg ggctggggct gtggtcctgg ttgcggttgg tcaggttgcg    60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ccgagcccag cacccccacc agcccagcc ccggcaaccc caacacccc gagaacctgg    60

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tcctccacca tcatcatcag gtaggccttc aggtccaggt ccaggttctc ggggtgttg    60

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ctgatgatga tggtggagga catcaagaag gacttcaaca agagcctgaa ggagatccag    60

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcttctcctt cagcacctgc agctccttgg cggtgttctc ctggatctcc ttcaggctct    60

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcaggtgctg aaggagaagc aggagaacac catcaagcag gtggaggtgc tgaccgagaa    60

<210> SEQ ID NO 185
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cttgttcatc tccatcacct gcttgtaggt cttctcctcc ttctcggtca gcacctccac    60

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aggtgatgga gatgaacaag accatcctgg acctgaagcg                    40

<210> SEQ ID NO 187
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cggaattcgt cgacctcgcg cttcaggtcc aggatggt                      38

<210> SEQ ID NO 188
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gcgaattcgt cgacaccatc aagaagaccc agagcgaggc cacc                44

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cgatggtgcc gctcttcttg cccagggtct cgatctccag ggtggcctcg ctctgggtct    60

<210> SEQ ID NO 190
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
caagaagagc ggcaccatcg acctgagcat cagcaaccgc atccaggaga tggaggagcg    60

<210> SEQ ID NO 191
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggtgccgatg ttctcgatgc tgtcctcggc gccgctgatg cgctcctcca tctcctggat    60

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gcatcgagaa catcggcacc accatcaagg agaacggcaa gtgcaagaag atcctgaccc    60

<210> SEQ ID NO 193
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ttggggcggc ggatggtgtc ctggatctcc tggatgttct gggtcaggat cttcttgcac    60

<210> SEQ ID NO 194
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gacaccatcc gccgcccaa cgtgcgcatc atcggcgtgg acgagaacga ggacttccag    60

<210> SEQ ID NO 195
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cctcgatgat cttgttgaag atgttggcgg ggcccttcag ctggaagtcc tcgttctcgt    60

<210> SEQ ID NO 196
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cttcaacaag atcatcgagg agaacttccc caacctgaag aacgagatgc acatgaacat    60

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gggtgcggta ggcctcctgg atgttcatgt gcatctcgtt                          40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ccaggaggcc taccgcaccc ccaaccgcct ggaccagaag            40

<210> SEQ ID NO 199
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cggaattctc tagagctgtt gcgcttctgg tccaggcggt tgg            43

<210> SEQ ID NO 200
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gcgaattctc tagacacatc atcatccgca ccagcaacgc cctgaacaag gaccgcatc            59

<210> SEQ ID NO 201
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ccttgtaggt cacctggccc ttctcgcgca cggccttcag gatgcggtcc ttgttcaggg            60

<210> SEQ ID NO 202
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gggccaggtg acctacaagg gcaagcccat ccgcatcacc cccgacttca gccccgagac            60

<210> SEQ ID NO 203
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggtctggatc acgtcggtcc aggcgcggcg ggccttcatg gtctcgggc tgaagtcggg            60

<210> SEQ ID NO 204
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggaccgacgt gatccagacc ctgcgcgagc acaagctgca gccccgcctg ctgtaccccg            60

<210> SEQ ID NO 205
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aacaccttgg tctcgccctc gatgatgatg ctcagcttgg cggggtacag caggcggggc    60

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gagggcgaga ccaaggtgtt ccacgacaag accaagttca cccactacct gagcaccaac    60

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tgtactggtt cttctcggtg atgatgcgct gcagggcggg gttggtgctc aggtagtggg    60

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
caccgagaag aaccagtaca agaacggcaa caacgccctg gagaagaccc gccgctaatc    60

<210> SEQ ID NO 209
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cggaattctt aattaaggtt tgttgaggga ttagcggcgg gtcttctc    48

<210> SEQ ID NO 210
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gcgaattcgc ggccgcgttt aaacttaatt aagccaccat gggca    45

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 211
tgttgccggt cttgcggttc tgcttcttgc ccatggtggc ttaat    45

<210> SEQ ID NO 212
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
accgcaagac cggcaacagc aagacccaga gcgccagccc ccccc    45

<210> SEQ ID NO 213
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
tggcggggct gctgctgcgc tccttggggg gggggctggc gctct    45

<210> SEQ ID NO 214
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
gcagcagcag ccccgccacc gagcagagct ggatggagaa cgact    45

<210> SEQ ID NO 215
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
ggaagccctc ctcgcgcagc tcgtcgaagt cgttctccat ccagc    45

<210> SEQ ID NO 216
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 216
tgcgcgagga gggcttccgc cgcagcaact acagcgagct gcgcg    45

-continued

```
<210> SEQ ID NO 217
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cctccttgcc cttggtctgg atgtcctcgc gcagctcgct gtagt             45

<210> SEQ ID NO 218
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
agaccaaggg caaggaggtg gagaacttcg agaagaacct ggagg             45

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cggtgttggt gatgcgggtg atgcactcct ccaggttctt ctcga             45

<210> SEQ ID NO 220
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cccgcatcac caacaccgag aagtgcctga aggagctgat ggagc             45

<210> SEQ ID NO 221
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cgcgcagctc gcgggccttg gtcttcagct ccatcagctc cttca             45

<210> SEQ ID NO 222
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
aggcccgcga gctgcgcgag gagtgccgca gcctgcgcag ccgct             45

<210> SEQ ID NO 223
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gcgaattcaa ttggtcgcag cggctgcgca ggctgc                        36

<210> SEQ ID NO 224
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcgaattcaa ttggaggagc gcgtgagcgc catggaggac gagat              45

<210> SEQ ID NO 225
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aacttgccct cgcgcttcat ctcgttcatc tcgtcctcca tggcg              45

<210> SEQ ID NO 226
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gaagcgcgag ggcaagttcc gcgagaagcg catcaagcgc aacga              45

<210> SEQ ID NO 227
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tagtcccaga tctcctgcag gctctgctcg ttgcgcttga tgcgc              45

<210> SEQ ID NO 228
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gcaggagatc tgggactacg tgaagcgccc caacctgcgc ctgat              45

<210> SEQ ID NO 229
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ttctccacgt cgctctcggg cacgccgatc aggcgcaggt tgggg            45

<210> SEQ ID NO 230
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
cgagagcgac gtggagaacg gcaccaagct ggagaacacc ctgca            45

<210> SEQ ID NO 231
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ttggggaagt tctcctggat gatgtcctgc agggtgttct ccagc            45

<210> SEQ ID NO 232
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ccaggagaac ttccccaacc tggcccgcca ggccaacgtg cagat            45

<210> SEQ ID NO 233
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
cgctgggggg tgcgctggat ctcctggatc tgcacgttgg cctgg            45

<210> SEQ ID NO 234
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ccagcgcacc ccccagcgct acagcagccg ccgcgccacc ccccg            45

<210> SEQ ID NO 235
<211> LENGTH: 45
<212> TYPE: DNA
```

<210> SEQ ID NO 235
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
accttggtga agcgcacgat gatgtggcgg ggggtggcgc ggcgg          45

<210> SEQ ID NO 236
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
cgtgcgcttc accaaggtgg agatgaagga gaagatgctg cgcgc          45

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237
agggtcacgc ggcccttctc gcgggcggcg cgcagcatct tctcc          45

<210> SEQ ID NO 238
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
gaagggccgc gtgaccctga agggcaagcc catccgtctc accgc          45

<210> SEQ ID NO 239
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 239
gcgaattcgg cggtgagacg gatgggc          27

<210> SEQ ID NO 240
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 240
gcgaattcgt ctcaccgccg acctgagcgc cgagaccctg caggc          45

<210> SEQ ID NO 241
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 241
ttgaagatgg ggccccactc gcggcgggcc tgcagggtct cggcg         45

<210> SEQ ID NO 242
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 242
gtggggcccc atcttcaaca tcctgaagga gaagaacttc cagcc         45

<210> SEQ ID NO 243
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 243
ctcagcttgg cggggtagct gatgcggggc tggaagttct tctcc         45

<210> SEQ ID NO 244
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 244
ctaccccgcc aagctgagct tcatcagcga gggcgagatc aagta         45

<210> SEQ ID NO 245
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 245
tcgcgcagca tctgcttgtc gatgaagtac ttgatctcgc cctcg         45

<210> SEQ ID NO 246
<211> LENGTH: 45
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 246
caagcagatg ctgcgcgact tcgtgaccac ccgccccgcc ctgaa         45

<210> SEQ ID NO 247
<211> LENGTH: 45
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 247
atgttcaggg cctccttcag cagctccttc agggcggggc gggtg            45

<210> SEQ ID NO 248
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gaaggaggcc ctgaacatgg agcgcaacaa ccgctaccag cccct            45

<210> SEQ ID NO 249
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ggtctttaca tcttggcgtg gttctgcagg ggctggtagc ggttg            45

<210> SEQ ID NO 250
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cgccaagatg taaagaccat cgagactagg aagaaactgc atcaa            45

<210> SEQ ID NO 251
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
atgggcgcgc ctgattttgc tcattagttg atgcagtttc ttcct            45

<210> SEQ ID NO 252
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
aaaatcaggc gcgcccatca taatgaccgg cagcaacagc cacat            45

<210> SEQ ID NO 253
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253
gcgaattcat gtggctgttg ctgccgg    27

<210> SEQ ID NO 254
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gcgaattcgg cgcgcccatc ataatgaccg gcagcaacag ccaca    45

<210> SEQ ID NO 255
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
cgttgatgtt cagggtcagg atggtgatgt ggctgttgct gccgg    45

<210> SEQ ID NO 256
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tgaccctgaa catcaacggc ctgaacagcg ccatcaagcg ccacc    45

<210> SEQ ID NO 257
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
cctggctctt gatccagctg gccaggcggt ggcgcttgat ggcgc    45

<210> SEQ ID NO 258
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gctggatcaa gagccaggac cccagcgtgt gctgcatcca ggaga    45

<210> SEQ ID NO 259
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggtgggtgtc gcggcaggtc aggtgggtct cctggatgca gcaca                45

<210> SEQ ID NO 260
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
cctgccgcga cacccaccgc ctgaagatca agggctggcg caaga                45

<210> SEQ ID NO 261
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tcttctgctt gccgttggcc tggtagatct tgcgccagcc cttga                45

<210> SEQ ID NO 262
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ccaacggcaa gcagaagaag gccggcgtgg ccatcctggt gagcg                 45

<210> SEQ ID NO 263
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tcttggtggg cttgaagtcg gtcttgtcgc tcaccaggat ggcca                45

<210> SEQ ID NO 264
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
acttcaagcc caccaagatc aagcgcgaca aggagggcca ctaca                45

<210> SEQ ID NO 265
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cctgctggat gctgcccttc accatgatgt agtggccctc cttgt                45

<210> SEQ ID NO 266
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
agggcagcat ccagcaggag gagctgacca tcctgaacat ctacg                45

<210> SEQ ID NO 267
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gcgaattcac cggtgttggg ggcgtagatg ttcaggatgg                      40

<210> SEQ ID NO 268
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gcgaattcac cggtgccccc cgcttcatca agcaggtgct gagcg                45

<210> SEQ ID NO 269
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tgtggctgtc caggtcgcgc tgcaggtcgc tcagcacctg cttga                45

<210> SEQ ID NO 270
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gcgacctgga cagccacacc ctgatcatgg gcgacttcaa caccc                45

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gggtgctgcg gtccagggtg ctcaggggg tgttgaagtc gccca    45

<210> SEQ ID NO 272
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ccctggaccg cagcacccgc cagaaggtga acaaggacac ccagg    45

<210> SEQ ID NO 273
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
cggcctggtg cagggcgctg ttcagctcct gggtgtcctt gttca    45

<210> SEQ ID NO 274
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gcgccctgca ccaggccgac ctgatcgaca tctaccgcac cctgc    45

<210> SEQ ID NO 275
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
agaaggtgta ctcggtgctc ttggggtgca gggtgcggta gatgt    45

<210> SEQ ID NO 276
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gcaccgagta caccttcttc agcgcccccc accacaccta cagca    45

<210> SEQ ID NO 277
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ccttgctgcc cacgatgtgg tcgatcttgc tgtaggtgtg gtggg    45

<210> SEQ ID NO 278
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
acatcgtggg cagcaaggcc ctgctgagca agtgcaagcg caccg    45

<210> SEQ ID NO 279
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ggtcgctcag gtagttggtg atgatctcgg tgcgcttgca cttgc    45

<210> SEQ ID NO 280
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccaactacct gagcgaccac agcgccatca agctggagct gcgca    45

<210> SEQ ID NO 281
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tgctgcggct ctgggtcagg ttcttgatgc gcagctccag cttga    45

<210> SEQ ID NO 282
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tgacccagag ccgcagcacc acctggaagc tgaacaacct gctgc    45

<210> SEQ ID NO 283
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tctcgttgtg cacccagtag tcgttcagca gcaggttgtt cagct    45

<210> SEQ ID NO 284
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
actgggtgca caacgagatg aaggccgaga tcaagatgtt cttcg                45

<210> SEQ ID NO 285
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gcgaattcga agaacatctt gatct                                       25

<210> SEQ ID NO 286
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gcgaattctt cgaaccaac gagaacaagg acaccaccta ccaga                 45

<210> SEQ ID NO 287
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
acacggcctt gaaggcgtcc cacaggttct ggtaggtggt gtcct                45

<210> SEQ ID NO 288
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
acgccttcaa ggccgtgtgc cgcggcaagt tcatcgccct gaacg                45

<210> SEQ ID NO 289
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tgctgcgctc ctgcttgcgc ttgtaggcgt tcagggcgat gaact                45

<210> SEQ ID NO 290
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gcaagcagga gcgcagcaag atcgacaccc tgaccagcca gctga            45

<210> SEQ ID NO 291
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gggtctgctc ctgcttctcc agctccttca gctggctggt caggg            45

<210> SEQ ID NO 292
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
agaagcagga gcagacccac agcaaggcca gccgccgcca ggaga            45

<210> SEQ ID NO 293
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ccttcagctc ggcgcggatc ttggtgatct cctggcggcg gctgg             45

<210> SEQ ID NO 294
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tccgcgccga gctgaaggag atcgagaccc agaagaccct gcaga             45

<210> SEQ ID NO 295
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gcgaattcgc gactcgttga tcttctgcag ggtcttctgg g                 41

```
<210> SEQ ID NO 296
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gcgaattctc gcgaagctgg ttcttcgagc gcatcaacaa gatcg            45

<210> SEQ ID NO 297
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tcttgatcag gcgggccagg gggcggtcga tcttgttgat gcgct            45

<210> SEQ ID NO 298
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tggcccgcct gatcaagaag aagcgcgaga agaaccagat cgaca            45

<210> SEQ ID NO 299
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tgatgtcgcc cttgtcgttc ttgatggtgt cgatctggtt cttct            45

<210> SEQ ID NO 300
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
acgacaaggg cgacatcacc accgacccca ccgagatcca gacca            45

<210> SEQ ID NO 301
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
acaggtgctt gtagtactcg cggatggtgg tctggatctc ggtgg            45

<210> SEQ ID NO 302
```

<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
agtactacaa gcacctgtac gccaacaagc tggagaacct ggagg            45

<210> SEQ ID NO 303
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
tgtaggtgtc caggaaggtg tccatctcct ccaggttctc cagct            45

<210> SEQ ID NO 304
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ccttcctgga cacctacacc ctgccccgcc tgaaccagga ggagg            45

<210> SEQ ID NO 305
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
cggtgatggg gcggttcagg ctctccacct cctcctggtt caggc            45

<210> SEQ ID NO 306
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tgaaccgccc catcaccggc agcgagatcg tggccatcat caaca            45

<210> SEQ ID NO 307
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggccggggct cttcttggtg ggcaggctgt tgatgatggc cacga            45

<210> SEQ ID NO 308
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ccaagaagag ccccggcccc gacggcttca ccgccgagtt ctacc            45

<210> SEQ ID NO 309
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
agggcaccag ctcctccttg tagcgctggt agaactcggc ggtga            45

<210> SEQ ID NO 310
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
aggaggagct ggtgcccttc ctgctgaagc tgttccagag catcg            45

<210> SEQ ID NO 311
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
agctgttggg caggatgccc tccttctcga tgctctggaa cagct            45

<210> SEQ ID NO 312
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gcatcctgcc caacagcttc tacgaggcca gcatcatcct gatcc            45

<210> SEQ ID NO 313
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcttggtggt gtcgcggccg ggcttgggga tcaggatgat gctgg            45

<210> SEQ ID NO 314
<211> LENGTH: 45
<212> TYPE: DNA
```

<213> ORGANISM: Artificial Sequence
<220> FEATURE:
<223> OTHER INFORMATION: Description of Artificial Sequence: Synthetic
    oligonucleotide

<400> SEQUENCE: 314
gccgcgacac caccaagaag gagaacttcc gccccatcag cctga                45

<210> SEQ ID NO 315
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 315
tgttcaggat cttggcgtcg atgttcatca ggctgatggg gcgga                45

<210> SEQ ID NO 316
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 316
acgccaagat cctgaacaag atcctggcca accgcatcca gcagc                45

<210> SEQ ID NO 317
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 317
ggtcgtggtg gatcagcttc ttgatgtgct gctggatgcg gttgg                45

<210> SEQ ID NO 318
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 318
agctgatcca ccacgaccag gtgggcttca tccccgggat gcagg                45

<210> SEQ ID NO 319
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 319
gcgaattccc tgcatcccgg ggatga                                     26

<210> SEQ ID NO 320
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gcgaattccc cgggatgcag ggctggttca acatccgcaa gagca                45

<210> SEQ ID NO 321
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cgcggttgat gtgctggatc acgttgatgc tcttgcggat gttga                45

<210> SEQ ID NO 322
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tccagcacat caaccgcgcc aaggacaaga accacatgat catca                45

<210> SEQ ID NO 323
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tgtcgaaggc cttctcggcg tcgatgctga tgatcatgtg gttct                45

<210> SEQ ID NO 324
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ccgagaaggc cttcgacaag atccagcagc ccttcatgct gaaga                45

<210> SEQ ID NO 325
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tgccgtcgat gcccagcttg ttcagggtct tcagcatgaa gggct                45

<210> SEQ ID NO 326
<211> LENGTH: 45
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 326
agctgggcat cgacggcacc tacttcaaga tcatccgcgc catct              45

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ggatgatgtt ggcggtgggc ttgtcgtaga tggcgcggat gatct              45

<210> SEQ ID NO 328
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ccaccgccaa catcatcctg aacggccaga agctggaggc cttcc              45

<210> SEQ ID NO 329
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
cgaattcacg cgtgccggtc ttcaggggga aggcctccag cttct              45

<210> SEQ ID NO 330
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gcgaattcac gcgtcagggc tgcccoctga gcccoctgct gttca              45

<210> SEQ ID NO 331
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
cgcgggccag cacctccagc acgatgttga acagcagggg gctca              45

<210> SEQ ID NO 332
<211> LENGTH: 45
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 332
tggaggtgct ggcccgcgcc atccgccagg agaaggagat caagg            45

<210> SEQ ID NO 333
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tcacctcctc cttgcccagc tggatgccct tgatctcctt ctcct            45

<210> SEQ ID NO 334
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgggcaagga ggaggtgaag ctgagcctgt tcgccgacga catga            45

<210> SEQ ID NO 335
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
tcacgatggg gttctccagg tacacgatca tgtcgtcggc gaaca            45

<210> SEQ ID NO 336
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tggagaaccc catcgtgagc gcccagaacc tgctgaagct gatca            45

<210> SEQ ID NO 337
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tgtagccgct caccttgctg aagttgctga tcagcttcag caggt            45

<210> SEQ ID NO 338
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gcaaggtgag cggctacaag atcaacgtgc agaagagcca ggcct                45

<210> SEQ ID NO 339
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
cggtctggcg gttgttggtg tacaggaagg cctggctctt ctgca                45

<210> SEQ ID NO 340
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ccaacaaccg ccagaccgag agccagatca tgggcgagct gccct                45

<210> SEQ ID NO 341
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gcgaattcgc tagcgatggt gaagggcagc tcgcccatga                      40

<210> SEQ ID NO 342
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gcgaattcgc tagcaagcgc atcaagtacc tgggcatcca gctga                45

<210> SEQ ID NO 343
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
ccttgaacag gtccttcacg tcgcgggtca gctggatgcc caggt                45

<210> SEQ ID NO 344
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tgaaggacct gttcaaggag aactacaagc ccctgctgaa ggaga            45

<210> SEQ ID NO 345
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tcttccactt gttggtctcc tccttgatct ccttcagcag gggct            45

<210> SEQ ID NO 346
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
agaccaacaa gtggaagaac atccctgca gctgggtggg ccgca             45

<210> SEQ ID NO 347
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gcaggatggc catcttcacg atgttgatgc ggcccaccca gctgc            45

<210> SEQ ID NO 348
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tgaagatggc catcctgccc aaggtgatct accgcttcaa cgcca            45

<210> SEQ ID NO 349
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agaaggtcat gggcagcttg atggggatgg cgttgaagcg gtaga            45

<210> SEQ ID NO 350
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
agctgcccat gaccttcttc accgagctgg agaagaccac cctga 45

<210> SEQ ID NO 351
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gggcgcgctt ctggttccag atgaacttca gggtggtctt ctcca 45

<210> SEQ ID NO 352
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ggaaccagaa gcgcgcccgc atcgccaaga gcatcctgag ccaga 45

<210> SEQ ID NO 353
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gcagggtgat gccgccggcc ttgttcttct ggctcaggat gctct 45

<210> SEQ ID NO 354
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ccggcggcat caccctgccc gacttcaagc tgtactacaa ggcca 45

<210> SEQ ID NO 355
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
accagtacca ggcggtcttg gtcacggtgg ccttgtagta cagct 45

<210> SEQ ID NO 356
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
agaccgcctg gtactggtac cagaaccgcg atatcgacca gtgga    45

<210> SEQ ID NO 357
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gcgaattcca ctggtcgata tcgcgg    26

<210> SEQ ID NO 358
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gcgaattcga tatcgaccag tggaaccgca ccgagcccag cgaga    45

<210> SEQ ID NO 359
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tcaggtagtt gtagatgtgg ggcatgatct cgctgggctc ggtgc    45

<210> SEQ ID NO 360
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
acatctacaa ctacctgatc ttcgacaagc ccgagaagaa caagc    45

<210> SEQ ID NO 361
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tgttgaacag gctgtccttg ccccactgct tgttcttctc gggct    45

<210> SEQ ID NO 362
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
aggacagcct gttcaacaag tggtgctggg agaactggct ggcca    45

<210> SEQ ID NO 363
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
aggggtccag cttcagcttg cggcagatgg ccagccagtt ctccc            45

<210> SEQ ID NO 364
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
agctgaagct ggaccccttc ctgaccccct acaccaagat caaca            45

<210> SEQ ID NO 365
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tcacgttcag gtccttgatc cagcggctgt tgatcttggt gtagg            45

<210> SEQ ID NO 366
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tcaaggacct gaacgtgaag cccaagacca tcaagaccct ggagg            45

<210> SEQ ID NO 367
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgtcctggat ggtgatgccc aggttctcct ccagggtctt gatgg            45

<210> SEQ ID NO 368
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gcatcaccat ccaggacatc ggcgtgggca aggacttcat gagca            45

<210> SEQ ID NO 369
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ccttggtggc catggccttg ggggtcttgc tcatgaagtc cttgc              45

<210> SEQ ID NO 370
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
aggccatggc caccaaggac aagatcgaca agtgggacct gatca              45

<210> SEQ ID NO 371
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
ccttggcggt gcagaagctc ttcagcttga tcaggtccca cttgt              45

<210> SEQ ID NO 372
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gcttctgcac cgccaaggag accaccatcc gcgtgaaccg ccagc              45

<210> SEQ ID NO 373
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tggcgaagat cttctcccag gtggtgggct ggcggttcac gcgga              45

<210> SEQ ID NO 374
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gggagaagat cttcgccacc tacagcagcg acaagggcct gatca              45

```
<210> SEQ ID NO 375
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tctgcttcag ctcgttgtag atgcggctga tcaggccctt gtcgc            45

<210> SEQ ID NO 376
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
acaacgagct gaagcagatc tacaagaaga agaccaacaa cccca            45

<210> SEQ ID NO 377
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggttcatgtc cttggcccac ttcttgatgg ggttgttggt cttct            45

<210> SEQ ID NO 378
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gggccaagga catgaaccgc cacttcagca aggaggacat ctacg            45

<210> SEQ ID NO 379
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gcgaattcat atgcttcttg gcggcgtaga tgtcctcctt gc               42

<210> SEQ ID NO 380
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gcgaattcat atgaagaagt gcagcagcag cctggccatc cgcga            45

<210> SEQ ID NO 381
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
tagcgcatgg tggtcttgat ctgcatctcg cggatggcca ggctg            45

<210> SEQ ID NO 382
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
caagaccacc atgcgctacc acctgacccc cgtgcgcatg gccat            45

<210> SEQ ID NO 383
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
cagcggttgt tgccgctctt cttgatgatg gccatgcgca cgggg            45

<210> SEQ ID NO 384
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gagcggcaac aaccgctgct ggcgcggctg cggcgagatc ggcac            45

<210> SEQ ID NO 385
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
ttgcagtccc accagcagtg cagcagggtg ccgatctcgc cgcag            45

<210> SEQ ID NO 386
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctgctggtgg gactgcaagc tggtgcagcc cctgtggaag agcgt            45

<210> SEQ ID NO 387
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
agctccaggt cgcgcaggaa gcgccacacg ctcttccaca ggggc          45

<210> SEQ ID NO 388
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
cctgcgcgac ctggagctgg agatcccctt cgaccccgcc atccc          45

<210> SEQ ID NO 389
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tactcgttgg ggtagatgcc cagcaggggg atggcggggt cgaag          45

<210> SEQ ID NO 390
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
catctacccc aacgagtaca agagctgctg ctacaaggac acctg          45

<210> SEQ ID NO 391
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
aacagggcgg cgatgaacat gcgggtgcag gtgtccttgt agcag          45

<210> SEQ ID NO 392
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gttcatcgcc gccctgttca ccatcgccaa gacctggaac cagcc          45

<210> SEQ ID NO 393
<211> LENGTH: 45
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 393
atccaatcga tcatggtggg gcacttgggc tggttccagg tcttg          45

<210> SEQ ID NO 394
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
caccatgatc gattggatca agaagatgtg gcacatctac accat          45

<210> SEQ ID NO 395
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcgaattcat ggtgtagatg tgccac          26

<210> SEQ ID NO 396
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gcgctcgaga tcgattggat caagaagatg tggcacatct acacc          45

<210> SEQ ID NO 397
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gttcttgatg gcggcgtagt actccatggt gtagatgtgc cacat          45

<210> SEQ ID NO 398
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tacgccgcca tcaagaacga cgagttcatc agcttcgtgg gcacc          45

<210> SEQ ID NO 399
<211> LENGTH: 45
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 399
caggatgatg gtctccagct tcatccaggt gcccacgaag ctgat            45

<210> SEQ ID NO 400
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ctggagacca tcatcctgag caagctgagc caggagcaga agacc            45

<210> SEQ ID NO 401
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gccgatcagg ctgaagatgc ggtgcttggt cttctgctcc tggct            45

<210> SEQ ID NO 402
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
atcttcagcc tgatcggcgg caactgagta tacggatccg aattc            45

<210> SEQ ID NO 403
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
agcgctcgag aattcggatc cgtatac                                27

<210> SEQ ID NO 404
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ccattttaca tcttggcgtg gttctgcagg ggctggtagc ggttg            45

<210> SEQ ID NO 405
<211> LENGTH: 45
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 405
cgccaagatg taaaatggtt ttatactcta atcactgcta attat              45

<210> SEQ ID NO 406
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gaaggcgcgc ctagtcaaat aaaagaaata attagcagtg attag              45

<210> SEQ ID NO 407
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ttgactaggc gcgccttcaa ttatgaccgg cagcaacagc cacat              45

<210> SEQ ID NO 408
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
gcgaattcga tgtggctgtt gctgccg                                  27

<210> SEQ ID NO 409
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
gcgaattcgg cgcgccttca attatgaccg gcagcaacag ccaca              45

<210> SEQ ID NO 410
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gtggcggccg cggcgcgcct cgcgagctag cgcatatgct cgagcgc            47

<210> SEQ ID NO 411
<211> LENGTH: 47
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 411
ggcgctcgag catatgcgct agctcgcgag gcgcgccgcg gccgcca                          47

<210> SEQ ID NO 412
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
gccttactag aaactataac ttgaaaacta taac                                        34

<210> SEQ ID NO 413
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
agaaaatttg tctcttgctg ttgttaaact c                                           31

<210> SEQ ID NO 414
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
atggttgtca gataagtgga ttgatgaagt                                             30

<210> SEQ ID NO 415
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
aggaattcaa aaccattac gtttatactt c                                            31

<210> SEQ ID NO 416
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
taaaaaccag aatttccatt aggaaaagaa g                                           31

<210> SEQ ID NO 417
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
acaagagaaa ctacaagaaa atactcttga gcta        34

<210> SEQ ID NO 418
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ggatacagag attcagttct gcaaagaatt gcaaatt        37

<210> SEQ ID NO 419
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
aaaaaaccag aatttccatt aggaaaagaa gaca        34

<210> SEQ ID NO 420
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
agagaaacta caagaaaata ctcttgagct agga        34

<210> SEQ ID NO 421
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
tacagagatt cagttctgca aagaattgca aattagttaa a        41

<210> SEQ ID NO 422
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ttaaaagcac cacttattgg atagtttatt aaatgc        36

<210> SEQ ID NO 423
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 423
atgcaagtat ctgtatatga tttcttcagc atatgtgt                                38

<210> SEQ ID NO 424
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gtttaaggca acatgagaga gagccagaga caggaa                                  36

<210> SEQ ID NO 425
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
aaaaagcacc acttattgga tagtttatta aatgcatg                                38

<210> SEQ ID NO 426
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
caagtatctg tatatgattt cttcagcata tgtgtgtt                                38

<210> SEQ ID NO 427
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
taaggcaaca tgagagagag ccagagacag gaaagctgtc c                            41

<210> SEQ ID NO 428
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
cactaaagaa aagcttgaag acatagaata cctggaaac                               39

<210> SEQ ID NO 429
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
```

```
aagaatacct ggaaacatac ctttcaaaat tc                                   32
```

<210> SEQ ID NO 430
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430

```
ttagatataa aaataaccaa atgatacaa                                       29
```

<210> SEQ ID NO 431
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431

```
aataaaaata accaaatgat acaattatgt                                      30
```

<210> SEQ ID NO 432
<211> LENGTH: 5002
<212> TYPE: DNA
<213> ORGANISM: Mus sp.

<400> SEQUENCE: 432

```
atggcgaaag gtaaacggag gaatcttact aacaggaacc aagaccactc accatcacca      60
gaacccagca cacccacttc gcccagtcca gggaacccca acacacctga gaacctagac     120
ctagatttaa aagcatatct catgatgatg gtagagggca tcaagaagga ctttaataaa     180
tcacttaaag aaatacagga gaacactgct aaagagttac aagtccttaa agaaaaacag     240
gaaaacacaa tcaaacaggt agaagtcctt acagaaaaag aggaaaaaac atacaaacag     300
gtgatggaaa tgaacaaaac catactagac ctaaaaaggg aagtagacac aataaagaaa     360
actcaaagcg aggcaacact agagatagaa accctaggaa gaaatctgg  aaccatagat     420
ttgagcatca gcaacagaat acaagagatg gaagagagaa tctcaggtgc agaacattcc     480
atagagaaca tcggcacaac aatcaaagaa atggaaaat gcaaaaagat cctaactcaa     540
aatatccagg aaatccagga cacaataaga gaccaaacg tacggataat aggagtggat     600
gagaatgaag attttcaact caaaggtcca gcaaacatct tcaacaaaat tattgaagaa     660
aacttcccaa atctaaagaa tgagatgcat atgaacatac aagaagccta cagaactcca     720
aatagactgg accagaaaag aaattcctcc cgcacacataa taatcagaac atcaaatgca     780
ctaaataaag atagaatact aaaagcagta agggaaaaag gtcaagtaac atataaaggc     840
aagcctatca gaattacacc agatttttca ccagagacta tgaaagccag aagagcctgg     900
acagatgtta tacagacact aagagaacac aaactgcagc ccaggctact atacccagcc     960
aaactctcaa ttatcataga gggagaaacc aaagtattcc acgacaaaac caaattcacg    1020
cattatctct ccacgaatcc agcccttcaa aggataataa cagaaaaaaa ccaatacaag    1080
aacgggaaca acgccctaga aaaacaagaa ggtaatccc tcaacaaacc taaagaagaa    1140
cagccacaag aacagaatgc caccttaac aactaaaata acaggaagca acaattactt    1200
ttccttaata tctcttaaca tcaatggtct caactcgcca ataaaagac atagactaac    1260
```

```
aaactggcta cacaaacaag acccaacatt ttgctgctta caggaaactc atctcagaga    1320
aaaagataga cactacctca gaatgaaagg ctggaaaaca attttccaag caaatggtat    1380
gaagaaacaa gcaggagtag ccatcctaat atctgataag attgacttcc aacccaaagt    1440
catcaaaaaa gacaaggagg gacacttcat tctcatcaaa ggtaaaatcc tccaagagga    1500
actctcaatt ctgaatatct atgctccaaa tacaagagca gccacattca ctaaagaaac    1560
tttagtaaag ctcaaagcac acattgcgcc tcacacaata atagtgggag acttcaacac    1620
accactttca ccaatggaca gatcatggaa acagaaacta aacagggaca cactgaaact    1680
aacagaagtg atgaaacaaa tggatctgac agatatctac agaacatttt accctaaaac    1740
aaaaggatat accttcttct cagcacctca tggtaccttc tccaaaattg accacataat    1800
aggtcacaaa tcaggcctca acagattaaa aaatattgaa attgtcccat gtatcctatc    1860
agatcaccat gcactaaggc tgatcttcaa taacaaaata aataacagaa agccaacatt    1920
cacatggaaa ctgaacaaca ctcttctcaa tgataccttg gtcaaggaag gaataaagaa    1980
agaaattaaa gactttttag agtttaatga aaatgaagcc acaacgtacc caaacctttg    2040
ggacacaatg aaagcatttc taagagggaa actcatagct atgagtgcct tcaagaaaaa    2100
acgggagaga gcacatacta gcagcttgac aacacatcta aaagctctag aaaaaagga    2160 agcaaattca cccaagagga gtagacggca ggaaataatc aaactcaggg gtgaaatcaa    2220
ccaagtggaa caagaagaa ctattcaaag aattaaccaa cgaggagtt ggttctttga    2280 gaaaatcaac aagatagata aacccttagc tagactcact aaagggcaca gggacaaaat    2340
cctaattaac aaaatcagaa atgaaaaggg agacataaca acagatcctg aagaaatcca    2400
aaacaccatc agatccttct acaaaaggct atactcaaca aaactggaaa acctggacga    2460
aatggacaaa tttctggaca gataccaggt accaaagttg aatcaggatc aagttgacct    2520
tctaaacagt cccatatccc ctaaagaaat agaagcagtt attaatagtc tcccagccaa    2580
aaaaagccca ggaccagacg ggtttagtgc agagttctat cagaccttca agaagatct    2640 aactccagtt ctgcacaaac ttttcacaa gatagaagta gaaggtattc tacccaactc    2700
attttatgaa gccactatta ctctgatacc taaaccacag aaagatccaa caaagataga    2760
gaacttcaga ccaatttctc ttatgaacat cgatgcaaaa atccttaata aaattctcgc    2820
taaccgaatc caagaacaca ttaaagcaat catccatcct gaccaagtag gttttattcc    2880
agggatgcag ggatggttta atatacgaaa atccatcaat gtaatccatt atataaacaa    2940
actcaaagac aaaaaccaca tgatcatctc gttagatgca gaaaaagcat ttgacaagat    3000
ccaacaccca ttcatgataa aagttctgga agatcagga attcaaggcc aatacctaaa    3060
catgataaaa gcaatctaca gcaaaccagt agccaacatc aaagtaaatg gagagaagct    3120
ggaagcaatc ccactaaaat caggactag acaaggctgc ccactttctc cctacctttt    3180
caacatagta cttgaagtat tagccagagc aattcgacaa caaaaggaga tcaaggggat    3240
acaaattgga aaagaggaag tcaaaatatc actttttgca gatgatatga tagtatatat    3300
aagtgaccct aaaaattcca acagagaact cctaaacctg ataaacagct cggtgaagt    3360 agctggatat aaaattaact caaacaagtc aatggccttt ctctacacaa agaataaaca    3420
ggctgagaaa gaaattaggg aaacaacacc cttctcaata gccacaaata tataaaata    3480 tctcggcgtg actctaacga aggaagtgaa agatctgtat gataaaaact tcaagtccct    3540
gaagaaagaa attaaagaag atctcagaag atggaaagat ctcccatgct catggattgg    3600
caggaccaac attgtaaaaa tggctatctt gccaaaagca atctacagat tcaatgcaat    3660
```

```
ccccattaaa attccaactc aattcttcaa cgaattagaa ggagcaattt gcaaattcat    3720
ctggaataac aaaaaaccga ggatagcaaa aactcttctc aaggataaaa gaacctctgg    3780
tggaatcacc atgcctgacc taaagcttta ctacagagca attgtgataa aaactgcatg    3840
gtactggtat agagacagac aagtagacca atggaataga attgaagacc agaaatgaa     3900 cccacacacc tatggtcact tgatcttcga caagggagcc aaaaccatcc agtggaagaa    3960
agacagcatt ttcaacaatt ggtgctggca caactggttg ttatcatgta gaagaatgcg    4020
aatcgatcca tacttatctc cttgtactaa ggtcaaatct aagtggatca aggaacttca    4080
cataaaacca gagacactga aacttataga ggagaaagtg gggaaaagtc ttgaagatat    4140
gggcacaggg gaaaaattcc tgaacagaac agcaatggct tgtgctgtaa gatcgagaat    4200
tgacaaatgg gacctaatga aactccaaag tttctgcaag gcaaaagaca ctgtctataa    4260
gacaaaaaga ccaccaacag actgggaaag gatctttacc tatcctaaat cagataggg    4320 actaatatcc aacatatata aagaactcaa gaaggtggac ctcagaaaat caaataaccc    4380
ccttaaaaaa tggggctcag aactgaacaa agaattctca cctgaggaat accgaatggc    4440
agagaagcac ctgaaaaaat gttcaacatc cttaatcatc agggaaatgc aaatcaaaac    4500
aaccctgaga ttccacctca caccagtgag aatggctaag atcaaaaatt caggtgacag    4560
cagatgctgg cgaggatgtg gagaaagagg aacactcctc cattgttggt gggattgcag    4620
gcttgtacaa ccactctgga aatcagtctg gcggttcctc agaaaattgg acatagtact    4680
accggaggat ccagcaatac ctctcctggg catatatcca gaagaagccc aactggtaa     4740 gaaggacaca tgctccacta tgttcatagc agccttattt ataatagcca gaaactggaa    4800
agaacccaga tgcccctcaa cagaggaatg gatacagaaa atgtggtaca tctacacaat    4860
ggagtactac tcagctatta aaagaatga atttatgaaa ttcctagcca aatggatgga    4920
cctggagagc atcatcctga gtgaggtaac acaatcacaa aggaactcac acaatatgta    4980
ctcactgata agtggatact ag                                             5002
```

<210> SEQ ID NO 433
<211> LENGTH: 5002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433

```
atggccaagg gcaagcgccg caacctgacc aaccgcaacc aggaccacag ccccagcccc      60
gagcccagca cccccaccag ccccagcccc ggcaacccca caccccccga gaacctggac    120
ctggacctga aggcctacct gatgatgatg gtggaggaca tcaagaagga cttcaacaag    180
agcctgaagg agatccagga gaacaccgcc aaggagctgc aggtgctgaa ggagaagcag    240
gagaacacca tcaagcaggt ggaggtgctg accgagaagg aggagaagac ctacaagcag    300
gtgatggaga tgaacaagac catcctggac ctgaagcgcg aggtcgacac catcaagaag    360
acccagagcg aggccaccct ggagatcgag accctgggca gaagagcgg caccatcgac    420 ctgagcatca gcaaccgcat ccaggagatg gaggagcgca tcagcggcgc cgaggacagc    480
atcgagaaca tcggcaccac catcaaggag aacggcaagt gcaagaagat cctgaccag    540 aacatccagg agatccagga caccatccgc cgccccaacg tgcgcatcat cggcgtggac    600
gagaacgagg acttccagct gaagggcccc gccaacatct tcaacaagat catcgaggag    660
```

```
aacttcccca acctgaagaa cgagatgcac atgaacatcc aggaggccta ccgcaccccc    720
aaccgcctgg accagaagcg caacagctct agacacatca tcatccgcac cagcaacgcc    780
ctgaacaagg accgcatcct gaaggccgtg cgcgagaagg ccaggtgac ctacaagggc     840 aagcccatcc gcatcacccc cgacttcagc cccgagacca tgaaggcccg ccgcgcctgg    900
accgacgtga tccagaccct gcgcgagcac aagctgcagc cccgcctgct gtaccccgcc    960
aagctgagca tcatcatcga gggcgagacc aaggtgttcc acgacaagac caagttcacc   1020
cactacctga gcaccaaccc cgccctgcag cgcatcatca ccgagaagaa ccagtacaag   1080
aacggcaaca cgccctgga gaagacccgc cgctaatccc tcaacaaacc ttaattaaga    1140
cagccacaag aacagaatgc ccccctgac caccaagatc accggcagca caactactt    1200 cagcctgatc agcctgaaca tcaacggcct gaacagcccc atcaagcggc accgcctgac   1260
caactggctg cacaagcagg accccacctt ctgttgcctc caggagaccc acctgcgcga   1320
gaaggaccgg cactacctgc ggatgaaggg ctggaagacc atctttcagg ccaacggcat   1380
gaagaagcag gctggcgtgg ccatcctgat cagcgacaag atcgacttcc agcccaaggt   1440
gatcaagaag gacaaggagg ccacttcat cctgatcaag gcaagatcc tgcaggagga    1500 gctgagcatt ctgaacatct acgcccccaa cacccgcgcc gccaccttca ccaaggagac   1560
cctcgtgaag ctgaaggccc acatcgctcc ccacaccatc atcgtcggcg acttcaacac   1620 cccctgagc cccatggaca gatcttggaa gcagaagctg aaccgcgaca ccctgaagct    1680
gaccgaggtg atgaagcaga tggacctgac cgacatctac cgcaccttct accccaagac   1740
caagggctac accttcttca gcgctcccca cggcaccttc agcaagatcg accacatcat   1800
cggccacaag agcgggctga accggctgaa gaacatcgag atcgtgccct gcatcctgag   1860
cgaccaccat gccctgcgcc tgatcttcaa caacaagatt aacaaccgca agcccacctt   1920
cacctggaag ctgaacaaca ccctgctgaa cgacaccctg gtgaaggaag gcatcaagaa   1980
ggagatcaag gacttcctgg agttcaacga gaacgaggcc accacctacc ctaacctgtg   2040
ggacaccatg aaggccttcc tgcggggcaa gctgatcgcc atgagcgcct tcaagaagaa   2100
gcgggagcgc gcccacacta gtagcctgac caccccacctg aaggccctgg agaagaagga   2160
ggctaactcc cccaagcgct cccggcggca ggagatcatc aagctgcgcg gcgagatcaa   2220
ccaggtggag accggcgca ccatccaacg gatcaaccag acccggtctt ggttcttcga    2280
gaagatcaac aagatcgaca agcccctggc tcgcctgacc aagggccacc gcgacaagat   2340
cctgatcaac aagatccgca cgagaaggg cgacatcacc accgaccccg aggagatcca    2400
gaacaccatc cgcagcttct acaagcgcct gtacagcacc aagctggaga acctggacga   2460
gatgaccaag ttcctggacc gctatcaggt gcccaagctg aaccaggacc aggtggacct   2520
gctgaacagc cccatctccc caaggaaat cgaggccgtg atcaacagcc tgcccgccaa    2580
gaagagcccc ggccccgacg gcttcagcgc tgagttctac cagaccttca ggaggacct    2640 gaccccgtg ctgcacaagc ttttccacaa gatcgaggtc gagggcatcc tccccaacag    2700
cttctacgag gccaccatca ccctgatccc caagcccag aaggacccca ccaagatcga    2760
gaacttccgc cccatcagcc tgatgaacat cgacgccaag atcctgaaca agatcctcgc   2820
caaccgcatc caggagcaca tcaaggccat catccaccct gaccaggtcg gcttcatccc   2880
cggcatgcag ggctggttca acatccgcaa gagcatcaac gtgatccact acatcaacaa   2940
gctgaaggac aagaaccaca tgatcatcag cctggacgcc gagaaggcct tcgacaagat   3000
```

```
ccagcacccc ttcatgatca aggtcctgga gcgcagcggc attcagggcc agtacctcaa    3060
catgatcaag gccatctaca gcaagcccgt cgccaacatc aaggtgaacg gggagaagct    3120
ggaggccatc cctctgaaga gcggcacgcg tcagggctgt cctctgtccc cctacctgtt    3180
caacatcgtg ctggaggtgc tggcccgcgc tatccggcag cagaaggaga tcaagggcat    3240
ccagatcggc aaggaggaag tgaagatcag cctgttcgcc gacgacatga tcgtgtacat    3300
cagcgacccc aagaacagca accgcgagct cctgaacctg atcaacagct cggcgaggt    3360
ggctggctac aagatcaaca gcaacaagag catggccttc ctgtacacca agaacaagca    3420
ggccgagaag gagatccgcg agaccacccc cttcagcatc gccaccaaca acatcaagta    3480
cctgggcgtg accctgacca aggaggtgaa ggacctgtac gacaagaact tcaagagcct    3540
gaagaaggag atcaaggagg acctgcgccg ctggaaggac ctgccctgca gctggatcgg    3600
ccgcaccaac atcgtgaaga tggccatcct gcccaaggct atctaccgct tcaacgccat    3660
ccccatcaag atccccaccc agttcttcaa cgagctcgag ggcgccatct gcaagttcat    3720
ctggaacaac aagaagcccc gcatcgccaa gaccctgctg aaggacaagc gcaccagtgg    3780
ggggatcacc atgcccgacc tgaagctgta ctaccgcgcc atcgtgatca agaccgcctg    3840
gtactggtac cgcgaccgcc aggtggacca gtggaaccgc atcgaggacc ccgagatgaa    3900
cccccacacc tacggccacc tgatcttcga caagggcgcc aagaccatcc agtggaagaa    3960
ggacagcatc ttcaacaact ggtgctggca caactggctg ctgagctgcc gccgcatgcg    4020
catcgacccc tacctaagcc cctgcaccaa ggtgaagagc aagtggatca aggagctgca    4080
catcaagccc gagactctga agctgatcga ggagaaggtg ggcaagagcc tggaggacat    4140
gggcaccggc gaaaagttcc tgaaccgcac cgccatggcc tgtgccgtgc gcagccggat    4200
cgataagtgg gacctgatga agctgcagtc cttctgtaag gccaaggata ccgtgtacaa    4260
gaccaagcgc cccccgaccg actgggagcg catcttcacc taccccaaga gcgaccgcgg    4320
cctgatcagc aacatctaca aggagctgaa gaaggtggac ctgcgcaaga gcaacaaccc    4380
gctgaagaag tggggctccg agctgaacaa ggagttctcc cccgaggagt accgcatggc    4440
cgagaagcac ctgaagaagt gcagcaccag cctgatcatc cgcgagatgc agatcaagac    4500
caccctgcgc ttccacctga ccccgtgcg gatggccaag atcaagaaca gcggcgactc    4560
gcgatgctgg cggggctgcg gcgagcgcgg caccctgctg cactgctggt gggactgtcg    4620
cctggtccag cccctgtgga gagcgtgtg gcggttcctg cggaagctgg acatcgtgct    4680
gcccgaggac cccgctatcc ccctgctggg catctaccct gaggaggccc ccaccggcaa    4740
gaaggacacc tgcagtacca tgttcatcgc cgctctgttc atcatcgccc gcaactggaa    4800
ggagccccgc tgccccagca ccgaggagtg gattcagaag atgtggtaca tctacaccat    4860
ggagtactac agcgccatca agaagaacga gttcatgaag ttcctggcca agtggatgga    4920
cctggagagc atcatcctga gcgaggtgac ccagagccag cgcaacagcc acaacatgta    4980
cagcctgatc agcggctact ag                                             5002
```

SYNTHETIC MAMMALIAN RETROTRANSPOSON GENE

This application claims the benefit of U.S. Provisional Application No. 60/473,658 filed on May 28, 2003, which is incorporated herein by reference in its entirety.

SEQUENCE LISTING

The instant application contains a Sequence Listing which has been submitted via EFS-Web and is hereby incorporated by reference in its entirety. Said ASCII copy, created on Oct. 12, 2009, is named 61241716.txt, and is 127,114 bytes in size.

BACKGROUND OF THE INVENTION

Transposons are discrete mobile DNA segments that are common constituents of plasmid, virus, and bacterial chromosomes. These elements are detected by their ability to transpose self-encoded phenotypic traits from one replicon to another, or to transpose to a known gene and inactivate it. There are two types of transposons, ranging in size from about 750 to greater than 50,000 nucleotide base pairs. One type, known as the small insertion sequence or IS element, does not encode any known phenotypic traits. The other type encompasses relatively large units that do encode phenotypic traits such as antibiotic resistance (Plasmids and Transposons Environmental Effects and Maintenance Mechanisms; Edited by C. Stuttard and K. Rozee; Academic Press, New York; Pages 165-205). Transposons or transposable elements include a piece of nucleic acid bounded by repeat sequences. Active transposons encode enzymes that facilitate the insertion of the nucleic acid into DNA sequences.

In vertebrates, the discovery of DNA transposons, mobile elements that move via a DNA intermediate, is relatively recent (Radice, A. D., et al., 1994. Mol. Gen. Genet. 244, 606-612). Since then, inactive, highly mutated members of the Tc1/mariner as well as the hAT (hobo/Ac/Tam) superfamilies of eukaryotic transposons have been isolated from different fish species, *Xenopus* and human genomes (Oosumi et al., 1995. Nature 378, 873; Ivics et al. 1995. Mol. Gen. Genet. 247, 312-322; Koga et al., 1996. Nature 383, 30; Lam et al., 1996. J. Mol. Biol. 257, 359-366 and Lam, W. L., et al. Proc. Natl. Acad Sci. USA 93, 10870-10875).

Retrotransposons are naturally occurring DNA elements which are found in cells from almost all species of animals, plants and bacteria which have been examined to date. They are capable of being expressed in cells, can be reverse transcribed into an extrachromosomal element and reintegrate into another site in the same genome from which they originated.

Retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposon are structurally different and also retrotranspose using radically different mechanisms.

Unlike the LTR retrotransposons, non-LTR elements (also called polyA elements) lack LTRs and instead end with polyA or A-rich sequences. The LTR retrotransposition mechanism is relatively well-understood; in contrast, the mechanism of retrotransposition by non-LTR retrotransposons has just begun to be elucidated (Luan and Eickbush, 1995, Mol. Cell. Biol. 15:3882-3891; Luan et al., 1993, Cell 72:595-605). non-LTR retrotransposons can be subdivided into sequence-specific and non-sequence-specific types. L1 is of the latter type being found to be inserted in a scattered manner in all human, mouse and other mammalian chromosomes.

The L1 element (also known as a LINE) has been extremely successful at colonizing the human genome. Early approximations estimated that L1s are present at 100,000 copies in the human genome and comprise 5% of nuclear DNA (Fanning and Singer, 1987, Biochim Biophys Acta 910: 203-121). However, recent studies suggest that as many as 850,000 L1s may exist in the human genome (Smit et al., 1996, Current Opinion in Genetics and Development). Most of these copies are truncated at the 5' end and are presumed to be defective. Similar to full-length elements, the 5' truncated copies are often flanked by short target site duplications (TSDs).

A 6.1 kb full-length L1 consensus sequence reveals the following conserved organization: a 5' untranslated leader region (UTR) with an internal promoter; two non-overlapping reading frames (ORF1 and ORF2); a 200 bp 3' UTR and a 3' poly A tail. ORF1 encodes a 40 kd protein and may serve a packaging function for the RNA (Martin, 1991, Mol. Cell Biol. 11:4804-4807; Hohjoh et al., 1996, EMBO J. 15:630-639), while ORF2 encodes a reverse transcriptase (Mathias et al., 1991, Science 254:1808-1810). ORF1 and possibly ORF2 proteins associate with L1 RNA, forming a ribonucleoprotein particle. Reverse transcription by ORF2 protein may occur, resulting in L1 cDNAs, which are integrated into the genome (Martin, 1991, Curr. Opin. Genet. Dev. 1:505-508). Additionally, L1 elements are usually flanked by TSD's ranging from 7 to 20 bp. The full L1 and other non-LTR retrotransposons lack recognizable homologs of retroviral integrase, protease and RNase H. This group of elements employs a fundamentally different mechanism for transposition than the LTR-retrotransposons.

Some human L1 elements can retrotranspose (express, cleave their target site, and reverse transcribe their own RNA using the cleaved target site as a primer) into new sites in the human genome, leading to genetic disorders. For example, germ line L1 insertions into the factor VIII and dystrophin gene give rise to hemophilia A and muscular dystrophy, respectively (Kazazian et al., 1988, Nature 332:164-166; Narita et al., 1993, J. Clinical Invest. 91:1862-1867; Holmes et al., 1994, Nature Genetics 7:143-148), while somatic cell L1 insertions into the c-myc and APC tumor suppressor gene are implicated in rare cases of breast and colon cancer, respectively (Morse et al., Nature 333:87-90; Miki et al., 1992, Cancer Research 52:643-645). L1 retrotransposons account, directly or indirectly, for more than 30% of mammalian genomes by mass (Lander et al., 2001, Nature 409:860-921), by means of self-mobilization and trans-mobilization of Alu elements (Dewannieux et al., 2003, Nature Genet. 35:41-48). A full-length (about 6-kilobase) L1 consists of two open reading frames, ORF1 and ORF2, encode proteins for retrotransposition (Feng et al., 1996, Cell 87:905-916; Moran et al., 1996, Cell 87:917-927).

Thus, a highly active L1 element would be potentially useful as a tool for mammalian genetics.

BRIEF SUMMARY OF THE INVENTION

In one embodiment, the invention relates to a synthetic transposon gene. In another embodiment, the invention relates to a synthetic mammalian transposon gene.

We have now found that synthetic transposon and retrotransposon genes may be useful for gene therapy applications and for other genetic applications described herein.

In a further embodiment, the invention relates to a synthetic retrotransposon gene. An additional embodiment of the invention provides a synthetic mammalian retrotransposon gene.

In one embodiment, the invention relates to a synthetic ORF2 gene. In another embodiment, the invention relates to a synthetic mammalian ORF2 gene. The synthetic gene exhibits a higher level of expression relative to natural L1 retrotransposon ORF2 gene.

In one embodiment, the invention relates to a synthetic ORF1 gene. In another embodiment, the invention relates to a synthetic mammalian ORF1 gene. The synthetic gene exhibits a higher level of expression relative to natural L1 retrotransposon ORF1 gene.

In further embodiments, the invention relates to a synthetic ORF2 or ORF1 gene comprising human-associated codons. In additional embodiments of the invention, the synthetic ORF2 or ORF1 gene comprise only human-associated codons. In these embodiments, human-associated codons refer to those codons most frequently used in highly expressed mammalian genes. Of note, there are often two or more such codons encoding each amino acid, thus, many possible synthetic elements are possible.

In another embodiment, the invention provides a synthetic mammalian ORF2 gene comprising SEQ ID NO:1.

In another embodiment, the invention provides a synthetic mammalian ORF1 gene comprising SEQ ID NO:2.

In another embodiment, the invention provides a synthetic mammalian ORF2 gene comprising SEQ ID NO:3.

In another embodiment, the invention provides a synthetic mammalian ORF1 gene comprising SEQ ID NO:4.

In one embodiment, the invention relates to a transposon comprising a synthetic transposon gene. In another embodiment, the invention relates to a retrotransposon comprising a synthetic retrotransposon gene. In additional embodiments, the invention relates to an L1 retrotransposon comprising a synthetic ORF2 or ORF1 gene. In another embodiment, the invention relates to an L1 retrotransposon comprising a synthetic ORF2 and a synthetic ORF1 gene. Additional embodiments of the invention provide a mammalian L1 retrotransposon comprising a synthetic mammalian ORF2 gene, a synthetic mammalian ORF1 gene, or both a synthetic mammalian ORF2 and a synthetic mammalian ORF1 gene. The retrotransposon retrotransposes at least as efficiently as a native L1 retrotransposon. In a further embodiment of the invention, the retrotransposon retrotransposes more efficiently than a native L1 retrotransposon.

In another embodiment, the invention provides recombinant vector constructs comprising a synthetic ORF2 gene. In another embodiment, the invention provides recombinant vector constructs comprising a synthetic ORF1 gene. In another embodiment, the invention provides recombinant vector constructs comprising a synthetic ORF2 gene and a synthetic ORF1 gene. Eukaryotic cells transfected, transformed, or infected with such constructs are likewise provided.

In additional embodiments, the invention provides methods for preparing a synthetic ORF2 or ORF1 gene.

In another embodiment, the invention relates to a method of delivering a desired gene, or a biologically active fragment thereof, to the cells of a mammal. The method comprises the administration of a synthetic ORF2 or ORF1 gene, or a combination thereof and the desired gene to said mammal.

A further embodiment of the invention provides compositions comprising a cassette comprising a synthetic ORF2 or ORF1 gene, or a combination thereof, and a desired gene and a pharmaceutically acceptable carrier. In another embodiment, the invention relates to a method of treating a genetic disorder in a mammal. The method comprises administering a composition comprising a synthetic ORF2 or ORF1 gene or a combination thereof and a desired gene and a pharmaceutically acceptable carrier to a mammal having the genetic disorder in question.

In another embodiment, the invention relates to a method of identifying an uncharacterized gene, or a biologically active fragment thereof, in cells. The method comprises the administration of a synthetic ORF2 or ORF1 gene, or a combination thereof, and a detectable tag sequence, the identification of those cells expressing the tag sequence, and the isolation and characterization of DNA flanking the tag sequence.

Other embodiments of the invention are disclosed infra.

BRIEF DESCRIPTION OF THE DRAWINGS

FIG. 1a schematically depicts the L1 structure. TSD refers to target site duplication; UTR refers to untranslated region.

FIG. 1b provides a schematic overview of the synthesis of the mammalian ORF2 gene. Oligonucleotides encoding each fragment are mixed in a PCR assembly reaction and subsequently used as template for amplification. Amplification products are cloned and ligated together with unique restriction sites (labelled A to J).

FIG. 1c shows a plasmid structure. The test sequences (lacZ, mORF2 or smORF2) are fused, in frame, downstream of the GFP ORF. An independent neo transcript is used to monitor transfection efficiency and loading. The short lines extending along parts of the plasmid represent probes used in FIG. 1d.

FIG. 1d provides an analysis of smORF2 expression. Top: RNA expression of GFPlacZ, GFPmORF2 and GFPsmORF2. Middle: RNA expression of loading control. Bottom: protein expression of GFPlacZ, GFPmORF2 and GFPsmORF2.

FIG. 5b shows results in tissue culture cells.

FIG. 6 lists SEQ ID NO:1 (synthetic murine ORF2).

FIG. 7 lists SEQ ID NO:2 (synthetic murine ORF1).

FIG. 8 lists SEQ ID NO:3 (synthetic human ORF2).

FIG. 9 lists SEQ ID NO:4 (synthetic human ORF1).

FIG. 10 lists the sequence of oligonucleotides used (SEQ ID NO:5-209) for the murine experiments.

FIG. 11 lists the sequence of oligonucleotides used (SEQ ID NO:210-411) for the human experiments.

DETAILED DESCRIPTION OF THE INVENTION

Figure 2A:
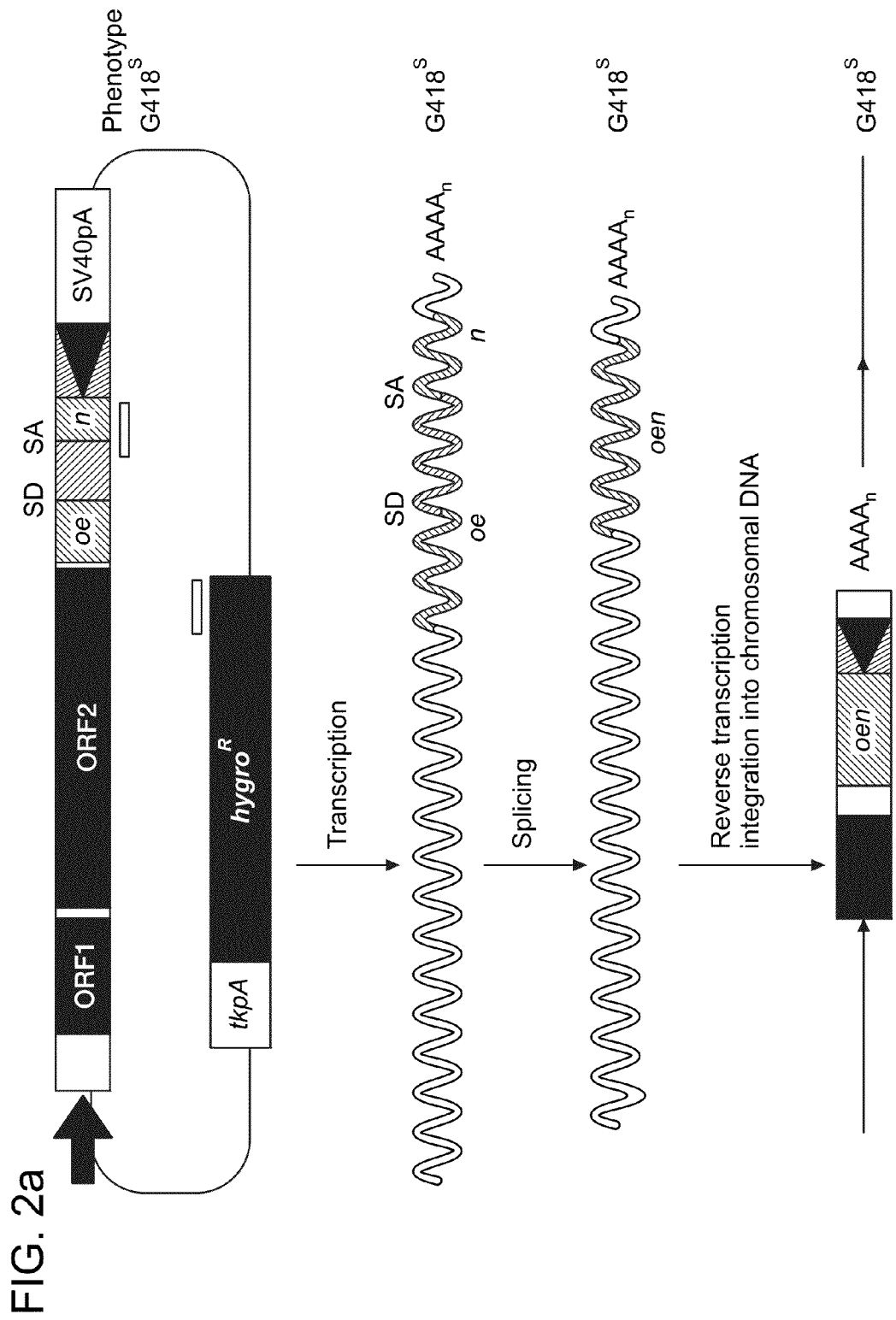
FIG. 2a provides a schematic representation of a retrotransposition assay. The L1 element contains an intron-interrupted neo reporter in the 3' untranslated region with its own promoter and polyadenylation signal. Wen neo is transcribed from the L1 promoter, spliced, reverse-transcribed and integrated into the genome does a cell become G418-resistant. The short lines extending along parts of the plasmid represent probes for RNA analysis. SD refers to the splice donor; SA refers to the splice acceptor.

Disclosed herein is a synthetic transposon gene. Further disclosed herein is a synthetic mammalian transposon gene. Additionally disclosed herein is a synthetic retrotransposon gene. Further disclosed herein is a synthetic mammalian retrotransposon gene.

A synthetic retrotransposon may retrotranspose at least as efficiently as a native retrotransposons in one embodiment. In another embodiment, the synthetic retrotransposon retrotransposes more efficiently than a native retrotransposon. In yet another embodiment, the synthetic retrotransposon of the invention retrotransposes about 2-fold more efficiently than a native retrotransposon. In yet another embodiment, the retrotransposon of the invention retrotransposes about 25-fold more efficiently than a native retrotransposon. In yet another embodiment, the retrotransposon of the invention retrotransposes about 100 to 200 fold more efficiently than a native retrotransposon.

A synthetic transposon may transpose at least as efficiently as a native transposons in one embodiment. In another embodiment, the synthetic transposon transposes more efficiently than a native retrotransposon. In yet another embodiment, the synthetic transposon of the invention transposes about 2-fold more efficiently than a native transposon. In yet another embodiment, the transposon of the invention transposes about 25-fold more efficiently than a native transposon. In yet another embodiment, the transposon of the invention transposes about 100 to 200 fold more efficiently than a native transposon.

Disclosed herein is a synthetic ORF2 gene. In one embodiment, the synthetic ORF2 gene of the invention is vertebrate, including fish, reptiles, amphibians, birds, insects, or the like. In one embodiment, the synthetic ORF2 gene of the invention is mammalian, including murine, bovine, equine or the like. One embodiment of the synthetic gene not only uses codons optimal for humans, but also destroys a nucleotide sequence bias that may be responsible for its poor expression.

In one embodiment, the synthetic ORF2 gene exhibits a higher level of expression relative to natural L1 retrotransposon ORF2 gene.

In another embodiment of the invention, the synthetic ORF2 gene encodes the same protein as does the native gene, yet comprises human-associated codons. In another embodiment of the invention, the synthetic ORF2 gene comprises only human-associated codons. "Human-associated codons" refer to those codons most frequently used in highly expressed mammalian genes. One of skill in the art would be able to determine which codons were most frequently associated with a particular gene. Of note, there are often two or more such codons encoding each amino acid, thus, many possible synthetic elements are possible. For example, human-associated codons for each amino acid may include: alanine GCC, arginine CGC or CGG, asparagine AAC, aspartate GAC, cysteine TGC, glutamine CAG, glutamate GAG, glycine GGC or GGG, histidine CAC, isoleucine ATC, leucine CTG or CTC, lysine AAG, methionine ATG, proline CCC, phenylalanine TTC, serine AGC or TCC, threonine ACC, tryptophan TGG, tyrosine TAC, and valine GTG or GTC.

In one embodiment, the synthetic ORF2 gene has a DNA sequence that has less than 100% identity with that of the natural L1 retrotransposon ORF2 gene. In another embodiment, the synthetic ORF2 gene has a DNA sequence that has no more than about 90% identity with that of the natural L1 retrotransposon ORF2 gene. In another embodiment, the synthetic ORF2 gene has a DNA sequence that has no more than about 80% identity with that of the natural L1 retrotransposon ORF2 gene.

In another embodiment, the synthetic mammalian ORF2 gene has a DNA sequence that has at least about 70% identity with SEQ ID NO:1. In yet another embodiment, the synthetic mammalian ORF2 gene of the invention comprises SEQ ID NO:1.

Further disclosed herein is a synthetic ORF1 gene. In another embodiment of the invention, the synthetic ORF1 gene of the invention is vertebrate, including fish, reptiles, amphibians, birds, insects, or the like. In another embodiment of the invention, the synthetic ORF1 gene of the invention is mammalian, including murine, bovine, equine or the like. In a further embodiment of the invention, the synthetic ORF1 gene exhibits a higher level of expression relative to natural L1 retrotransposon ORF1 gene.

In another embodiment of the invention, the synthetic ORF1 gene encodes the same protein as does the native gene, yet comprises human-associated codons. In another embodiment of the invention, the synthetic ORF1 gene comprises only human-associated codons.

In one embodiment, the synthetic ORF1 gene of the invention has a DNA sequence that has less than 100% identity with that of the natural L1 retrotransposon ORF1 gene. In another embodiment, the synthetic ORF1 gene of the invention has a DNA sequence that has no more than about 90% identity with that of the natural L1 retrotransposon ORF1 gene. In another embodiment, the synthetic ORF1 gene of the invention has a DNA sequence that has no more than about 80% identity with that of the natural L1 retrotransposon ORF1 gene.

In another embodiment, the synthetic mammalian ORF1 gene of the invention has a DNA sequence that has at least about 70% identity with SEQ ID NO:2. In yet another embodiment, the synthetic mammalian ORF1 gene of the invention comprises SEQ ID NO:2.

In another embodiment, the synthetic mammalian ORF2 gene of the invention has a DNA sequence that has at least about 70% identity with SEQ ID NO:3. In yet another embodiment, the synthetic mammalian ORF2 gene of the invention comprises SEQ ID NO:3.

In another embodiment, the synthetic mammalian ORF1 gene of the invention has a DNA sequence that has at least about 70% identity with SEQ ID NO:4. In yet another embodiment, the synthetic mammalian ORF1 gene of the invention comprises SEQ ID NO:4.

In one embodiment, the synthetic mammalian ORF2 gene of the invention is human. In another embodiment of the invention, the synthetic mammalian ORF1 gene of the invention is human.

A transposon comprising a synthetic transposon gene of the invention is provided in one embodiment. A retrotransposon comprising a synthetic retrotransposon gene of the invention is provided in another embodiment.

An L1 retrotransposon comprising a synthetic ORF2 gene of the invention is provided in an additional embodiment. A further embodiment provides an L1 retrotransposon comprising a synthetic ORF1 gene of the invention. Yet another embodiment provides an L1 retrotransposon comprising both a synthetic ORF2 gene of the invention and a synthetic ORF1 gene of the invention. The transposon or retrotransposon transposes or retrotransposes, respectively, at least as efficiently as a native transposon or retrotransposon in one embodiment. In another embodiment, the transposon or retrotransposon transposes or retrotransposes, respectively, more efficiently than a native transposon or retrotransposon.

A mammalian L1 retrotransposon comprising a synthetic mammalian ORF2 gene of the invention is provided in an additional embodiment. A further embodiment provides a mammalian L1 retrotransposon comprising a synthetic mammalian ORF1 gene of the invention. Yet another embodiment provides a mammalian L1 retrotransposon comprising both a synthetic mammalian ORF2 gene of the invention and a synthetic mammalian ORF1 gene of the invention. The mammalian retrotransposon retrotransposes at least as efficiently as a native L1 retrotransposon in one embodiment. In another embodiment, the mammalian retrotransposon retrotransposes more efficiently than a native L1 retrotransposon. In yet another embodiment, the retrotansposon of the invention retrotransposes about 2-fold more efficiently than a native L1 retrotransposon. In yet another embodiment, the retrotransposon of the invention retrotransposes about 25-fold more efficiently than a native L1 retrotransposon. In yet another embodiment, the retrotransposon of the invention retrotransposes about 100 to 200 fold more efficiently than a native L1 retrotransposon.

Recombinant vector constructs comprising a synthetic ORF2 gene of the invention are provided in an additional embodiment. Recombinant vector constructs comprising a synthetic ORF1 gene of the invention are provided in an additional embodiment. Recombinant vector constructs comprising both a synthetic ORF2 gene of the invention and a synthetic ORF1 gene of the invention are provided in an additional embodiment. The recombinant vector may be selected, without limitation, from chemical conjugates, viral (DNA or RNA) vectors, such as Epstein Barr virus (EBV), polyoma-based virus, adeno-associated virus, lentivirus, parvovirus, herpes simplex virus, retroviruses, poxviruses, and the like, fusion proteins, plasmids, and phage. It is not necessary that the vector sequences be limited to naturally occurring eukaryotic viral elements. Artificial chromosomes are also contemplated in the invention, including mammalian artificial chromosomes.

In one embodiment, the subject plasmid is pCEP4, with the native mORF2 sequence replaced with the DNA sequence of the synthetic mammalian ORF2 or ORF1 gene of the invention.

A recombinant vector construct according to the invention may exhibit a retrotransposition frequency that is more active than that observed for the native vector. In one embodiment, the construct of the invention exhibits a retrotransposition frequency that may be between about 2 to about 100 times more active than that observed for the native vector.

Eukaryotic cells transfected, transformed, or infected with recombinant vector constructs according to the invention are provided in another embodiment.

A method of preparing a synthetic ORF2 or ORF1 gene of the invention is provided. In one embodiment, the method comprises preparing a synthetic ORF2 or ORF1 gene of the invention that comprises "human-associated codons". In another embodiment, the method comprises preparing a synthetic ORF2 or ORF1 gene of the invention that comprises only "human-associated codons". In another embodiment, the method further comprises the step of incorporating unique restriction enzyme sites at intervals of between about 400 to about 600 base pairs. In yet another embodiment, the method further comprises the step of resynthesizing the 3' untranslated region of the nucleotide sequence with more than one unique restriction enzyme sites, or using the 3' UTR of a cellular gene. In yet another embodiment, the method further comprises the step of designing oligonucleotides of between about 30 base pairs to about 90 base pairs in length to cover both the sense and complementary strands of the sequence. In yet another embodiment, the method further comprises the step of employing the oligonucleotides to synthesize between about 6 to about 12 fragments of DNA, which are between about 400 to about 600 base pairs in length each. In yet another embodiment, the method further comprises the step of performing PCR employing approximately equimolar mixtures of the sense and antisense oligonucleotides corresponding to each of said fragments. In yet another embodiment, the method further comprises the step of subcloning the PCR-resultant fragments together using the unique restriction enzyme sites to generate the complete gene.

A synthetic ORF2 or ORF1 gene may be prepared comprising "human-associated codons." The resulting nucleotide sequence may further be altered to incorporate unique restriction enzyme sites at approximately 500 base pair intervals. In addition, the 3' untranslated region may be resynthesized with multiple unique restriction enzyme sites to facilitate subcloning. Oligonucleotides may be designed to completely cover both strands of this new sequence, for example oligonucleotides of between about 30 to about 90 bpase pairs may be designed. Hairpins in these oligonucleotides (as predicted, for example, by the computer program Oligo 5.0) with a melting temperature greater than approximately 65° C. may be destroyed with mutations that conserved the amino acid sequence. These mutations may change the optimal codon to a less optimal alternative.

The resulting optimized ORF2 or ORF1 nucleotide sequence may then be subjected to a modified Polymerase Chain Reaction (Stemmer et al., 1995, Gene 164:49-53). For example, oligonucleotides from between about 40 base pairs to about 80 base pairs, which cover the entire sense strand may be synthesized. The complementary strand may also be synthesized with oligonucleotides from between about 40 base pairs to about 80 base pairs, with approximately a 30 base pair stagger with respect to the sense strand oligonucleotides. Oligonucleotides may have between about 20 to about 50 base pairs of hybridization with two oligonucleotides from the complementary strand. Using these oligonucleotides, the ORF2 or ORF1 nucleotide sequence may be synthesized in between about 6 to about 12 fragments of between about 400 to about 600 base pairs each. The sense and antisense oligonucleotides corresponding to each fragment may be mixed in approximately equimolar amounts, and a PCR reaction may be performed. For example, a 25-cycle assembly PCR may be performed. Other PCR cycles may also be employed and those of skill in the art having the benefit of this disclosure would be able to determine the optimal number of cycles for a particular purpose. This assembly reaction may be diluted into the PCR reactions containing, for example, the outermost oligonucleotides for the fragment as amplification primers.

The resulting fragments may be cloned, for example separately, into a plasmid, and approximately 20-30 clones may be sequenced for each. By standard subcloning procedures, mutations introduced during the oligosynthesis, assembly, or PCR may be removed. The resulting fragments may be subcloned together using the unique restriction enzymes sites previously engineered into the sequence, generating a complete optimized ORF2 or ORF1 nucleotide sequence in a plasmid.

A method of delivering a desired gene, or a biologically active fragment thereof, to the cells of a mammal, is likewise provided in an embodiment of the invention. In one embodiment of the invention, the desired gene is a therapeutic gene. The method comprises the administration of a synthetic ORF2 and/or ORF1 gene according to the invention and the desired gene to a mammal. Gene therapy methods are also contemplated according to embodiments of the invention. Genes that may be delivered via gene therapy by retrotransposition include, without limitation, Factor VIII, Factor IX, tyrosine hydroxylase, aromatic amino acid decarboxylase, apoptotic protease activating factor-1-dominant negative inhibitor (Apaf-1-DN), alpha-galactosidase A (AGA). Disorders and/or diseases that could be targeted via gene therapy by retrotransposition include, without limitation, hemophilia, Parkinson's disease, Fabry's disease, familial hypercholesterolemia, Gaucher's disease, Cystic Fibrosis, and adrenoleukodystrophy, adenosine deaminase deficiency (SCID), alpha-antitrypsin deficiency, Duchenne muscular dystrophy, pheylketouria, sickle cell anemia, Tay-Sachs disease, and the thalessemias.

Another embodiment provides a composition comprising a cassette comprising a synthetic ORF2 and/or ORF1 gene of the invention and a desired gene and a pharmaceutically acceptable carrier. In one embodiment, the cassette may comprise a heterologous or homologous DNA (non-L1 DNA) which may be inserted into the cell genome. This DNA may be positioned within the 3' UTR sequences, or between the 3' UTR and the polyA signal, and oriented such that expression of the DNA is under the control of a promoter. The type of DNA that may be inserted includes, without limitation, DNA which functions as a marker for identification of the site of insertion, for example, the neomycin (neo) resistance gene or other drug resistance genes (e.g., zeo, hygro, gpt), the green fluorescence protein (GFP) gene, lacZ, the herpes simplex virus (HSV) thymidine kinase gene, and even cell surface receptor genes such as, but not limited to, T cell receptor genes.

The route of administration of a composition according to the invention may also vary depending upon the disorder to be treated. The compositions may be administered to a subject in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema). In one embodiment, for treatment of patients having lung infection, the route of administration may be for example intranasal delivery by aerosol or via the blood. The appropriate pharmaceutically acceptable carrier will be evident to those skilled in the art and will depend in large part upon the route of administration.

In one embodiment of the invention, the promoter may be selected, without limitation, from RNA polymerase II promoters such as housekeeping promoters—actin, PGK, DNA polII or a ubiquitin promoter; tissue-specific promoters—the albumin, globin, ovalbumin promoter sequences, skin-specific promoters—K12 or K14, inducible promoters—steroid-inducible promoters, tetracycline-inducible promoters, and the like, and viral promoters—the SV40 early promoter, the Rous sarcoma virus (RSV) promoter and the cytomegalovirus immediate early promoter (CMV), as well as other retroviral LTRs and RNA polymerase III promoters such as an L1 element promoter, tRNA promoters and the 5S RNA promoter. The type of promoter which provides optimal expression of the desired DNA will depend on the desired result and will be apparent to the person of ordinary skill in the art.

To effect retrotransposition in a cell and, therefore, insertion of a desired DNA into the genome of a cell, a cassette comprising a synthetic ORF2 and/or ORF1 gene of the invention and a desired gene may be added to a population of cells in a composition suitable to effect uptake by the cells of the DNA. For example, for transfection of cells in vitro when the recombinant vector is in plasmid form, the cassette may be added to the cells in any number of formulations, including, but not limited to, a calcium phosphate transfection mixture, a liposome transfection formulation, and the like. Such types of transfection procedures are well known in the art and are described, for example, in Sambrook et al. (1989, Molecular Cloning: A Laboratory Manual, Cold Spring Harbor, N.Y.). The cassette may also be added to cells in the form of a virus which has been manipulated using recombinant DNA technology to accommodate the cassette, which is suitable for delivery of the cassette to the desired cells.

To direct insertion of DNA into inactive regions of host cell DNA, it may be possible to alter the ORF2 and/or ORF1 protein such that it cleaves host cell DNA at innocuous sequences, for example, in ribosomal RNA gene sequences. Alternatively, it may be possible to replace the endonuclease domain of ORF2 or ORF1 with the domain of another enzyme that specifically cleaves DNA at innocuous sequences. Such enzymes include, but are not limited to, the rep gene of adeno-associated virus and certain group I intron-encoded, site-specific endonucleases, e.g., the universal code equivalent of the yeast mitochondrial SCE1 gene.

In another embodiment, the DNA comprised in the cassette may be useful for the correction of a genetic defect in the cell into which the insertion is made. DNAs which can be used to effect correction of such genetic defects may be derived from, or comprise wild-type forms of genes which are mutated in the cell, thereby giving rise to the genetic defect. Such DNAs include, without limitation, any known or unknown DNA which can be used to correct a genetic defect in cells having such a defect. Examples of such DNA include cDNAs encoding the cystic fibrosis transmembrane conductance regulator (CFTR), cDNA encoding beta-globin, cDNA encoding blood clotting proteins, cDNA encoding enzymes such as, but not limited to adenosine deaminase, hypoxanthine guanine phosphoribosyl transferase (HGPRT) and the like, cDNAs which play a role in cancer, such as, but not limited to, tumor suppressor genes, p53, p21, p16, retinoblastoma, Wilm's tumor, and the like, and also cytokines, interleukins and genes which encode therapeutic peptides, and the like.

Accordingly, in one embodiment, the invention provides a method of treating a genetic disorder in a mammal, wherein the method comprises administering a composition comprising a cassette comprising a synthetic ORF2 and/or ORF1 gene of the invention and a desired gene and a pharmaceutically acceptable carrier to the mammal having said genetic disorder.

In another embodiment, the invention relates to the correction of genetic defects in animals. Mammals and, even more preferably, humans, are contemplated in further related embodiments. To correct a genetic defect in an animal, the above-mentioned method of gene delivery is included in the invention that may be based upon delivery of a desired gene, or a biologically active fragment thereof, by retrotransposition, to the cells of an animal having the genetic defect. To effect retrotransposition in a cell in vivo in an animal for treatment of the animal, the cassette comprising a synthetic ORF2 and/or ORF1 gene of the invention, wherein the desired gene is administered to the animal using technology known in the art and described, for example, in WO 94 28938 and U.S. Pat. No. 5,240,846, each of which is hereby incorporated herein by reference. Upon administration to the animal in the compositions described herein, the cassette, which may be taken up by the target cells subsequently undergoes retrotransposition.

Genetic defects which may be corrected accordingly using retrotransposition include, without limitation, cystic fibrosis, mutations in the dystrophin gene, genetic defects associated with blood clotting, and any other either known or as yet unknown genetic defect (e.g., lysosomal storage diseases and other metabolic diseases).

In an additional embodiment, a method of identifying an uncharacterized gene, or a biologically active fragment thereof, in cells is provided, comprising the administration of a synthetic ORF2 and/or ORF1 gene according to the invention and a detectable tag sequence, the identification of those cells expressing the tag sequence, and the isolation and characterization of DNA flanking the tag sequence. In another embodiment, the method may include cloning genes that may be heretofore unknown or unclonable. The "tag" DNA may be selected, without limitation, from $neo^R$, the GFP gene, lacZ, and the like.

Following retrotransposition of the tag DNA into cells, cells having the tag sequence inserted in the genome may be identified using any number of techniques that are well known in the art. For example, hybridization may be used wherein a probe comprising the tag DNA is used to identify cells having the tag DNA or RNA. Where the tag DNA is expressed as a protein, any number of immunological techniques may be used to identify cells expressing the tag protein. Such technology is well known in the art and is described, for example, in Sambrook et al. (supra). The DNA flanking tag DNA may then be isolated and cloned using ordinary technology described in, for example, Sambrook (supra), thereby effecting isolation and characterization of genes and regions of DNA which may be heretofore unknown.

"Retrotransposition" as used herein, includes the process of integration of a sequence into a genome, expression of that sequence in the genome, reverse transcription of the integrated sequence to generate an extrachromosomal copy of the sequence and reintegration of the sequence into the genome.

"Gene" as used herein, includes an actual gene including both the exons and introns of the gene.

"Heterologous DNA" as used herein, includes DNA which may not naturally be found in the cell into which it is inserted. For example, when mouse or bacterial DNA is inserted into the genome of a human cell, such DNA is referred to herein as "heterologous DNA." In contrast, the term "homologous DNA" as used herein, denotes DNA that is found naturally in the cell into which it is inserted. For example, the insertion of mouse DNA into the genome of a mouse cell constitutes insertion of "homologous DNA" into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

"Non-L1 DNA" as used herein, includes DNA which does not naturally occur in an L1 element.

It will be appreciated that embodiments of the invention should not be construed to be limited in any way to the precise DNA sequences which are disclosed herein. Homologous DNA sequences having substantially the same function as the disclosed DNA sequences are also considered to be included in the invention. Furthermore, it is recognized that gene sequences among closely related structures (such as retrotransposon ORFs, which have essentially the same function) may vary considerably, and that such sequences are likewise considered to be included in the invention.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 7 out of 10, are matched or homologous, the two sequences share 70% identity. By way of example, the polypeptide sequences ACDEFG and ACDHIK share 50% identity and the nucleotide sequences CAATCG and CAAGAC share 50% identity.

"Complementary," as used herein, refers to the subunit sequence complementarity between two nucleic acids, e.g., two DNA molecules. For example, when a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

As discussed herein, certain embodiments of the invention provide DNA encoding a protein product which may be used in gene therapy to correct a genetic defect in a cell. It should be understood that such a protein may comprise native polypeptide sequences, or may comprise modifications which render the protein in general more suitable as a gene therapy agent and more stable in a cell.

An additional embodiment of the invention provides for analogs of proteins or peptides encoded by a DNA sequence to be inserted into the genome of a cell. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups, but are not limited to these groups: glycine, alanine; valine, isoleucine, leucine; aspartic acid, glutamic acid; asparagine, glutamine; serine, threonine; lysine, arginine; and phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine. In the latter instance, this is most applicable if reconstituted nucleic acid/protein particles are used for delivery. It is essentially and in vitro modification followed by an in vivo delivery.

Also included are polypeptides which have been modified using ordinary molecular biological techniques to improve their resistance to proteolytic degradation or to optimize solubility properties or to render them more suitable as therapeutic agents. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The term "correction of a genetic defect" as used herein, includes the expression of a wild type gene product in a cell in an amount to restore normal function to the cell, which function was considered to be abnormal due to the genetic defect. The term also applies to situations wherein the genetic defect in the animal is corrected by delivering a wild type copy of the defective gene to a cell type other than the actual cell expressing the defective protein. Expression of the wild type copy of the gene in the other cells, and secretion of the wild type protein expressed therein may also serve to correct a genetic defect in the animal.

EXAMPLES

It should be appreciated that the invention should not be construed to be limited to the examples which are now described; rather, the invention should be construed to include any and all applications provided herein and all equivalent variations within the skill of the ordinary artisan.

Example 1 smORF2 and ORF1 sequences were created by replacing each codon in the mouse L1 ORFs with the favored codons in highly expressed human genes (Haas et al., 1996, Curr. Biol. 6:315-324). The sequence was further altered with silent mutations introducing unique cleavage sites and eliminating potential hairpins that might have inhibited gene assembly. 60-mer oligonucleotides collectively encoding both strands of smORF2 were ordered from Qiagen, and gene synthesis (Stemmer et al., 1995, Gene 164:49-53) was performed on each '500-bp segment, as shown in FIG. 1b.

Assembly reactions contained each primer at 30 nM and 1× ExTaq mix (Takara) in a total of 25 µl. Amplification reactions contained each outer primer at 0.5 µM, 2.5 µl assembly reaction, and 1× ExTaq mix in a total volume of 25 µl. PCR conditions were 94° C. for 4 min, 25 cycles of 94 'C. for 30 s, 65 'C. for 30 s, and 72 'C. for 30 s, followed by 72 'C. for 7 min. PCR products were cloned into pCRII with the TOPO-TA cloning kit (Invitrogen). A total of 24-48 clones were sequenced for each fragment, and mutations were removed by standard cloning techniques. Finally, synthesized fragments were ligated together in pBluescriptKS⁻. Oligonucleotide sequences used are shown in FIG. 10.

Fusion vectors were prepared (as shown in FIG. 1c), wherein the test sequences (lacZ, mORF2 or smORF2) are fused, in frame, downstream of the GFP ORF. An independent neo transcript is also inserted.

The expression of smORF2 was subsequently analyzed via immunoblot analysis. Cells were harvested in 5% SDS/PBS; this was followed by sonication. Total lysates were subjected to 7.5% SDS-polyacrylamide-gel electrophoresis and transferred to poly(vinylidene difluoride) (Amersham). Antibody incubations were performed in PBS containing 0.05% Tween-20 and 5% milk. Washes were performed in PBS, 0.1% Tween-20. Anti-GFP(FL) antibody (Santa Cruz) was used at 1:250 dilution. Anti-rabbit IgG (Amersham) was used at 1:5,000 dilution. Blots were developed with ECL-plus (Amersham).

In both human and mouse cells, transfection of GFPsmORF2 led to a massive increase in RNA compared with wild-type GFPmORF2 (FIG. 1d, top panel, lanes 3 and 4). The introduction of two mutations that abolish the endonuclease and reverse transcriptase activities of mORF2 provided a further slight increase in smORF2 RNA levels (FIG. 1d, top panel, lanes 5). Probing for the vector-encoded neo transcript showed that these increases in RNA were not due to differences in transfection efficiency or loading (FIG. 1d, middle panel). Immunoblotting these samples with anti-GFP (FIG. 1d, bottom panel) showed that protein levels were correlated with RNA increase, marking the first instance of the reproducible expression of detectable amounts of recombinant full-length ORF2 protein in a mammalian system.

Example 2

Figure 2B:
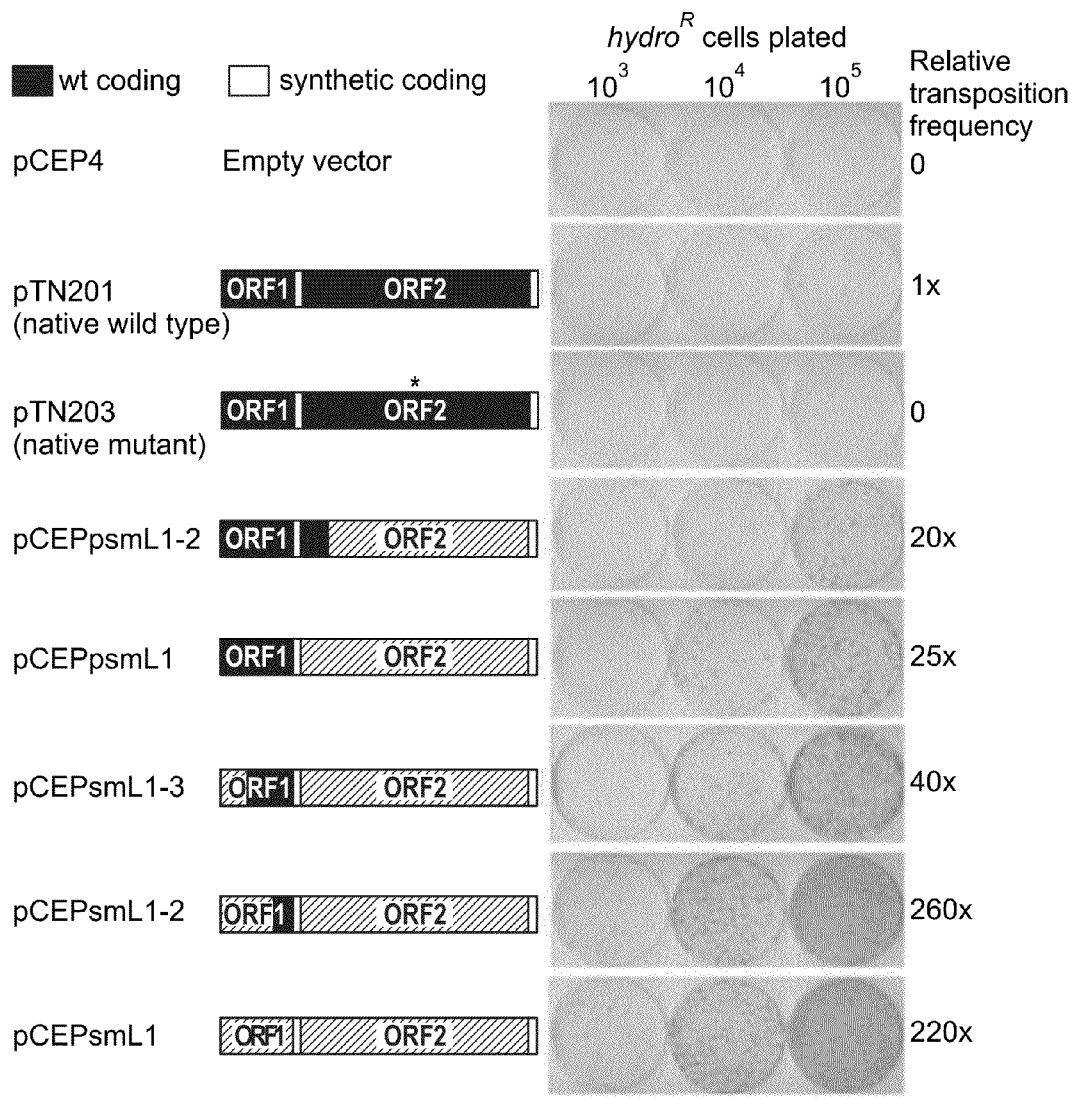
FIG. 2b shows the results obtained when retrotransposition was assayed in HeLa cells (N=3). pTN201 contains only wild-type native mouse L1 sequence, and $pTN_{203}$ contains wild-type native mouse L1 sequence with a D709Y reverse transcriptase point mutation. The average absolute number of colonies for pTN201 was 440 events per $10^6$ transfected cells.

In order to determine whether the increased RNA levels led to altered retrotransposition efficiency, an established tissue culture assay, the retrotransposition assay (FIG. 2a), was used to measure relative retrotransposition frequencies in HeLa cells. The standard retrotransposition assay in HeLa cells was performed essentially as described in Moran et al., 1996, Cell 87:917-927. Transfected cells were selected with 200 µg ml⁻¹ hygromycin for 10-12 days, then counted and seeded in 600 µg ml⁻¹ G418 for 10 days. Colonies were stained with 0.4% Giemsa in PBS.

mORF2 was replaced with smORF2 in a fill-length mouse L1 to make a partly synthetic mouse L1 (psmL1). Because we were concerned that recoded mORF2 might lack potentially important cis-acting sequences required for retrotransposition (for example, an internal ribosomal entry site), we also constructed a partly synthetic version of ORF2 (psmL1-2) in which the first roughly 500 bp of mORF2 consisted of wildtype L1 sequence and the remainder was synthetic. In HeLa cells, both psmL1 and psmL1-2 were about 20-25-fold more active than wild-type mL1 (FIG. 2b). Synthesis and incorporation of a synthetic mORF1 (smORF1) and partly synthetic mORF1 variants led to further increases in retrotransposition, reaching a maximum of more than 200-fold increase over wild type (FIG. 2b) in the element with two fully synthetic ORFs.

The transient retrotransposition assays in HeLa, 3T3 and L cells were performed essentially as described in Wei et al., 2000, Anal. Biochem. 284:435-438. Each transposition construct was cotransfected with the GFP-expressing plasmid pTracerEF (Invitrogen) to normalize for transfection efficiency. At 24 h after transfection, cells were split 1:2, 1:20 and 1:200 into 100-mm dishes. At 36 h after transfection, the diluted cells were selected with G418 and the remaining cells were analyzed for GFP expression by flow cytometry to normalize for transfection efficiency. 3T3 cells were selected in 1 mg ml$^{-1}$ G418; L cells were selected in 400 μg ml$^{-1}$ G418. Colonies were stained with 0.4% Giemsa or 0.5% Coomassie brilliant blue.

With the use of the transient assay, synthetic mouse L1 (pCEPsmL1) retrotransposition frequency was compared with that of wild-type native human L1 and wild-type native mouse L1 (N=3). The average absolute numbers of colonies of pJM101L1rp (colonies per $10^6$ transfected cells) for HeLa, 3T3 and L cells were 2,904, 108 and 1,568, respectively.

TABLE 1 high-frequency retrotransposition in mouse cells

| Plasmid | Relative transposition frequency | | |
|---|---|---|---|
| | HeLa | 3T3 | L |
| pCEP4 (empty vector) | 0 | 0 | 0 |
| pTN201 (native mouse wild-type) | <0.005 | <0.002 | <0.002 |
| pTN203 (native mouse mutant) | 0 | 0 | 0 |
| pJM101L1 (native human wild-type) | 0.13 | 0.017 | 0.07 |
| pCEPsmL1 (synthetic mouse wild-type) | 1 | 1 | 1 |
| pCEPsml1mut$^2$ (synthetic mouse mutant) | 0 | 0 | <0.002 |

Example 3

To verify that the smL1 G418-resistant colonies resulted from authentic L1 retrotransposition, we characterized six smL1 insertions. The mutant loci were identified by inverse polymerase chain reaction (PCR), enabling the amplification of each complete insertion and flanking sequence. For each primer pair, parental HeLa cells produced only empty site products (FIG. 3a, odd-numbered lanes), whereas the respective G418-resistant clones produced both empty site and filled smL1 insertion products of predicted sizes (FIG. 3a, even-numbered lanes).

Amplicons were cloned and sequenced to determine their general structures and genomic flanks. Integration sites were determined by inverted PCR essentially as described in Morrish et al., 2002, Nature Genet. 31:159-165. Genomic DNA (5 μg) from each clone was digested with EcoRI, inactivated by heat, diluted to 1 ml and ligated overnight, precipitated with ethanol, resuspended in 30 μl water and subjected to two rounds of inverted PCR with oligonucleotides JB6466/JB6467 (round 1) and JB6468/JB6469 (round 2). Sequencing with JB3529, JB3530 and JB3531 identified the 30 flanking sequences. Primers based on flanking sequence were used to amplify intact smL1 insertions, which were subsequently sequenced.

Figures 3A, 3B:
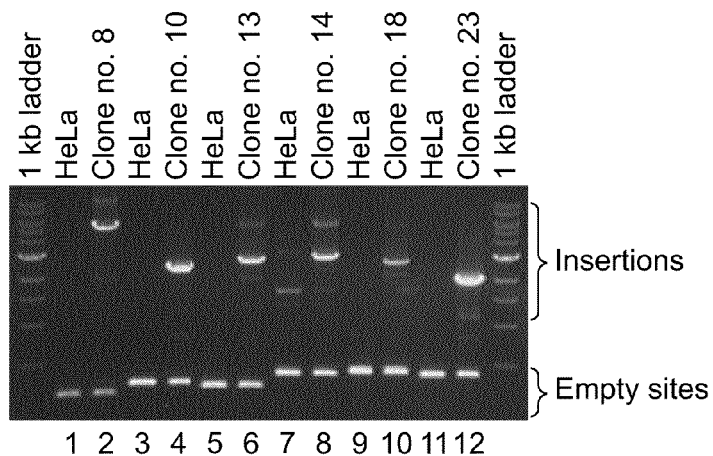
FIG. 3a shows the results of inverse polymerase chain reaction to amplify each complete insertion and flanking sequence. Primers flanking each insertion were used for amplification from G418-resistant clones. Odd-numbered lanes show that, for each primer pair, parental HeLa cells produced only empty site products. Even-numbered lanes show that the respective G418-resistant clones produced both empty site and filled smL1 insertion products of predicted sizes.
FIG. 3b provides characteristics of cloned insertions. TSD refers to target site duplication.

As summarized in FIG. 3b, all amplicons showed a properly spliced neo gene, a poly(A) tail, and most (five of six) had target site duplications 5-108 bp long. Insertion no. 10 had a 10-bp target deletion and insertion no. 18 had a 5' L1 inversion, features commonly found in L1 insertions.

Figure 3C:
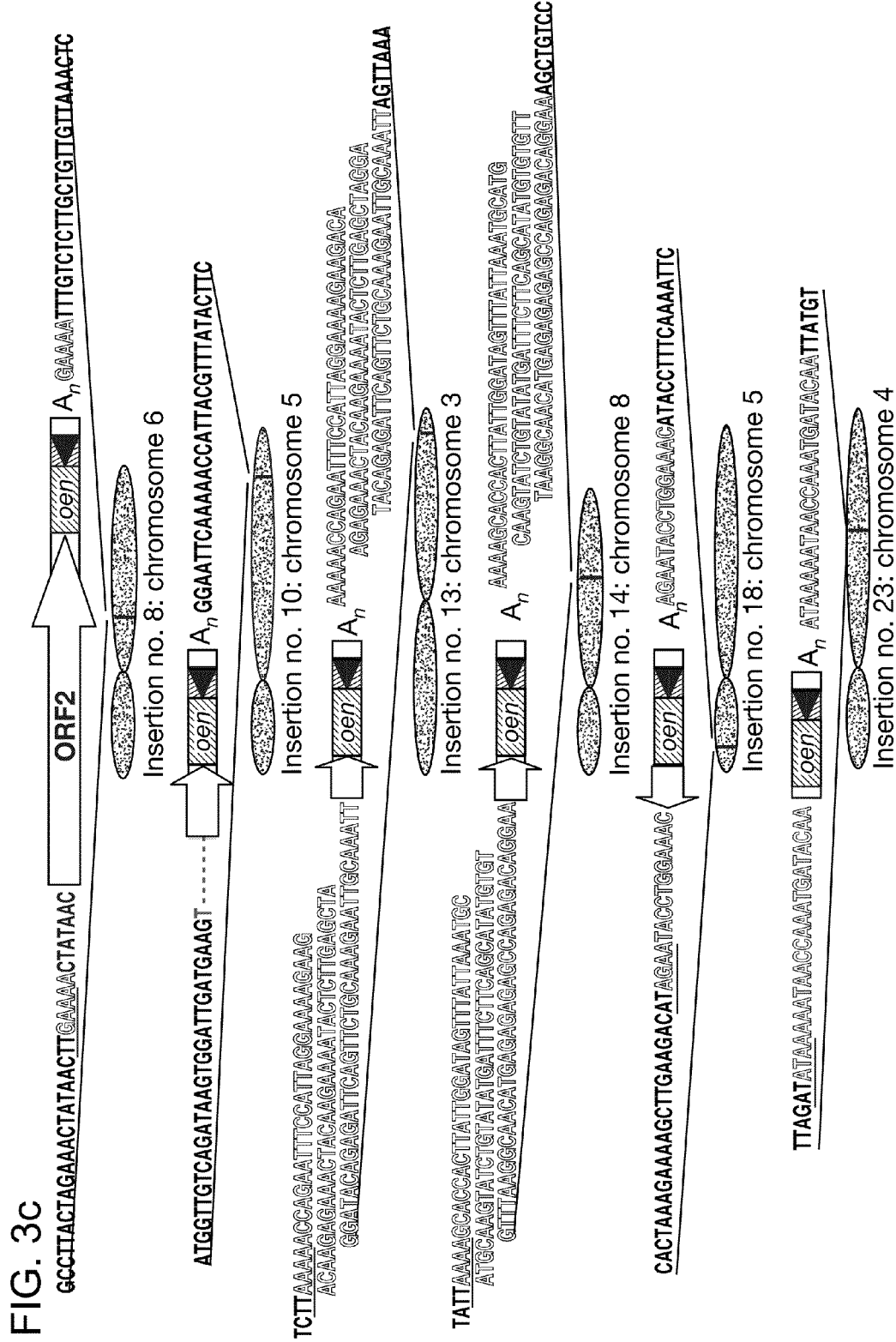
FIG. 3c depicts the structure and flanking sequence of cloned insertions schematically (nucleotides disclosed as SEQ ID NOS 412, 414, 416-418, 422-424, 428, and 430 respectively in order of appearance on the left side of the figure and nucleotides disclosed as 413, 415, 419-421, 425-427, 429, & 431 respectively in order of appearance on the right side of the figure). Insertion no. 8 contained an additional 7 bp (highlighted in blue) not found in the human genome sequence. Insertion no. 10 contained one untemplated base pair relative to the human genome sequence database followed by a 10-bp deletion (indicated in blue) immediately upstream of the L1 insertion. TSDs are highlighted in red, and presumptive endonuclease cleavage sites are underlined.

In addition, various chromosomes served as targets, and the endonuclease cleavage sites inferred from target site duplications matched the previously reported degenerate consensus (5'-TTTT/AA-3' on the bottom strand) (FIG. 3c).

Example 4

The activity of the synthetic mouse L1 retrotransposons was compared with wild-type human and mouse L1 in mouse cells. Because episomal plasmids used to introduce marked retrotransposons do not replicate efficiently in mouse cells, we used a transient retrotransposition assay in 3T3 and L cells. We also performed the transient assay in HeLa cells, verifying the relative retrotransposition frequencies obtained with the standard assay (compare pTN201 and pCEPsmL1 from FIG. 2b and table 1). The synthetic mouse L1 (pCEPsmL1) underwent retrotransposition at much higher frequencies (more than 200-fold) than its wild-type counterpart in mouse cells.

In addition, we compared smL1 with a human L1 (pJM101L1rp), because L1rp has previously been used to generate transgenic mouse lines and, thus, serves as a benchmark for retrotransposition frequencies in mice. smL1 was significantly more active than L1rp in all cell types tested, making it the most active L1 element known so far. Introducing catalytic mutations into smL1 to produce smL1mut$^2$ essentially abolished retrotransposition.

Example 5

Northern blot analysis of wild-type full-length mL1 and its synthetic counterparts was performed. Total RNA was isolated with TRIzol reagent (Invitrogen) in accordance with the manufacturer's instructions. Total RNA (6 μg) from each sample was treated with 10 units of DNase I for 15 min at 37 'C., then run on a 0.8% agarose/formaldehyde gel, blotted overnight to a Genescreen plus nylon membrane (NEN) in 10×SSC, and crosslinked by ultraviolet radiation. Prehybridizations and hybridizations were both performed in ULTRAhyb (Ambion) at 42° C. The following ['y-$^{32}$P]ATP end-labeled oligonucleotides were used as probes: GFP probe, JB4057; GFP plasmid neo probe, JB4059; transposition plasmid neo probe, JB4541; hyg probe, JB6341. Washes were performed in 2×SSC, 0.1% SDS and in 0.2×SSC, 0.1% SDS. Radioactive signal was detected with Fuji imaging plates and a Fuji scanner (BAS-1500). For subsequent reprobing, membranes were stripped with three 10-min washes in boiling 0.1×SSC, 1% SDS.

Figure 4:
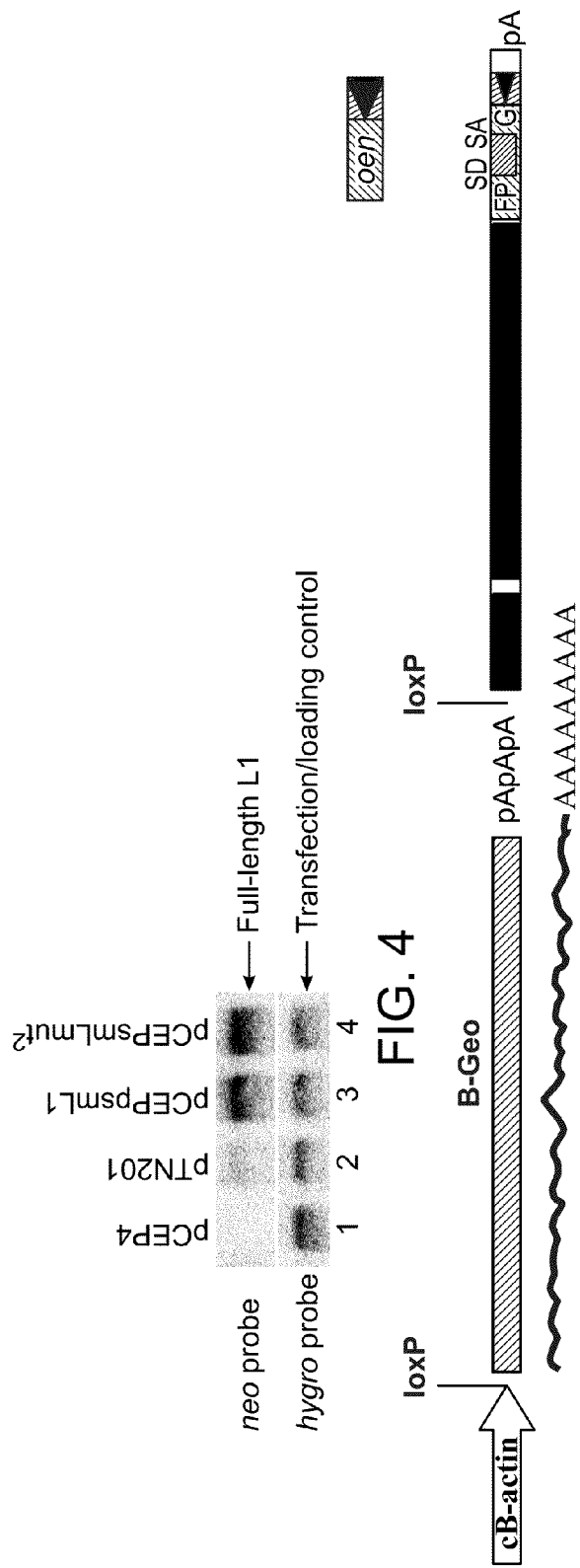
FIG. 4 depicts high-frequency retrotransposition in mouse cells: total RNA analysis of snL1 expression. Expression of native, partly synthetic, and completely synthetic mL1 was compared in HeLa cells.

The Northern blot analysis of wild-type full-length mL1 and its synthetic counterparts revealed that increasing lengths of synthetic L1 sequence led to increasing full-length L1 RNA levels (FIG. 4). pCEPsmL1mut$^2$ was used in place of pCEPsmL1, because pCEPsmL1 was difficult to maintain episomally, as determined by the hygro transfection/loading control (data not shown). The intact pCEPsmL1 plasmid is not maintained in transfected cells for long periods.

Example 6

Figure 5A:
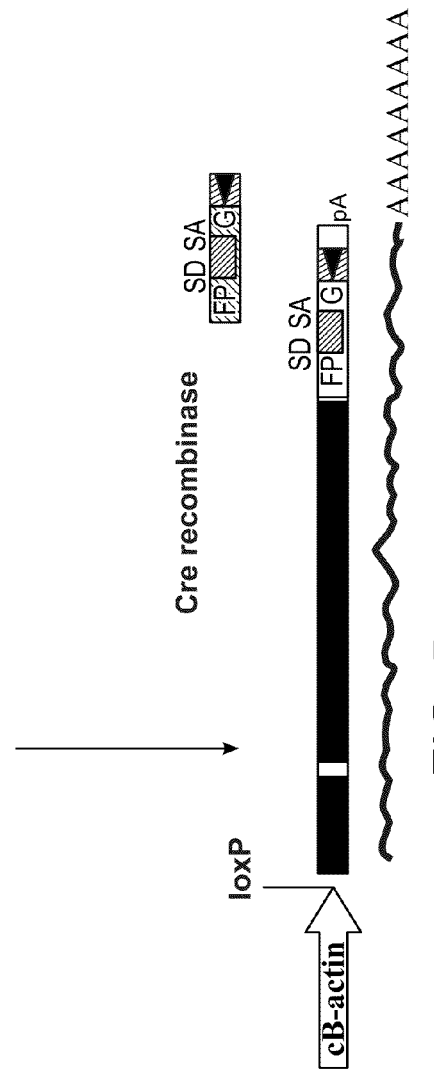
FIG. 5a schematically depicts the conditionally activated mouse retrotransposon which only retrotransposes when exposed to the cre recombinase protein.
Figure 12:
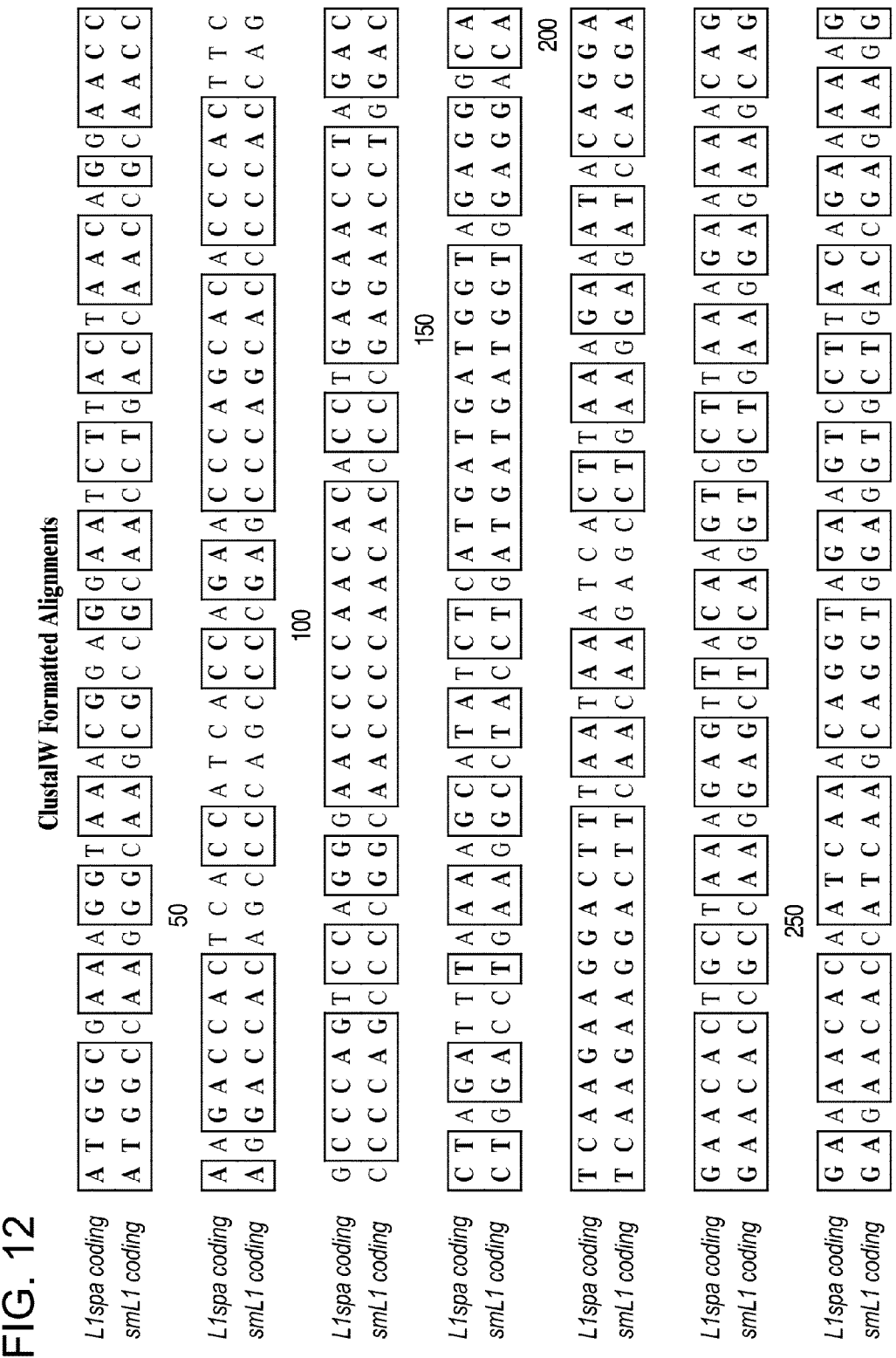
FIG. 12 provides a sequence alignment of native mouse L1 with synthetic mouse L1. MacVector 6.5.3 (Oxford Molecular) was used to create a nucleic acid ClustalW alignment of native mouse L1 (SEQ ID NO: 432) and synthetic mouse L1 (SEQ ID NO: 433), starting at the ATG of ORF1 and ending at the stop codon of ORF2. For these sequences, the base composition of L1 spa is 41% A, 20% T, 21% C, 18% G. The base composition of smL1 is 27% A, 14% T, 33% C, 26% G. L1spa (Genbank accession #AF016099) was used as the sequence for native mouse L1. Identities are shaded in grey.

A conditionally activated version synthetic mouse retrotransposon which only retrotransposes when exposed to the cre recombinase protein was constructed (FIG. 5a). A construct was created in which the synthetic retrotransposon is inactivated by an intervening reporter gene (such as β-GEO), operationally joined to sequences leading lead to premature RNA truncation. This cassette is flanked by the loxP recombination sited. When this DNA segment is in the presence of cre protein (provided in vitro, via co-transfection, or via cross-breeding to a cre-expressing transgenic mouse), cre will effect recombination at the loxP sites, deleting β-geo and activating the synthetic retrotransposon.

The reporter for retrotransposition is a UV-excited green fluorescent protein (gfp), which allows the tracking of new mutations visually by simply shining ultraviolet light on them. This is shown in FIG. 5b. The inactivated and activated DNA constructs (depicted in FIG. 5a) were transfected into HELA cells, and the phenotypes were assessed by X-gal staining for β-geo expression and fluorescence microscopy for transposition (gfp activity).

Example 7

A human version of a synthetic L1 element was synthesized using the same methods as described above. This element was based on the amino acid sequence of a consensus human L1 element (Brouha et al., 2003, Proc Natl Acad Sci USA 100:5280-5285). ORF1 and ORF2 were recoded, as well as the interORF region and 3'UTR, generating a completely synthetic human L1.

Retrotransposition activity was measured and revealed a several-fold increase in activity in comparison to native human L1.

The disclosures of each and every patent, patent application and publication cited herein are hereby incorporated herein by reference in their entirety.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A synthetic transposon gene comprising a DNA sequence selected from the group consisting of SEQ ID NO: 1, SEQ ID NO: 2, SEQ ID NO: 3, and SEQ ID NO: 4.

2. A transposon comprising a DNA sequence selected from the group consisting of SEQ ID NO: 1, SEQ ID NO: 2, SEQ ID NO: 3, and SEQ ID NO: 4.

* * * * *